(12) United States Patent
Demmer et al.

(10) Patent No.: US 9,266,924 B2
(45) Date of Patent: Feb. 23, 2016

(54) CYCLOPENTAPEPTIDE DERIVATIVES AND USES THEREOF

(75) Inventors: Oliver Demmer, Munich (DE); Horst Kessler, Garching (DE); Hans-Jürgen Wester, Ilmmunster (DE); Margret Schottelius, Munich (DE); Ingrid Dijkgraaf, Kranenburg (DE); Andreas Konard Buck, Munich (DE)

(73) Assignee: TECHNISCHE UNIVERSITÄT MÜNCHEN, München (DE)

( * ) Notice: Subject to any disclaimer, the term of this patent is extended or adjusted under 35 U.S.C. 154(b) by 177 days.

(21) Appl. No.: 13/641,947

(22) PCT Filed: Apr. 20, 2011

(86) PCT No.: PCT/EP2011/056358
§ 371 (c)(1),
(2), (4) Date: Jan. 29, 2013

(87) PCT Pub. No.: WO2011/131735
PCT Pub. Date: Oct. 27, 2011

(65) Prior Publication Data
US 2013/0129622 A1  May 23, 2013

Related U.S. Application Data

(60) Provisional application No. 61/325,956, filed on Apr. 20, 2010.

(30) Foreign Application Priority Data

Apr. 20, 2010 (EP) .................................. 10004177

(51) Int. Cl.
| A61K 51/00 | (2006.01) |
| A61M 36/14 | (2006.01) |
| C07K 7/64 | (2006.01) |
| A61K 51/08 | (2006.01) |

(52) U.S. Cl.
CPC ............... *C07K 7/64* (2013.01); *A61K 51/088* (2013.01)

(58) Field of Classification Search
CPC ..... A61K 51/00; A61K 51/08; A61K 51/088; A61K 38/00; C07K 7/64; C07K 7/56; C07K 7/06; C07K 7/08; C07K 9/008
USPC ........... 424/1.11, 1.65, 1.69, 1.81, 1.85, 1.89, 424/9.1, 9.3, 9.4, 9.5, 9.6, 9.7, 9.8; 514/1, 514/1.1; 534/7, 10–16; 530/300, 317, 330
See application file for complete search history.

(56) References Cited

U.S. PATENT DOCUMENTS 6,225,284 B1 * 5/2001 Albert et al. .................. 514/11.1
7,038,078 B2  5/2006 Aldrich et al.
7,211,240 B2 * 5/2007 Arbogast et al. ............... 424/9.1
8,614,290 B2 * 12/2013 Wester et al. .................. 530/321
8,628,750 B2 * 1/2014 Wester et al. ................ 424/1.69

FOREIGN PATENT DOCUMENTS

| WO | WO-89/07456 A1 | 8/1989 |
| WO | WO-97/31657 A2 | 9/1997 |
| WO | WO-2007/096662 A2 | 8/2007 |
| WO | WO-2008/008854 A2 | 1/2008 |
| WO | WO-2009/027706 A2 | 3/2009 |
| WO | WO-2009/109332 A1 | 9/2009 |
| WO | WO-2009/134382 A2 | 11/2009 |

OTHER PUBLICATIONS

Demmer et al, Organic Letters, 2008, vol. 10, No. 10, pp. 2015-2018.*

Edwards, Barry W. et al., "Multimodal imaging of integrin receptor-positive tumors by bioluminescense, fluorescence, gamma scintigraphy, and single-photon emission computed tomography using a cyclic RGD peptide labeled with a near-infrared fluorescent dye and a radionuclide," Molecular Imaging, MIT Press, U.S., vol. 8, No. 2, Mar. 1, 2009, pp. 101-110.

Burger-Kentischer, A. et al., "Expression of macrophage migration inhibitory factor in different stages of human artherosclerosis," Circulation, 2002, vol. 105, pp. 1561-1566.

Demmer, O. et al., "Introduction of functional groups into peptides via N-alkylation," Organic Letters, 2008, vol. 10, pp. 2015-2018.

Fujii, N. et al., "Molecular-sized reduction of a potent CXCR4-chemokine antagonist using orthogoonal combination of conformation- and sequence-based libraries,"Angewandte Chemie-International Edition, 2003, vol. 42, pp. 3251-3253.

Hansson, GK, "Inflammation, atherosclerosis, and coronary artery disease," N. Engl. J. Med., 2005, vol. 351, No. 16, pp. 1685-1695.

Kim, J. et al., "Chemokine receptor CXCR4 expression in colorectal cancer patients increases the risk for recurrence and for poor survival," J. Clin. Oncol., 2005, vol. 23, No. 12, pp. 2744-2753.

(Continued)

*Primary Examiner* — D L Jones
(74) *Attorney, Agent, or Firm* — Birch, Stewart, Kolasch & Birch, LLP

(57) ABSTRACT

The present invention, among others, relates to a compound having a structure according to formula (I) or a pharmaceutically acceptable salt thereof, wherein $Xaa^1$ to $Xaa^4$ are independently of each other, an optionally N-alkylated natural or unnatural amino acid, R is H or methyl, L is a linker moiety, Ar is a spacer comprising an aromatic moiety, and D comprises, preferably is i) a combination of an organic complexation agent and a detectable label; or ii) a detectable label, an organic complexation agent or an active substance, said active substance particularly being selected from cytotoxic agents, lipids, sugars, sugar conjugates, sugar derivatives, proteins and combinations thereof, with the proviso that -L-Ar-D does not comprise a $^{18}$F-benzoyl residue.

17 Claims, 11 Drawing Sheets

(56) References Cited

OTHER PUBLICATIONS

Kuehl, H. et al., "Can PET/CT replace separate diagnostic CT for cancer imaging? Optimizing CT protocols for imaging cancers of the chest and abdomen." J. Nucl. Med., 2007, vol. 48, Suppl 1, pp. 45S-57S.

Levesque, J. P. et al., "Mobilization of hematopoietic stem cells: State of the art," Curr. Opin. Organ Transplant, 2008, vol. 13, No. 1, pp. 53-58.

Libby, P., "Inflammation in atherosclerosis," Nature, 2002, vol. 420, pp. 868-874.

Mizukami, S. et al., "Paramagnetic relaxation-based F-19 MRI probe to detect protease activity," Journal of the American Society, 2008, vol. 130, pp. 794-795.

Phillips, RJ. et al., "The stromal derived factor-1/CXCL12-CXC chemokine receptor 4 biological axis in non-small cell lung cancer metastases." Am. J. Respir. Crit. Care Med., 2003, vol. 167, No. 12, pp. 1676-1686.

Ross, R., "The pathogenesis of atherosclerosis: A perspective for the 1990s," Nature, 1993, vol. 362, pp. 801-880.

Schober, A. et al., Chemokine-like functions of MIF in atherosclerosis, J. Mol. Med., 2008, vol. 86, pp. 761-770.

Shah, K. et al., "Molecuar optical imaging: applications leading to the development of present day thereapeutics," NeuroRx, 2005, vol. 2, No. 2, pp. 215-225.

Taniuchi, S. et al., "The role of a mutation of the CXCR4 gene in WHIM syndrome," Haematologica, 2005, vol. 90, No. 9, pp. 1271-1712.

Van Der Plas, S. E. et al., "Synthesis of a tripdal scaffold for solid phase synthesis of artificial receptors," European Journal of Organic Chemistry, 2008, vol. 9, pp. 1582-1588.

Weissleder, R. et al., "Shedding light onto live molecular targets," Nat. Med., 2003, vol. 9, No. 1, pp. 123-128.

Weissleder, R. et al., "Imaging in the era of molecular oncology," Nature, 2008, vol. 452, No. 7187, pp. 580-589.

Yang, P. Y. et al., "Solid-phase synthesis of azidomethylene inhibitors targeting cysteine proteases," Organic Letters, 2008, vol. 10, pp. 1881-1884.

Zhang et al., Inorg. Chem. 1998, vol. 37, No. 5, pp. 956-963.

Phillips, RJ. et al., "The stromal derived factor-1/CXCL12-CXC chemokine receptor 4 biological axis in non-small cell lung cancer metastases." Am. J. Respir. Crit. Care Med., 2003, vol. 167, No. 12, pp. 1676-1686.

* cited by examiner

Fig. 10
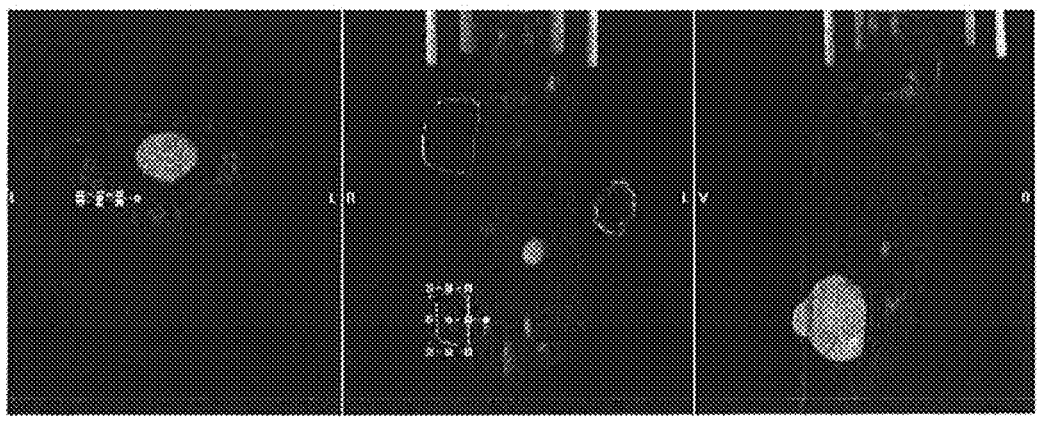
Fig. 11
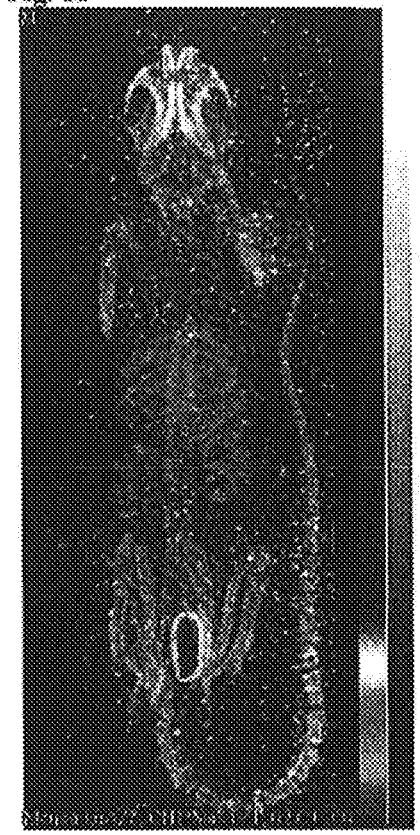
Mouse 1
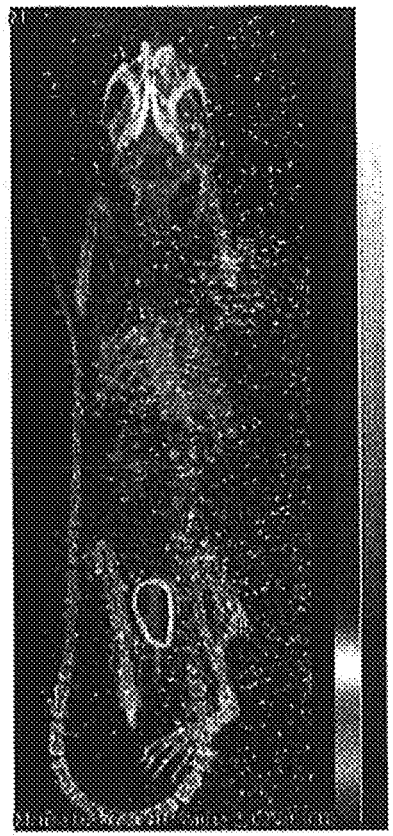
Mouse 2

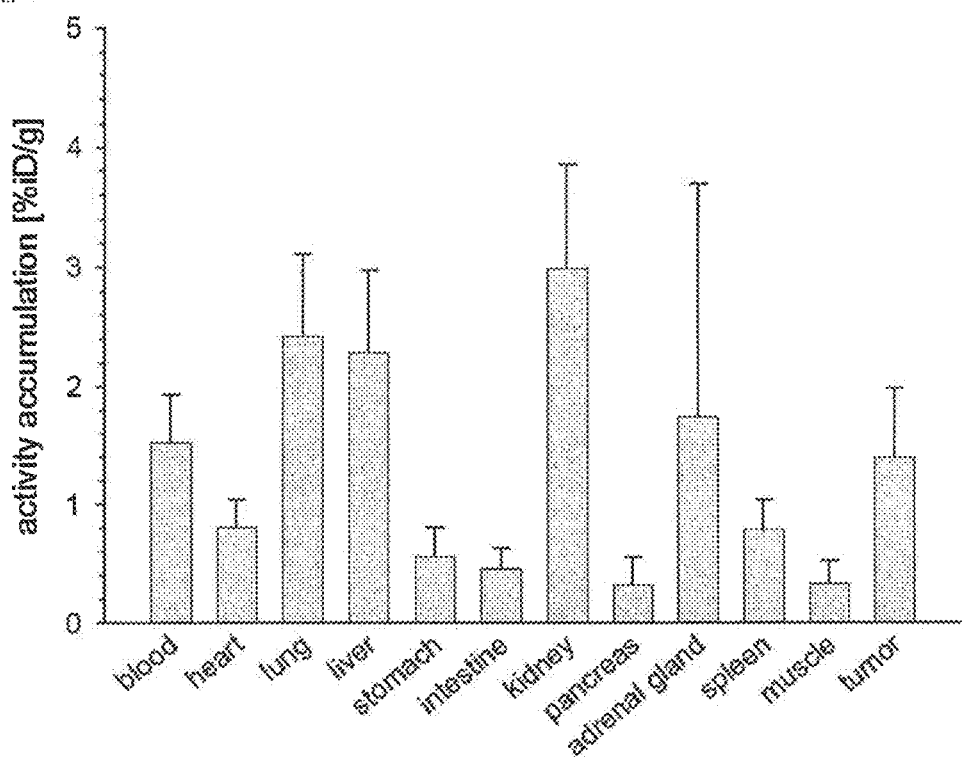
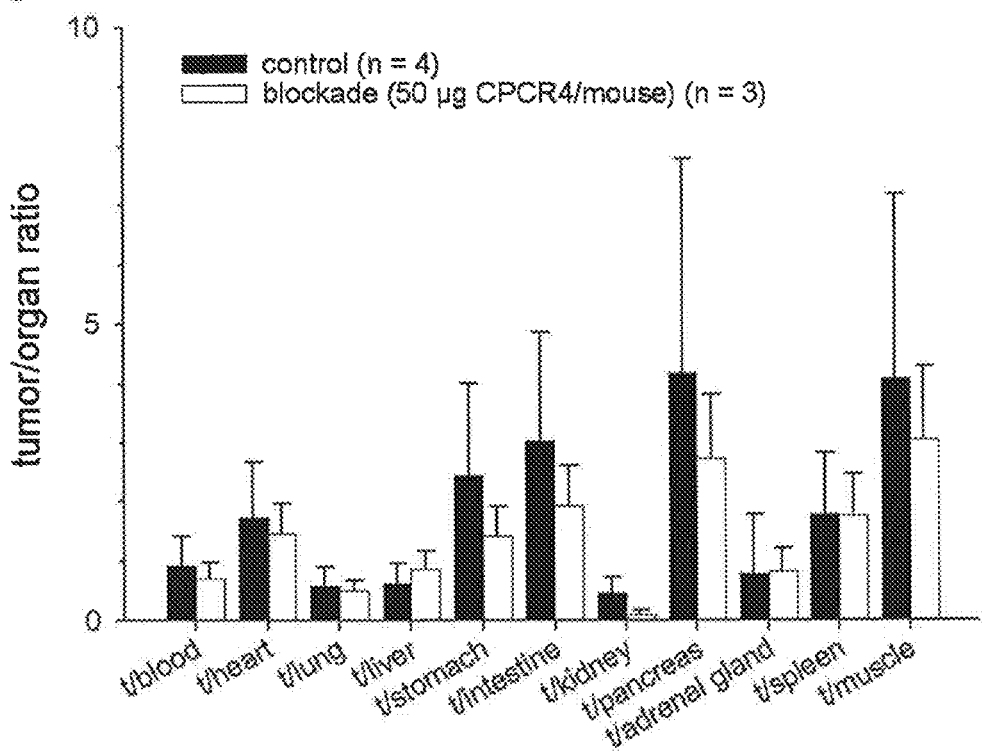

CYCLOPENTAPEPTIDE DERIVATIVES AND USES THEREOF

This application is the National Phase Under 35 U.S.C. §371 of PCT International Application No. PCT/EP2011/056358 which has an International filing date of Apr. 20, 2011, which claims priority to European Patent Application No. 10004177.1 filed on Apr. 20, 2010, and to U.S. Provisional Application No. 61/325,956 filed on Apr. 20, 2012. The entire contents of all applications listed above are hereby incorporated by reference.

The present invention is, among others, concerned with cyclopeptide derivatives, with processes for their preparation, pharmaceutical compositions comprising same and various embodiments relating to the application of said derivatives including imaging and medical applications. Specifically, the present invention relates to a compound having a structure according to general formula (I)

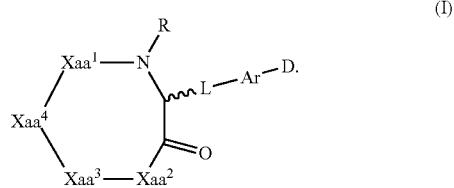

The compounds of the invention are believed to be capable of binding to the seven transmembrane G-protein coupled chemokine receptor CXCR4 with high affinity and are thus considered CXCR4 ligands. They may act as antagonists, agonists or inverse agonists.

The interaction between CXCR4 and its natural ligand α-chemokine stromal-derived factor (SDF-1α/CXCL12) is a key factor in diverse bodily functions. Starting at the beginning of life with normal stem cell trafficking during embryogenesis it is also responsible for normal cardiovascular, hematopoietic and brain development as well as functions in the nervous and immune system.

The CXCR4 receptor has been found to be involved in a variety of diseases. For example, it mediates HIV-1 entry into T-cells as a co-receptor where it was first identified. Furthermore, in rheumatoid arthritis (RA) CXCR4 expressing CD4+ memory T cells accumulate in the inflamed synovium because of the high local CXCL12 concentration. Additionally CXCR4 is overexpressed on numerous different tumor cell types ranging from melanoma over prostate and pancreatic cancer to brain tumor cells.

Coronary heart disease has become a leading cause of death worldwide. The pathologic basis for coronary heart disease (CHD) is the growth of atherosclerotic plaques in the vascular wall over a period of many years resulting in bloss-flow-limiting stenosis or plaques disruption with acute thrombotic occlusion (Ross, 1993; Libby, 2002; Hansson 2005). Substantial evidence supports the concept that chronic inflammation of the vessel wall characterized by the influx of circulating immune cells is responsible for the development of atherosclerotic lesions (Schober et al., 2008).

In the pathogenesis of atherosclerosis, chronic inflammation of the arterial wall characterized by chemokine-mediated influx of leukocytes plays a central role. The cytokine macrophage migration inhibitory factor (MIF) is a unique pro-inflammatory regulator of many acute and chronic inflammatory diseases that contribute to lesion progression and plaque inflammation. These chemokine-like functions are mediated through interaction of MIF with the chemokine receptors CXCR2 and CXCR4, thus demonstrating the role of CXCR4 in native atherosclerosis, plaque destabilization and aneurysm formation.

Via binding of MIF, CXCR4 and other chemokine receptors, like CXCR2 play a role in atherosclerotic plaque development, vascular remodeling after injury, in atherosclerosis plaque destabilization and aneurysm formation (Schober et al., 2008).

Like chemokines, the interaction of MIF with the chemokine receptors CXCR2 and CXR4 as a noncanonical ligand induces recruitment of monocytes and T cells to atherosclerotic lesions, Furthermore, MIF regulates smooth muscle cell migration and proliferation, which may promote lesion growth. Increased foam-cell transformation of lesional macrophages and enhanced degradation of extracellular matrix proteins by MIF contribute to the progression into an unstable plaque phenotype. These data were largely confirmed in a study using human specimens from patients undergoing heart transplantation, carotis endarterectomy, or from autopsied individuals (Burger-Kentischer et al, 2002).

Accordingly, due to their potential use for medicinal applications, a variety of peptidic and non-peptidic CXCR4 antagonists have been developed. One example is the bicyclam AMD3100 (plerixafor)

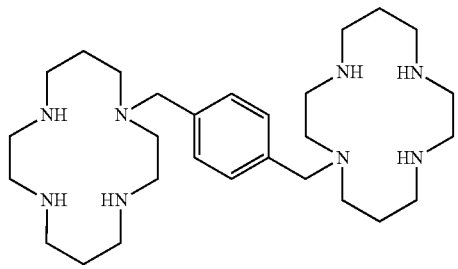 [SMILES: c1cc(CN2CCCNCCNCCCNCC2)ccc1CN1CCCNCCNCCCNCC1]

that has been approved by the FDA for the treatment of the two blood cancer types non-Hodgkin's lymphoma and multiple myeloma. Based on the structure of AMD3100 further CXCR4 antagonists such as peptidic CXCR4 antagonists have been developed. Examples include T140 and its derivatives which are side-chain cyclized peptides that contain one or two cyclization sites. Further downsizing of T140 gave the head-to-tail cyclized pentapeptide FC131 with good antagonistic activity (Fujii et al., 2003). A potential advantage of CXCR4 antagonists derived from T140, like FC131, may be their suggested mechanism of action as inverse agonists in contrast to agents like AMD3100 which are partial agonists. Furthermore, a number of modifications of FC131 have been described (WO 2007/096662). However, no aromatic spacers between a linker attached to a cyclopeptide and a detectable label are described. Besides, certain multimeric and in particular dimeric compounds of such cyclized pentapeptides have been described, wherein a spacer moiety between the monomeric ligands is selected such that the ligands are spaced apart to avoid an interference between both ligands. (WO 2009/027706).

Barry et al. describes cyclic RGD peptides labeled with a DOTA as chelator coupled via a non aromatic spacer moiety, wherein the spacer moiety is attached to the cyclic RGD peptide with a (—CH$_2$)$_4$NH-group (Barry et al, 2009).

Also known are radiolabeled cyclic polypeptides, which use non-aromatic heterocycles as spacer moiety (WO 2009/134382).

So far, therapeutic potential of CXCR4 ligands, such as antagonists, has been shown e.g. for the treatment of HIV infection, cancer, and rheumatoid arthritis. Other anti-inflammatory uses of CXCR4 ligands have been described for asthma and multiple sclerosis. Furthermore, CXCR4 ligands can mobilize stem cells, e.g. for stem cell transplantations. Moreover, attenuation of pain has been observed (in rodents) by a specific CXCR4 ligand. In addition CXCR4 ligands are also discussed for the treatment of neurological diseases.

CXCR4 ligands comprising additional moieties may be particularly suitable in the treatment of the above diseases. Examples for the latter ligands include but are not limited to those comprising cytotoxic, (oligo)nucleotide, radioactive, and (radio)metal-chelate moieties or combinations thereof. The general concepts pursued with such moieties are known from certain other peptidic and peptidomimetic ligands.

In addition to the therapeutic potential of CXCR4 ligands, their affinity towards the receptor may be used for other applications. These include but are not limited to the imaging of CXCR4 receptors, e.g. for the diagnosis of related diseases or the visualization of CXCR4 and CXCR4 containing tissue, as well as affinity purification of CXCR4 receptors. In most of these cases, the CXCR4 ligands are modified with additional (functional) moieties and/or moieties that immobilize the CXCR4 ligands.

However, the attachment of such additional moieties to the CXCR4 ligands may result in that the ligands substantially loose their affinity to the CXCR4 receptor. Therefore, there is a need in the art to develop new CXCR4 ligands, particularly ligands having high affinity to CXCR4, more particularly such ligands that allow the introduction of additional (functional) moieties while retaining sufficient affinity to the CXCR4 receptor.

The present invention provides such new CXCR4 ligands and their uses in medicinal and scientific applications as well as such ligands comprising additional (functional) moieties and their uses in medicinal and scientific applications.

The compounds of the invention are considered capable of binding to CXCR4 and, hence, are considered CXCR4 ligands. They may be capable of functioning as CXCR4 antagonists, agonists or inverse agonists. Generally, they are based on the peptide backbone structure of FC131. However, as opposed to the compounds known from the prior art, compounds of the present invention comprise a particular linker and further moieties. These advantageously enable e.g. various imaging applications referred to herein. Surprisingly, compounds of the invention are shown herein to have high affinity to the CXCR4 receptor despite the attachment of said linker and additional moieties such as a detectable label. As shown herein, surprisingly, compounds of the invention are considered particularly suitable for medical applications such as imaging and therapeutic applications, such as endoradiotherapy.

The present invention provides compounds, compositions, uses and methods as defined in the claims. In one aspect, the present invention thus provides a compound, or a pharmaceutically acceptable salt thereof, having a structure according to formula I

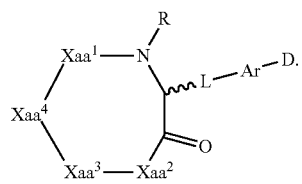

(I)

or a pharmaceutically acceptable salt thereof, wherein $Xaa^1$ to $Xaa^4$ are independently of each other, an optionally N-alkylated natural or unnatural amino acid, R is H or methyl, L is a linker moiety, Ar is a spacer comprising an aromatic moiety, and D comprises, preferably is i) a combination of an organic complexation agent and a detectable label;

or ii) a detectable label, an organic complexation agent or an active substance, said active substance particularly being selected from cytotoxic agents, lipids, sugars, sugar conjugates, sugar derivatives, proteins and combinations thereof, with the proviso that -L-Ar-D does not comprise a $^{18}F$-benzoyl residue.

In the compounds of the invention having a structure according to formula I the carbonyl carbon atom of $Xaa^2$ is linked to the $N^{alpha}$ atom of $Xaa^3$, the carbonyl carbon atom of $Xaa^3$ is linked to the $N^{alpha}$ atom of $Xaa^4$, and the carbonyl carbon atom of $Xaa^4$ is linked to the $N^{alpha}$ atom of $Xaa^1$.

Furthermore, the present invention relates to methods for preparing the above mentioned compound. The invention also relates to compositions, methods and uses related to said compounds.

BRIEF DESCRIPTION OF THE DRAWINGS

FIG. 10 shows PET imaging of OH-1 tumor bearing CD1 nu/nu mouse using [$^{68}$Ga]CPCR4-2.

FIG. 11 shows SPECT imaging of OH-1 tumor bearing CD1 nu/nu mouse using [177Lu]CPCR4-2.

FIG. 12 shows biodistribution of yorn'(AMBS-[$^{68}$Ga]DOTA)RNalG ([$^{68}$Ga]CPCR4-2) in PC-3 tumor bearing CD1 nu/nu mice at 60 min p.i., n=4.

FIG. 13 shows tumor-to-organ ratios of yorn'(AMBS-[$^{68}$Ga]DOTA)RNalG (PC-3 tumor bearing CD1 nude mice, 60 min p.i., n=3-4.

FIG. 17 shows $^{68}$Ga-CPCR4-2.1: imaging in OH-1 tumor bearing mice.

FIG. 18 shows another example of $^{68}$Ga-CPCR4-2.1 imaging in OH-1 tumor bearing mice.

DETAILED DESCRIPTION OF THE INVENTION

Figure 1:
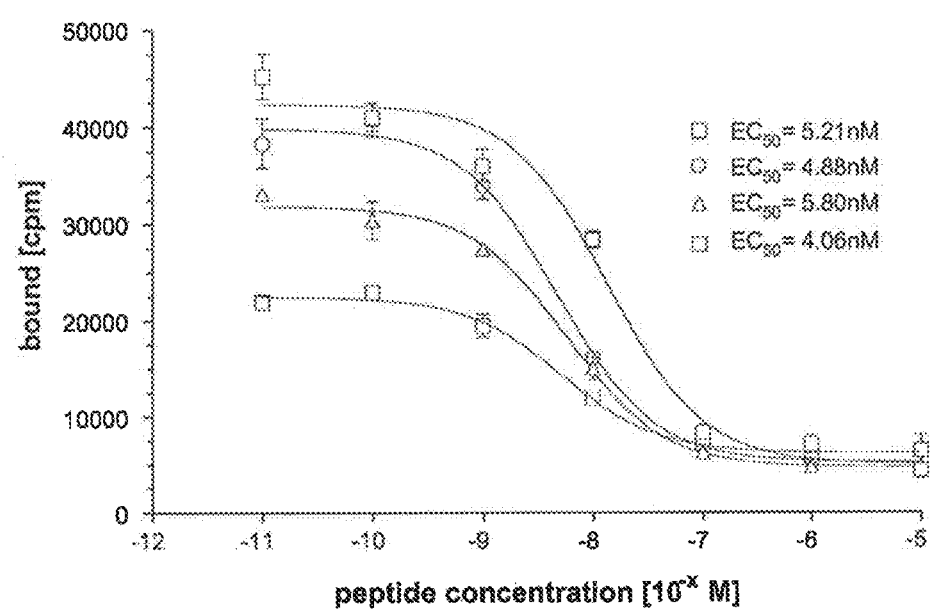
FIG. 1 shows an analysis of cell tests for CPCR4-2 with GraphPad-Prism 4.

The present invention provides compounds, compositions, uses and methods as defined and described in the claims and hereinbelow.

The Structural Unit -Xaa-:

As far as the structural units -Xaa$^1$-, -Xaa$^2$-, -Xaa$^3$- and -Xaa$^4$- are concerned, in the context of the present invention, the general structure -Xaa- is denoted to encompass natural as well as unnatural amino acids, optionally being substituted at the alpha nitrogen (N-alpha) of said amino acid with an alkyl group, such as a methyl group or ethyl group.

In this context, the term "alkyl group" preferably refers to a linear or branched, optionally substituted, saturated aliphatic chain of preferably 1 to 12, more preferably 1 to 8, and more preferably 1 to 6 carbon atoms and includes, but is not limited to, optionally substituted methyl, ethyl, propyl, isopropyl, n-butyl, sec-butyl, tert-butyl, pentyl, isopentyl, and hexyl. The alkyl group may be interrupted by one or more heteroatoms, cyclic groups and/or heterocyclic groups. The term "substituted" as used in this context preferably refers to alkyl groups being substituted in any position by one or more substituents, preferably by 1, 2, 3, 4, 5 or 6 substituents, more preferably by 1, 2, or 3 substituents. If two or more substituents are present, each substituent may be the same or may be different from the at least one other substituent. Suitable substituents are known to the skilled person. A substituent may be, for example, a halogen atom, a hydroxy, an amino group or an alkoxy group. In this context, the term "alkoxy" preferably represents a linear or branched alkyl group, preferably having from 1 to 6 carbon atoms attached to an oxygen atom. Typical alkoxy groups include methoxy, ethoxy, propoxy, isopropoxy, butoxy, t-butoxy, pentoxy, and the like. The term "halogen atom" preferably refers to a chlorine, iodine, bromine or fluorine atom. Preferred halogen atoms are fluorine and/or chlorine atoms.

Preferably the amino acids -Xaa$^1$-, -Xaa$^2$-, -Xaa$^3$- and -Xaa$^4$- are, independently of each other either N-alpha-methylated amino acids or are substituted with a hydrogen (H) in N-alpha-position. Preferably all amino acids -Xaa$^1$-, -Xaa$^2$-, -Xaa$^3$- and -Xaa$^4$- are substituted in N-alpha-position with a hydrogen.

The term "natural amino acid" refers to naturally occurring amino acids or residues which typically occur in proteins including their stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

The term unnatural amino acid includes any conceivable amino acid. This term includes amino acids bearing a side chain comprising acidic, basic, neutral and/or aromatic moieties. Conceivable amino acids to be mentioned are, for example, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, naphthylalanine, diaminopropionic acid, N-(fluoropropionyl)diaminobutyric acid, N-fluorobenzoyl-diaminobutyric acid, N-fluorobenzoyl-diaminopropionic acid, citrulliune and pipecolic acid.

As regards the general amino acid abbreviations Xaa$^1$, Xaa$^2$, Xaa$^3$, Xaa$^4$, said abbreviations encompass the L-enantiomer as well as the respective D-enantiomers.

The Amino Acid Xaa$^1$:

Xaa$^1$ is a natural or unnatural amino acid. In the context of the present invention the term "natural or unnatural amino acid" refers to residues of any naturally occurring or synthetic amino acid and their respective D and L stereoisomers if their structures allow such stereoisomeric forms.

In this context of the invention, the term residues refers to building blocks being incorporated in the cyclic pentapeptide having the structure:

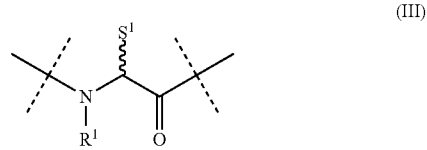

(III)

wherein S$^1$ is the side chain of the natural or unnatural amino acid. For example in case the amino acid is glycine S$^1$ is a hydrogen atom. S$^1$ may form a cyclic ring with the group N, in particular in case Xaa$^1$ is proline or a proline derivative.

R$^1$ in the above shown structure is a hydrogen atom or an alkyl group, preferably a hydrogen atom or a methyl group, in particular a hydrogen atom.

Thus, more preferably Xaa$^1$ is a building block having the structure:

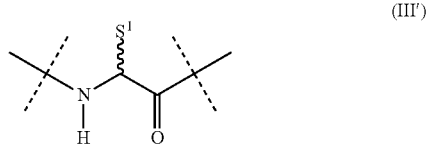

(III')

said building block being incorporated in the cyclic pentapeptide of formula (I).

Preferably Xaa$^1$ is a naturally or unnaturally amino acid comprising an aromatic moiety in its side chain S$^1$. The term "amino acid comprising an aromatic moiety in its side chain" refers to an amino acid, the side chain of which comprises an aromatic group. Side chains comprising an aromatic moiety includes side chains, with the aromatic moiety being directly attached to the C$^{alpha}$ of the amino acid, thus with S$^1$ being the aromatic moiety, as well as side chains being substituted in any position with at least one aromatic moiety, such as for example alkyl chains being substituted with an aromatic moiety.

The term aromatic moiety as used in this context of the invention, refers to an optionally substituted aryl group and/or heteroaryl group, wherein the term "aryl", in turn, refers to, but is not limited to, optionally suitably substituted 5- and 6-membered single-ring aromatic groups as well as optionally suitably substituted multicyclic groups, for example bicyclic or tricyclic aryl groups. The term "aryl" thus includes, for example, optionally substituted phenyl groups or optionally suitably substituted naphthyl groups. Aryl groups can also be fused or bridged with alicyclic or heterocycloalkyl rings which are not aromatic so as to form a polycycle, e.g., benzodioxolyl or tetraline. The term heteroaryl includes optionally suitably substituted 5- and 6-membered single-ring aromatic groups as well as substituted or =substituted multicyclic aryl groups, for example tricyclic or bicyclic aryl groups, comprising one or more, preferably from 1 to 4 such as 1, 2, 3 or 4, heteroatoms, wherein in case the aryl residue comprises more than 1 heteroatom, the heteroatoms may be the same or different. Such heteroaryl groups including from 1 to 4 heteroatoms are, for example, benzodioxolyl, pyrrolyl, furanyl, thiophenyl, thiazolyl, isothiaozolyl, imidazolyl, triazolyl, tetrazolyl, pyrazolyl, oxazolyl, isoxazolyl, pyridinyl, pyrazinyl, pyridazinyl, benzoxazolyl, benzodioxazolyl, benzothiazolyl, benzoimidazolyl, benzothiophenyl, methylenedioxyphenylyl, naphthridinyl, quinolinyl, isoquinolinyl, indolyl, benzofuranyl, purinyl, benzofuranyl, deazapurinyl, or indolizinyl.

The term "substituted aryl" and the term "substituted heteroaryl" as used in the context of the present invention describes moieties having substituents replacing a hydrogen on one or more atoms, e.g. C or N, of an aryl or heteroaryl moiety. There are in general no limitations as to the substituent. The substituents may be, for example, selected from the group consisting of alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, amino, acylamino, including alkylcarbonylamino, arylcarbonylamino, carbamoyl and ureido, amidino, nitro, imino, sulfhydryl, alkylthio, arylthio, thiocarboxylate, sulfates, alkylsulfinyl, sulfonate, sulfamoyl, sulfonamido, trifluoromethyl, cyano, azido, heterocyclyl, alkylaryl, morpholino, piperizinyl, cyclopentanyl, cyclohexanyl, and piperidinyl.

In case $S^1$ comprises an aryl group or heteroaryl being substituted at at least one position, the at least one substituent is preferably selected from the group consisting of alkyl, halogen, amino and hydroxyl.

In case $S^1$ is an aryl group or a heteroaryl being substituted with an amino group, the term "amino" is meant to encompass, for example, groups such as —$NH_2$, alkylamino, dialkylamino, acylamino, diarylamino, and alkylarylamino groups. In case $S^1$ comprises an aryl group or a heteroaryl group being substituted at at least one position with an amino group, the amino group is preferably selected from the group consisting of methylamino, dimethylamino, ethylamino, diethylamino, benzylamino, and dibenzylamino.

In this context of the present invention, the term "halogen" or "halogen atom" preferably refers to a chlorine, iodine, bromine or fluorine atom and the respective radioactive and non-radioactive isotopes. Thus, the term halogen is, for example, selected from the group consisting of Cl, Br, $^{127}I$, $^{123}I$, $^{120}I$, $^{124}I$, $^{125}I$, $^{131}I$, $^{75}Br$, $^{76}Br$, $^{77}Br$, $^{18}F$, and $^{19}F$ and $^{34}Cl$. Preferred halogen atoms are fluorine and/or iodine atoms. The term halogen also includes the respective isotopes of these atoms. Thus, in case the $S^1$ comprises an aryl group or heteroaryl being substituted at at least one position with an iodine, the iodine may be selected from the group consisting of $^{127}I$, $^{123}I$, $^{120}I$, $^{124}I$, $^{125}I$, and $^{131}I$. In case $S^1$ comprises an aryl group or heteroaryl being substituted at at least one position with a fluorine atom, the fluorine atom may be selected from the group consisting of $^{18}F$ and $^{19}F$.

The term "alkyl chain" and the term "alkyl", as used in this context of the invention preferably refers to alkyl chains or alkyl groups of 1 to 20 carbon atoms, preferably of 1 to 10 carbon atoms, more preferably of 1 to 8 carbon atoms, most preferably of 1 to 6 carbon atoms, such as for example, 1, 2, 3, 4, 5 or 6 carbon atoms. The alkyl chains or alkyl groups, respectively, may be branched or unbranched, substituted or unsubstituted, and may be interrupted by one or more heteroatoms, cyclic groups and/or heterocyclic groups.

The amino acid $Xaa^1$ may have multiple asymmetric centers. As a consequence, the resulting cyclopeptides may occur as racemates, mixtures of enantiomers and as individual enantiomers, as well as diastereomers and mixtures of diastereomers. All asymmetric forms, possible stereoisomers, single isomers and mixtures of isomers are included within the scope of the present invention. The designation "⁓" shown in formulas (III) and (III') above refers to a bond to which the stereochemistry is not specifically designated.

Preferably, $Xaa^1$ is present in enantiomerically pure form.

The term "enantiomerically pure" as used in the context of the present invention refers to compounds having an enantiomeric excess of at least 95% (i.e. minimum 97.5% of one enantiomer and maximum 2.5% of the other enantiomer) up to an enantiomeric excess of 100% (i.e. 100% of one enantiomer and none of the other), in particular compounds having an enantiomeric excess of at least 98%, more in particular having an enantiomeric excess of at least 99.0% and most in particular having an enantiomeric excess of at least 99.9%, especially of 100%.

Most preferably, the amino acid $Xaa^1$ is present in D-configuration. Thus, the present invention also relates to a compound having the following structure with $Xaa^2$ to $Xaa^4$, L, Ar, D and R being as described above and below:

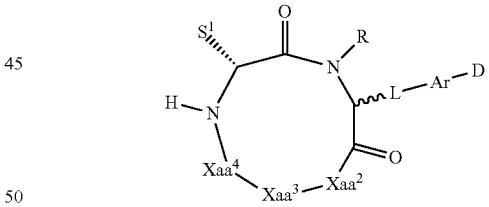

As regards the side chain $S^1$, preferably said side chain comprises an aromatic group being selected from, optionally substituted, phenyl, naphthyl and indole, most preferably, $S^1$ is selected from the group consisting of optionally substituted, phenyl, optionally further substituted, hydroxy-phenyl, an optionally further substituted group having the following structure

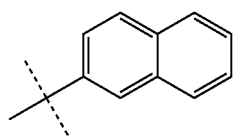

or an optionally further substituted group having the following structure

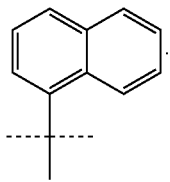

Thus, in other words, $Xaa^1$ is preferably selected from the group consisting of phenylalanine, tyrosine, tryptophan, phenylglycine, and naphthylalanine, i.e. $Xaa^1$ is preferably selected from the group consisting of L-phenylalanine (Phe), D-phenylalanine (D-Phe), L-tyrosine (Tyr), D-tyrosine (D-Tyr), L-tryptophan (Trp), D-tryptophan (D-Trp), D-phenylglycine, L-phenylglycine (Phg), L-naphthylalanine (Nal) and D-naphthylalanine (D-Nal).

In case $Xaa^1$ is a "L-naphthylalanine", said building block preferably has a structure selected from the structures

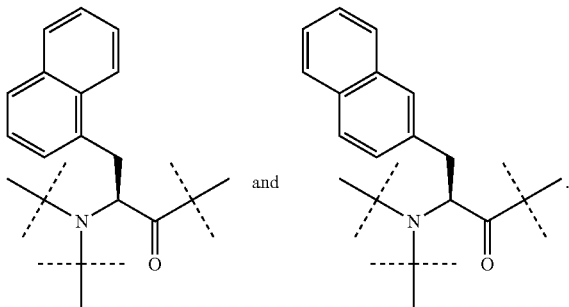

According to a preferred embodiment, $Xaa^1$ is tyrosine or D-tyrosine. Thus, the present invention also relates to a compound having the general structure:

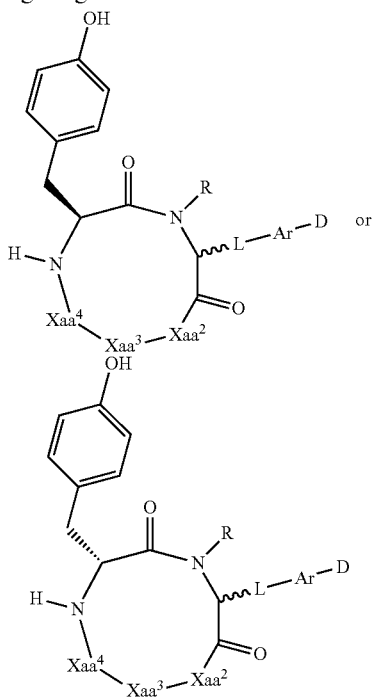

with $Xaa^2$ to $Xaa^4$, L, Ar, D and R being as described above and below. Most preferably, $Xaa^1$ is D-tyrosine.

The Amino Acid $Xaa^2$:

$Xaa^2$ preferably is a natural or unnatural basic amino acid. In the context of the present invention the term "natural or unnatural basic amino acid" refers to residues of any naturally occurring or synthetic amino acid comprising a basic group in its side chain and their respective D and L stereoisomers if their structures allow such stereoisomeric forms.

The term "basic amino acid" refers to any amino acid having a basic residue such as a primary, secondary or tertiary amine, or a cyclic nitrogen containing ring and their respective isomeric forms. Basic preferably means a group, which has a net positive charge at pH 6 or lower in aqueous solvents. Naturally occurring basic amino acids or residues which typically occur in proteins include arginine (Arg), histidine (His) and lysine (Lys).

The term unnatural basic amino acid includes any conceivable basic amino acid, thus this term includes amino acids comprising at least one basic moiety in its side chain.

In this context of the invention, the term residues refers to building blocks being incorporated in the cyclic pentapeptide having the structure:

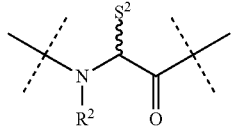

(IV)

wherein $S^2$ is the side chain of the natural or unnatural basic amino acid, $S^2$ may form a cyclic ring with the group N, in particular in case $Xaa^2$ is a proline derivative.

$R^2$ in the above shown structure is a hydrogen atom or an alkyl group, preferably a hydrogen atom or a methyl group, in particular a hydrogen atom.

Thus, more preferably $Xaa^2$ is a building block having the structure:

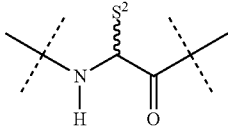

(IV')

said building block being incorporated in the cyclic pentapeptide of formula (I).

Preferably $S^2$ comprises at least one basic group, preferably one basic group selected from the group consisting of amino groups, guanidine groups or guanidine mimics. According to one preferred embodiment, $S^2$ comprises a guanidine group.

According to a preferred embodiment of the invention $S^2$ is an alkyl chain being substituted with the at least one basic group, thus, preferably with one basic group selected from the group consisting of amino groups, guanidine groups guanidine mimics, most preferably with a guanidine group. Basic group and basic moiety are used interchangeably herein.

The amino acid $Xaa^2$ may have multiple asymmetric centers. As a consequence, the resulting cyclopeptides may occur as racemates, mixtures of enantiomers and as individual enantiomers, as well as diastereomers and mixtures of diastereomers. All asymmetric forms, possible stereoisomers, single isomers and mixtures of isomers are included within the scope of the present invention. The designation "⌇" shown in formulas (IV) and (IV') above refers to a bond to which the stereochemistry is not specifically designated.

Preferably, the amino acid Xaa² is present in L-configuration. Thus, the present invention also relates to a compound having the following structure:

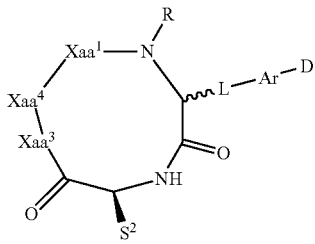

more preferably, the following structure:

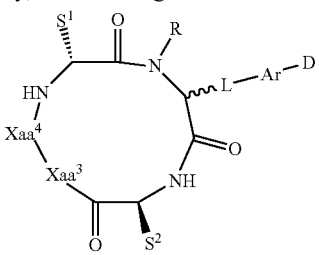

As regards, the side chain S², preferably said side chain is an alkyl chain having from 1 to 6, preferably from 1 to 4, carbon atoms, wherein said alkyl chain is substituted with a functional group selected from the group of —NH₂ and guanidine.

Especially preferred amino acids to be mentioned for Xaa² are, for example, ornithine (Orn or D-Orn), diaminopropionic acid (Dap or D-Dap), arginine, lysine or homolysine.

More preferably Xaa² is L-arginine or D-arginine, in particular L-arginine.

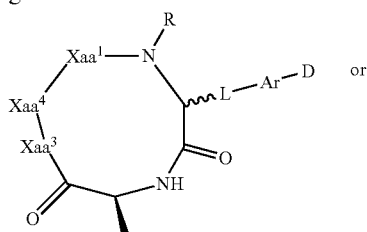 or

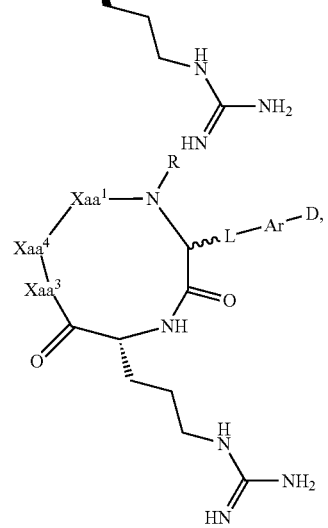

more preferably

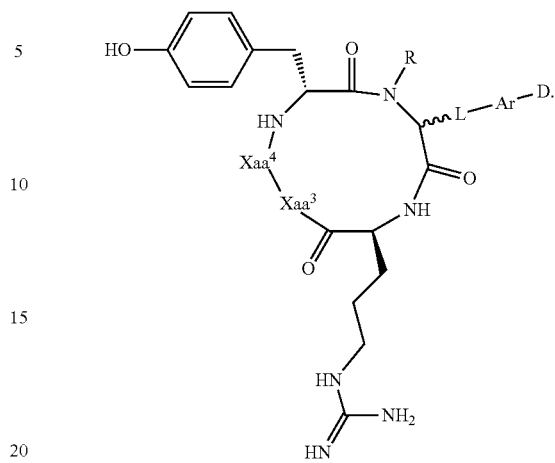

The Amino Acid Xaa³:

Xaa³ is a natural or unnatural amino acid. As already described above, the term "natural or unnatural amino acid" refers to residues of any naturally occurring or synthetic amino acid and their respective D and L stereoisomers if their structures allow such stereoisomeric forms.

In this context of the invention, the term residues refers to building blocks being incorporated in the cyclic pentapeptide having the structure:

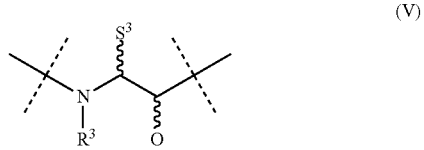

(V)

wherein S³ is the side chain of the natural or unnatural amino acid. For example in case the amino acid is glycine S³ is H. S³ may form a cyclic ring with the group N, in particular in case Xaa³ is proline or a proline derivative.

R³ in the above shown structure is a hydrogen atom or an alkyl group as defined above, preferably a hydrogen atom or a methyl group, in particular a hydrogen atom.

Thus, more preferably Xaa³ is a building block having the structure:

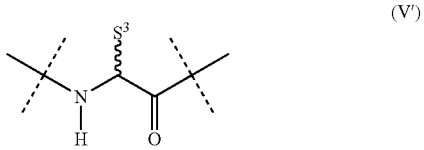

(V')

said building block being incorporated in the cyclic pentapeptide of formula (I).

Preferably Xaa³ is a naturally or unnaturally amino acid comprising an aromatic moiety in its side chain S³. As regards, the term "amino acid comprising an aromatic moiety in its side chain" this term refers to an amino acid, the side chain of which comprises an aromatic group as described above. This includes side chains, with the aromatic moiety being directly attached to the $C^{alpha}$ of the amino acid, thus with S³ being the aromatic moiety, as well as side chains S³ being substituted in any position with at least one aromatic moiety, such as for example alkyl chains being substituted with an aromatic moiety.

The term aromatic moiety as used in this context of the invention, refers to an optionally substituted aryl group and/or optionally substituted heteroaryl group, with the terms, terms "aryl" and "substituted aryl", "heteroaryl" and "substituted heteroaryl" being as defined above.

The amino acid Xaa³ may have multiple asymmetric centers. As a consequence, the resulting cyclopeptides may occur as racemates, mixtures of enantiomers and as individual enantiomers, as well as diastereomers and mixtures of diastereomers. All asymmetric forms, possible stereoisomers, single isomers and mixtures of isomers are included within the scope of the present invention. The designation "⁓" shown in formula (V) and (V') above refers to a bond to which the stereochemistry is not specifically designated.

Preferably, Xaa³ is present in enantiomerically pure form. Preferably, the amino acid Xaa³ is present in L-configuration. Thus, the present invention also relates to a compound having the following structure:

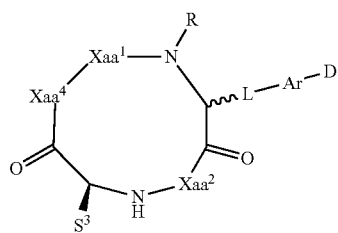

more preferably, the following structure:

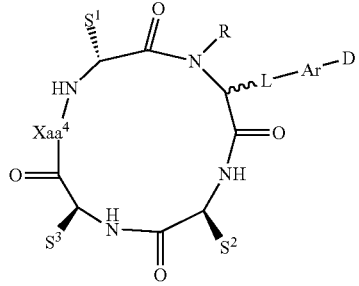

As regards the side chain S³, according to a preferred embodiment of the present invention, said side chain comprises an aromatic group being selected from, optionally substituted, phenyl, naphthyl and indole, most preferably, S³ comprises an aromatic group being naphthyl.

According to a preferred embodiment, Xaa³ is selected from the group consisting of phenylalanine, tyrosine, tryptophan, phenylglycine, and naphthylalanine, i.e. Xaa³ is most preferably selected from the group consisting of L-phenylalanine (Phe), D-phenylalanine (D-Phe), L-tyrosine (Tyr), D-tyrosine (D-Tyr), L-tryptophan (Trp), D-tryptophan (D-Trp), D-phenylglycine (D-Phg), L-phenylglycine (Phg), L-naphthylalanine (Nal) and D-naphthylalanine (D-Nal).

Thus, the present invention relates to a compound, as described above, wherein Xaa¹ and Xaa³ are, independently of each other, selected from the group phenylalanine, D-phenylalanine, tyrosine, D-tyrosine, tryptophan, D-tryptophan, D-phenylglycine, phenylglycine, naphthylalanine (Nal) and D-naphthylalanine (D-Nal).

According to preferred embodiments, Xaa³ is tryptophan or naphthylalanine.

According to a particular preferred embodiment, Xaa³ is L-naphthylalanine (Nal) or D-naphthylalanine (D-Nal), more preferably L-naphthylalanine.

In case, Xaa³ is Nal, e.g. the following structures are conceivable:

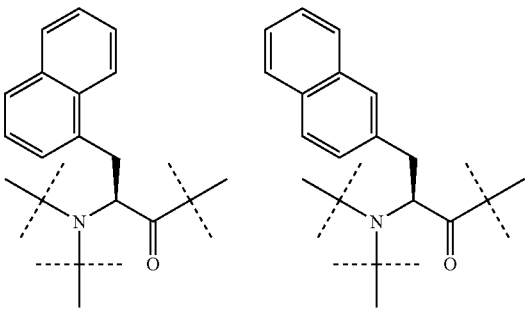

with L-2-naphthylalanine (2-Nal) being particularly preferred.

Thus according to a particular preferred embodiment, the present invention relates to a compound having the structure:

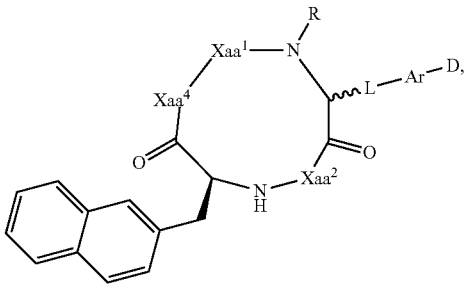

more preferably the structure:

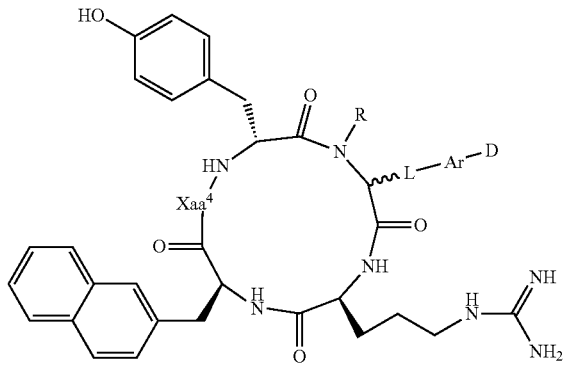

According to other particularly preferred embodiments of the invention, Xaa³ is tryptophan.

The Amino Acid Xaa⁴;

Xaa⁴ preferably is glycine or a D-amino acid of a natural or unnatural amino acid. As already described above, the term "natural or unnatural amino acid" refers to residues of any naturally occurring or synthetic amino acid. In this context of the invention, the term residues refers to building blocks being incorporated into the cyclic pentapeptide having the structure:

(VI)

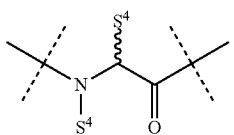

wherein $S^4$ is the side chain of the natural or unnatural amino acid. For example, in case the amino acid is glycine, $S^4$ is H. $S^4$ may form a cyclic ring with the group N, in particular in case $Xaa^4$ is a proline derivative $R^4$ in the above shown structure is a hydrogen atom or an alkyl group as defined above, preferably a hydrogen atom or a methyl group, in particular a hydrogen atom.

Thus, more preferably $Xaa^4$ is a building block having the structure:

(VI')

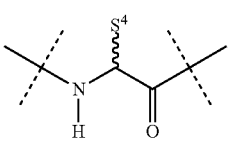

said building block being incorporated in the cyclic pentapeptide of formula (I).

According to one preferred embodiment, $S^4$ is the side chain of the natural or unnatural amino acid.

In case $Xaa^4$ is a D-amino acid, the D-amino acid is preferably selected from the group consisting of D-diaminopropionic acid, D-diaminobutyric acid, D-ornithine, and D-lysine.

The amino acid $Xaa^4$ may have multiple asymmetric centers. As a consequence, the resulting cyclopeptides may occur as racemates, mixtures of enantiomers and as individual enantiomers, as well as diastereomers and mixtures of diastereomers. All asymmetric forms, possible stereoisomers, single isomers and mixtures of isomers are included within the scope of the present invention. The designation "⁓" in formula (VI) and (VI') above refers to a bond to which the stereochemistry is not specifically designated. Preferably, the stereocenter in $C^{alpha}$ position, which is shown as "⁓" in formula (VI) and (VI') is selected in the way that, in case $Xaa^4$ is not glycine, the resulting amino acid $Xaa^4$ is present in D-conformation.

Preferably, $Xaa^4$ is present in enantiomerically pure form. Preferably, the amino acid $Xaa^4$ is present in D-configuration. Thus, the present invention also relates to a compound having the following structure:

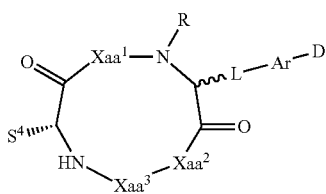

more preferably, the following structure:

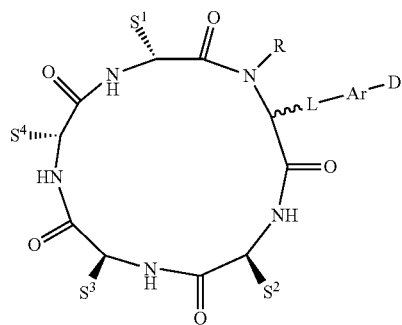

According to a preferred embodiment, $Xaa^4$ is selected from the group consisting of D-diaminopropionic acid, D-diaminobutyric acid, D-ornithine, D-lysine.

Thus, the present invention also relates to compounds having one of the following structures, particularly wherein $S^1$, $S^2$ and $S^3$ are preferably as defined hereinabove:

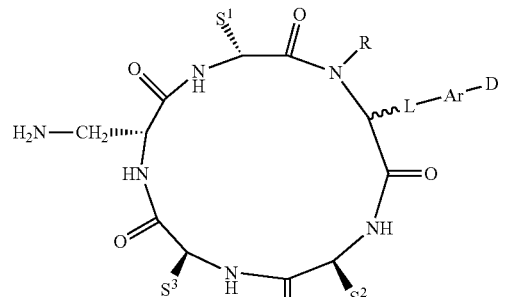

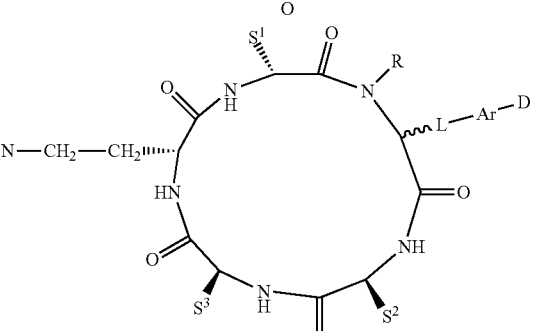

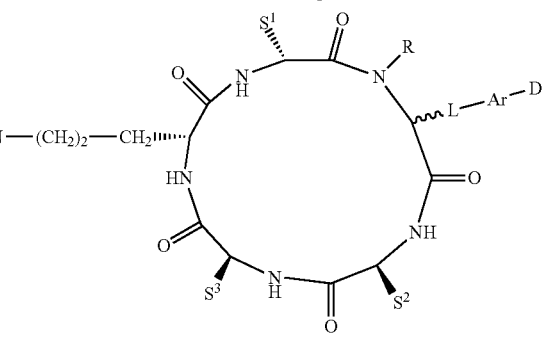

-continued

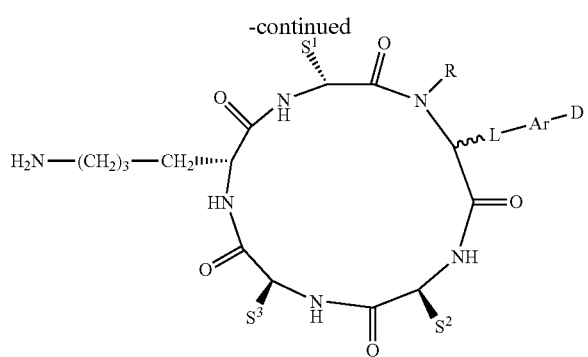

According to another preferred embodiment, Xaa⁴ is glycine. Thus, the invention particularly also relates to compounds having the following structure, especially the subsequent structure:

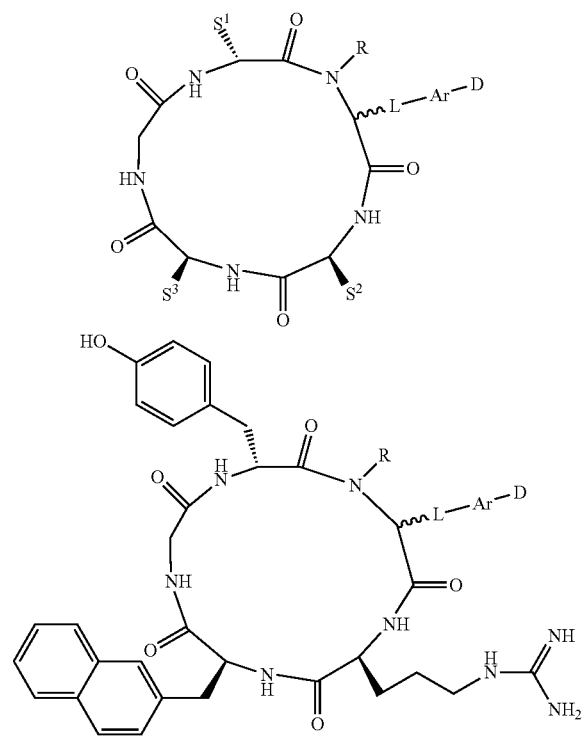

The Residue R:

As regards residue R, this residue is a methyl group or a hydrogen, preferably a methyl group.

The Structural Unit L-Ar

In general, there are no particular restrictions as to the chemical nature of the linker L and Ar with the proviso that the structural unit -L-Ar— is suitable for linking the further compound D to the alpha-carbon-atom of the backbone of the pentapeptide and provides suitable chemical properties for the novel derivatives as far as their intended uses are concerned.

Preferably the linker L is a spacer comprising at least one structural unit having the formula —(C(R⁵R⁶))ₙ— wherein R⁵ and R⁶ are, independently from each other, a hydrogen or a residue selected from the group consisting of, optionally substituted, alkyl, alkenyl, alkynyl, aryl, arylalkyl, and alkylaryl. More preferably R⁵ and R⁶ are, independently from each other, H or an alkyl group, most preferably, both R⁵ and R⁶ are H.

As far as integer n is concerned, n is preferably from 1 to 20, preferably from 1 to 15, more preferably from 1 to 10, more preferably from 1 to 5, such as 1, 2, 3, 4 or 5, more preferably 3.

If integer n is greater than 1, the groups —C(R⁵R⁶)— may be the same or different from each other. Furthermore, these groups may be linked directly to each other or at least two such structure units may be separated by a heteroatom such as O or S.

According to a preferred embodiment of the present invention, groups —C(R⁵R⁶)— directly linked to each other have the same constitution. Most preferably L thus comprises the group —(CH₂)ₙ— with n being from 1 to 10, preferably from 1 to 5, in particular 3.

Therefore, according to a particularly preferred embodiment of the present invention, spacer L comprises the group —CH₂—CH₂—CH₂—.

According to an alternative embodiment, L comprises at least one structure unit —[(CR⁵R⁶)ₙ—O—(CR⁵R⁶)ₘ]ₚ—, preferably —[(CH₂)ₙ—O—(CH₂)ₘ]ₚ— wherein n is equal to or different from m and wherein m and n are, independently of each other from 0 to 10, with the proviso that when one of n and m is 0, the other one is not 0, preferably wherein m+n=2; and wherein p is from 1 to 10, preferably from 1 to 5, more preferably from 1 to 2.

Besides the structural unit —(C(R⁵R⁶))ₙ-L preferably further comprises at least one chemical moiety different from —(CR⁵R⁶)—. Said chemical moiety is preferably a functional group X. The functional group X is preferably linking L and Ar.

In general, there no particular restrictions as to the chemical nature of the functional group X, with the proviso that, if present, the functional group X is suitable for linking the linker L to the moiety Ar. Preferably the functional group X is linked to a functional group Y optionally being present in the moiety Ar.

The functional group X may be, for example a group derived from a group selected from the group consisting of C—C-double bond, thio group, hydroxy group, hydrazide, azides; amino group —NH₂, derivatives of an amino groups comprising the structure unit —NH—, a hydroxylamino group —O—NH₂, a carboxy group, a carbonyl group, a thio reactive group such as a maleimide group, a halogen group, an alkynyl group or the like. According to a most preferred embodiment, L comprises a functional group being an amino group —NH₂ or a derivative of an amino group comprising the structure unit —NH—.

Likewise the functional group Y of the Ar moiety may be, for example a group derived from a group selected from the group consisting of C—C-double bond, thio group, hydroxy group, hydrazide, azides; amino group —NH₂, derivatives of an amino groups comprising the structure unit —NH—, a hydroxylamino group —O—NH₂, a carboxy group, a carbonyl group, a thio reactive group such as a maleimide group, a halogen group, an alkynyl group or the like.

If present, both functional groups X and Y preferably form a linking group selected from the group consisting of =N—, —N=, —Z—, —C(=Z)—NH—, —NH—C(=Z)—, —NH—C(=Z)—Z'—, —Z'—C(=Z)—NH—, —Z'—C(=Z)—, —C(=Z)—Z'—, —C(=Z), —S—S—, —S—CH₂—C(=O)—O—, —O—C(=O)—CH₂—S—, —S-maleimide-, -maleimide-S—, —C=NH—O—, —O—NH=C— and 1,2,3-triazole, with Z and Z' being independently of each other selected from the group consisting of NH, O and S, preferably wherein L comprises a —NH—C(=O)— group.

Thus, the present invention also relates to a compound having the following structure:

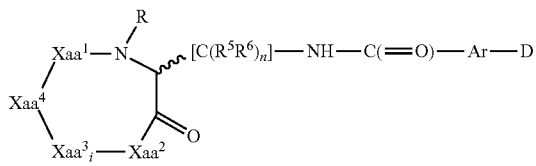

Thus, the present invention also relates to a compound, as described above, wherein L is a linker moiety comprising at least one functional group, the at least one functional group being selected from the group consisting of =N—, —N=, —Z—, —C(=Z)—NH—, —NH—C(=Z)—, —NH—C(=Z)—Z'—, —Z'—C(=Z)—NH—, —Z'—C(=Z)—, —C(=Z)—Z'—, —C(=Z), —S—S—, —S—CH$_2$—(=O)—O, —O—C(=O)—CH$_2$—S—, —S-maleimide, -maleimide-S—, —C=NH—O—, —O—NH=C—, and 1,2,3-triazole, with Z and Z' being independently of each other selected from the group consisting of NH, O and S, preferably wherein L comprises a —NH—C(=O)— group.

Most preferably the linker L is the side chain of an amino acid such as lysine, homolysine, glutamic acid, aspartic acid, cysteine, serine, ornithine, threonine. Thus, the linker L is preferably selected from the following structures:

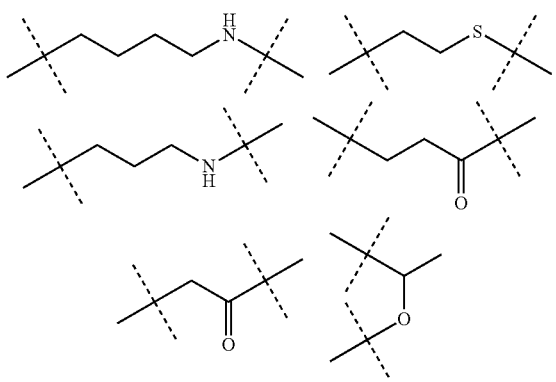

Most preferably L is selected from the followings structures:

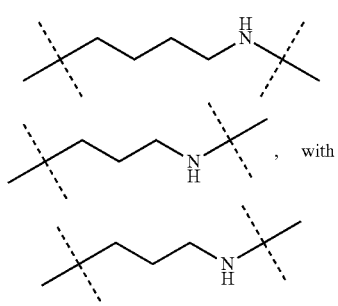

, with being preferred.

As regards the moiety Ar, there are no particular restrictions as to the chemical nature of Ar with the proviso that Ar comprises an aromatic moiety.

The term aromatic moiety as used in this context of the invention, refers to an optionally substituted aryl group and/or heteroaryl group, wherein the term "aryl", in turn, refers to, but is not limited to, optionally suitably substituted 5- and 6-membered single-ring aromatic groups as well as optionally suitably substituted multicyclic groups, for example bicyclic or tricyclic aryl groups. The term "aryl" thus includes, for example, optionally substituted phenyl groups or optionally suitably substituted naphthyl groups. Aryl groups can also be fused or bridged with alicyclic or heterocycloalkyl rings which are not aromatic so as to form a polycycle, e.g., benzodioxolyl or tetraline. The term heteroaryl includes optionally suitably substituted 5- and 6-membered single-ring aromatic groups as well as substituted or unsubstituted multicyclic aryl groups, for example tricyclic or bicyclic aryl groups, comprising one or more, preferably from 1 to 4 such as 1, 2, 3 or 4, heteroatoms, wherein in case the aryl residue comprises more than 1 heteroatom, the heteroatoms may be the same or different. Such heteroaryl groups including from 1 to 4 heteroatoms are, for example, benzodioxolyl, pyrrolyl, furanyl, thiophenyl, thiazolyl, isothiaozolyl, imidazolyl, triazolyl, tetrazolyl, pyrazolyl, oxazolyl, isoxazolyl, pyridinyl, pyrazinyl, pyridazinyl, benzoxazolyl, benzodioxazolyl, benzothiazolyl, benzoimidazolyl, benzothiophenyl, methylenedioxyphenylyl, naphthridinyl, quinolinyl, isoquinolinyl, indolyl, benzofuranyl, purinyl, benzofuranyl, deazapurinyl, or indolizinyl.

The term "substituted aryl" and the term "substituted heteroaryl" as used in the context of the present invention describes moieties having substituents replacing a hydrogen on one or more atoms, e.g. C or N, of an aryl or heteroaryl moiety. There are in general no limitations as to the substituent. The substituents may be, for example, selected from the group consisting of alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, amino, acylamino, including alkylcarbonylamino, arylcarbonylamino, carbamoyl and ureido, amidino, nitro, imino, sulfhydryl, alkylthio, arylthio, thiocarboxylate, sulfates, alkylsulfinyl, sulfonate, sulfamoyl, sulfonamido, trifluoromethyl, cyano, azido, heterocyclyl, alkylaryl, morpholino, piperizinyl, cyclopentanyl, cyclohexanyl, and piperidinyl.

Preferably, Ar comprises a phenyl group.

Besides, the aryl group and/or heteroaryl group, Ar further optionally comprises further spacer groups. Preferably the aryl group and/or heteroaryl group is linked via a spacer moiety to the further compound D ("spacer 1" or "spacer moiety 1") and/or via a spacer moiety ("spacer 2" or "spacer moiety 2") to linker L.

As regards, the spacer moiety 1, said group preferably comprises at least one functional group W, linking the aryl group and/or heteroaryl group to the further compound D.

The functional group W may be, for example, a group derived from a group selected from the group consisting of C—C-double bond, thio group, hydroxy group, hydrazide, azides; amino group —NH$_2$, derivatives of amino groups comprising the structure unit —NH—, a hydroxylamino group —O—NH$_2$, a carboxy group, a carbonyl group, a thio reactive group such as a maleimide group, a halogen group, an alkynyl group or the like. Preferably W is a —NH— group.

Optionally, spacer moiety 1, additionally comprises at least one structural unit having the formula —(C(R$^7$R$^8$))$_q$— wherein R$^7$ and R$^8$ are, independently from each other, a hydrogen or a residue selected from the group consisting of, optionally substituted, alkyl, alkenyl, alkynyl, aryl, arylalkyl, and alkylaryl. More preferably $R^7$ and $R^8$ are, independently from each other, H or an alkyl group, most preferably both $R^7$ and $R^8$ are H.

As far as integer q is concerned, n is preferably from 1 to 20, preferably from 1 to 15, more preferably from 1 to 10, more preferably from 1 to 5, such as 1, 2, 3, 4 or 5, more preferably 1.

If integer q is greater than 1, the groups —C($R^7R^8$)— may be the same or different from each other. Furthermore, these groups may be linked directly to each other or at least two such structure units may be separated by a heteroatom such as O or S.

According to a preferred embodiment of the present invention, groups —C($R^7R^8$)— directly linked to each other have the same constitution. Most preferably Ar thus comprises the group —($CH_2$)q- with q being from 1 to 10, preferably from 1 to 5, in particular 1.

Therefore, according to a particularly preferred embodiment of the present invention, spacer Ar comprises the group —$CH_2$—. Accordingly, in particularly preferred embodiments, W comprises the group —$CH_2$—NH—, particularly W is the group —$CH_2$—NH—. Especially, spacer 1 comprises the group —$CH_2$—NH—. According to other preferred embodiments, spacer 1 comprises the group —NH—C(=O)—$CH_2$—$CH_2$—NH—. Other preferred embodiments for spacer 1 and compound Ar are disclosed in the particular Examples herein.

According to an alternative embodiment, the spacer 1 comprises at least one structure unit —[($CR^7R^8$)$_q$—O—($CR^7R8_6$)$_r$]$_s$—, preferably —[($CH_2$)$_q$—O—($CH_2$)$_r$]$_s$— wherein q is equal to or different from r and wherein q and r are, independently of each other from 0 to 10, 0 to 10, with the proviso that when one of r and q is 0, the other one is not 0, preferably wherein r+q=2, and wherein s is from 1 to 10, preferably from 1 to 5, more preferably from 1 to 2.

Besides the functional group W and optionally the structural unit —(C($R^7R^8$))$_q$—, spacer 1 may also comprise a further bifunctional linking compound linking the functional group W to a functional group of the compound D. As regards said bifunctional linking compounds, any linking compound known to those skilled in the art suitable for coupling the functional group W to functional group of the further compound can be used.

Thus, the present invention also relates to a compound as described above, wherein Ar further comprises a spacer moiety 1 linking the optionally substituted aryl or heteroaryl moiety to the further compound D, said spacer moiety optionally comprising a bifunctional linker.

According to preferred embodiments, the spacer 1 preferably has the structure —NH—, —$CH_2$—NH—, —$CH_2$—$CH_2$—NH— or —$CH_2$—$CH_2$—$CH_2$—NH—, wherein said spacer 1 is either directly attached to compound D or via a suitable bifunctional linking compound.

Both functional groups in the bifunctional linking compound can preferably form a linking group selected from the group consisting of =N—, —N=, —Z—, —C(=Z)—NH—, —NH—C(=Z)—, —NH—C(=Z)—Z'—, —Z'—C(=Z)—NH—, —Z'—C(=Z)—, —C(=Z)—Z'—, —C(=Z), —S—S—, —S—$CH_2$—C(=O)—O, —O—C(=O)—$CH_2$—S—, —S-maleimide-, -maleimide-S—, —C=NH—O—, —O—NH=C— and 1,2,3-triazole, with Z and Z' being independently of each other selected from the group consisting of NH, O and S, preferably wherein the bifunctional linker comprises a —NH—C(=O)— group).

According to preferred embodiments, the bifunctional linking compound is derived from a linking agent selected from the group consisting of amino acids, diamines, dicarboxylic acids, aminoalcohols, hydroxocarboxylic acids, mercaptocarboxylicacids, mercaptoamines, dithiols, aminoalkynes, dialkynes, alkinocarboxylic acids, diazides, azidoamines, azidocarboxylic acids. More preferably, the bifunctional linking compound is an amino acid.

Preferred bifunctional linkers comprise a functional group capable of being coupled to the group W, preferably to a group —NH—, such as carbonyl or carboxyl groups. Most preferably the bifunctional group comprises a carboxyl group to be coupled to the functional group W and an amino group to be coupled to the compound D.

The following bifunctional linkers are preferred: —C(=O)—($CH_2$)$_u$—NH— with the integer u being from 1 to 8, preferably from 1 to 5, most preferably 2.

According to a preferred embodiment, the aromatic group is a phenyl group. Preferably said phenyl group is linked to the Linker L as well as to the further compound D, wherein the Linker L and compound D are attached to the phenyl ring, optionally via additional suitable spacer moieties, and are positioned in ortho, meta or para positions to each other, preferably in para position.

Thus, according to a preferred embodiment, Ar is a moiety comprising a para substituted phenyl group; Thus, the following structure is preferred, wherein spacer 2, spacer 1, and bifunctional linking compound are, independently of each other either present or absent, and if presented selected from the groups as described above.

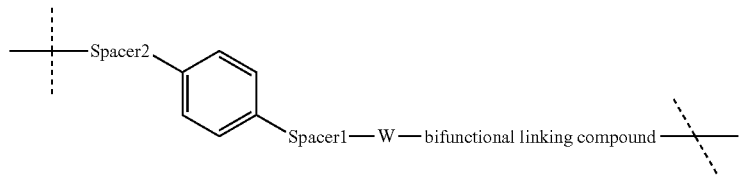

As regards the spacer moiety 2, said spacer preferably comprises a functional group Y to be linked to the functional group X. Optionally, the spacer 2 comprises, independently from spacer 1, at least one structural unit having the formula —(C($R^7R^8$))$_q$—. Reference is made to the description of group —(C($R^7R^8$))$_q$— above.

As regards the functional group Y, all conceivable groups capable of being coupled to the functional group X may be used. Reference is made to the description of group Y above. Most preferably, spacer 2 consists of the functional group Y. In particular, functional group Y comprises a group —C(=O)—. According to one preferred example, Y is derived from —C(=O)—OH. Other preferred examples for groups Ar can be taken from the particular Examples herein.

In particularly preferred embodiments of the invention the following groups are preferred for Ar:

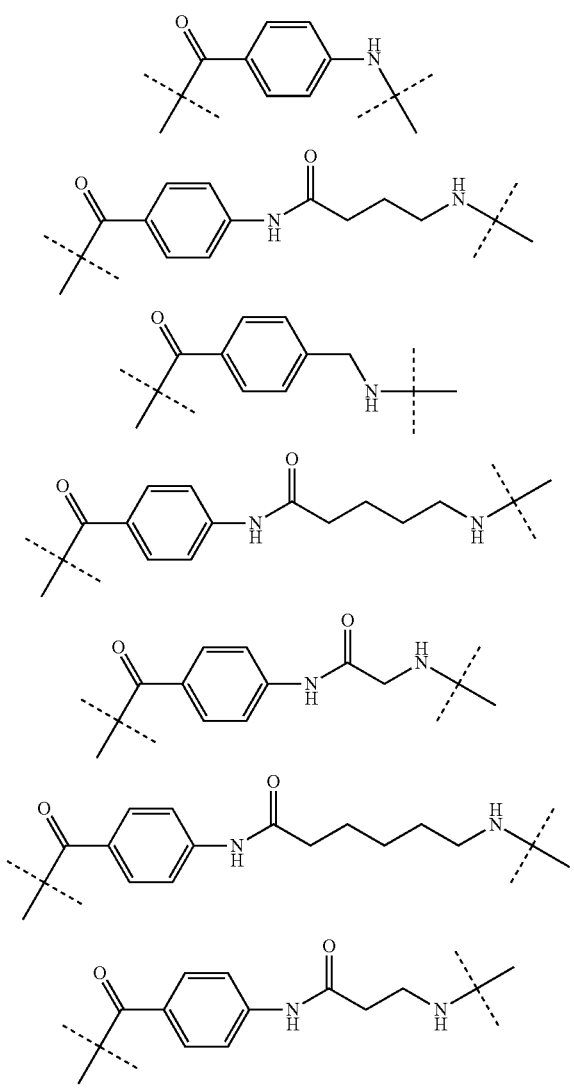

with the following group being especially preferred:

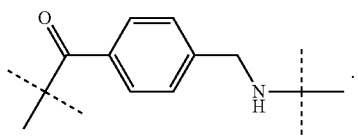

Thus, the present invention also relates to a compound as described above, wherein Ar is a group having the formula:

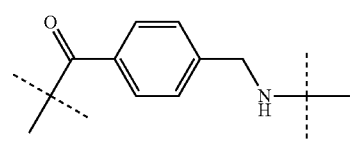

Thus, the present invention also relates to a compound having the following structure:

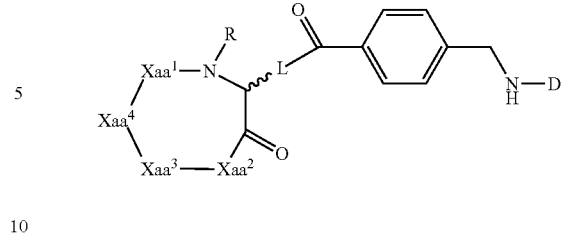

The Compound D:

The compound D may also be referred to herein as "D" or "further compound D".

In one aspect of the invention, D comprises, preferably is a combination of an organic complexation agent and a detectable label. In certain preferred embodiments, the radionuclide is a Ga radionuclide or an In radionuclide, preferably a Ga radionuclide. The combination is preferably selected from Ga with DOTA, Ga with NODASA, Ga with NODAGA, Ga with DFO or Ga with NOTA, in particular selected from Ga with DOTA. Preferably, the complexation agent being covalently bound to Ar.

In another aspect of the invention, D comprises, preferably is a detectable label, organic complexation agent or active substance. Accordingly, D may be selected from the group consisting of detectable labels, organic complexation agents and active substances. In certain preferred embodiments, D comprises, preferably is a detectable label. In certain preferred embodiments, D comprises, preferably is an organic complexation agent. In certain preferred embodiments, D comprises, preferably is an active substance. In certain embodiments of this aspect, —Ar-D, particularly -L-Ar-D, especially the compound of formula (I), does not comprise a $^{18}$F-benzoyl residue. In other embodiments of this aspect, D, particularly -L-Ar-D, especially the compound of formula (I), does not comprise $^{18}$F.

In an additional aspect of the invention, D comprises, preferably is a combination of an organic complexation agent and Ga, wherein said Ga is not a radionuclide, such as wherein Ga is any non-radioactive isotope. In an additional aspect of the invention, D comprises, preferably is a combination of an organic complexation agent and In, wherein said In is not a radionuclide, such as wherein In is any non-radioactive isotope.

In preferred embodiments of the invention, the organic complexation agent is selected from the group consisting of NODASA, NODAGA, TETA, TRITA, DTPA, EDTA, CDTA, CPTA, EGTA; HBED, TTNA, DTPA, DOTA, NOTA, HP-DOA3, CBTE2a, TE2A, TMT, DPDP, HYNIC, DFO, and HEDTA, and particularly from DOTA, NOTA, DTPA, and TETA.

In preferred embodiments of the invention the detectable label is a radionuclide selected from the group consisting of $^{11}$C, $^{18}$F, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{72}$As, $^{77}$As, $^{75}$Br, $^{76}$Br, $^{77}$Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi and $^{225}$Ac; particularly from the group consisting of $^{18}$F, $^{68}$Ga, $^{89}$Zr, $^{90}$Y, $^{99m}$Tc, $^{111}$In, $^{123}$I, $^{124}$I, $^{131}$I, $^{177}$Lu; especially from the group consisting of $^{18}$F, $^{68}$Ga, $^{99m}$Tc, $^{111}$In, $^{123}$I, and $^{177}$Lu.

"Active substances" are well-known to the skilled person. The term "active substance" as used in the context of the present invention preferably refers to substances selected from the group consisting of cytotoxic agents, lipids, sugars, sugar conjugates, sugar derivatives, proteins and combinations thereof. In certain preferred embodiment, the active substance is a cytotoxic agent. In certain embodiments, the active substance is a radionuclide, particularly a radionuclide disclosed herein. In other preferred embodiments, the active substance is selected from sugars, sugar conjugates, sugar derivatives, proteins and combinations thereof, or is a lipid.

"Cytotoxic agents", which may also be referred to herein as "cytotoxic moieties" or "cytotoxic compounds", are well known to the skilled person. They include the cytotoxic compounds disclosed hereinbelow, particularly the radionuclides disclosed hereinbelow. Also lipids, sugars, sugar conjugates, sugar derivatives, and proteins, all of which are well-known to the skilled person, are not particularly limited. Preferably, the protein is an enzyme or an antibody.

In preferred embodiments, particularly for endoradiotherapeutic purposes, compounds of the invention comprise a compound D which comprises, preferably is a radioisotope selected from the group consisting of $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{195m}$Pt, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{103m}$Rh, $^{111}$Ag, $^{124}$I, $^{131}$I, and $^{211}$Atm $^{212}$Bi, $^{225}$Ac; more preferably from the group consisting of $^{90}$Y, $^{131}$I, and $^{177}$Lu; and most preferably from the group consisting of $^{90}$Y and $^{177}$Lu.

Thus, the present invention also refers to a compound of formula (I) as described above, wherein D, comprises, preferably is, a radionuclide selected from the group consisting of $^{114m}$In, $^{186}$Re, $^{188}$Re, $^{77}$As, $^{90}$Y, $^{66}$Ga, $^{67}$Cu, $^{169}$Er, $^{117m}$Sn, $^{121}$Sn, $^{127}$Te, $^{142}$Pr, $^{143}$Pr, $^{195m}$Pt, $^{198}$Au, $^{199}$Au, $^{149}$Tb, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{103m}$Rh, $^{111}$Ag, $^{124}$I, $^{131}$I, and $^{211}$At, $^{212}$Bi, $^{225}$Ac; more preferably from the group consisting of $^{90}$Y, $^{131}$I, and $^{177}$Lu; and most preferably from the group consisting of $^{90}$Y and $^{177}$Lu.

The Term Detectable Label:

The term "detectable label" as used herein refers to any label which provides directly or indirectly a detectable signal.

For example, the label may be detectable without the addition of further reagents, such as by means of an output of detectable electromagnetic radiation or other nuclear radiation from the label itself, or as a result of its magnetic or paramagnetic properties. The label may also be detectable upon addition of one or more further reagent(s). A person skilled in the art will readily select said further reagent(s) in dependence of the label.

The detectable label is preferably a moiety being suitable for imaging and/or assaying, for example, for identifying, diagnosing, evaluating, detecting and/or quantitating, in vivo or in vitro, in particular for in vivo or in vitro detection via radioscintigraphy, magnetic resonance imaging (MRI), chemiluminescence, near infrared luminescence, gamma imaging, magnetic resonance spectroscopy, fluorescence spectroscopy, SPECT, computed tomography (CT scan), positron emission tomography (PET) or methods for optical tomography.

Suitable detectable labels include, for example, radiolabels, such as radioisotopes, radionuclides, isotopes, enzymes, enzyme substrates or co-factors, enzyme inhibitors, magnetic or paramagnetic moieties or particles, fluorescent groups, biotin (in conjunction with streptavidin complexation), radiolabels in conjugation with organic complexation agents, photoaffinity groups, or enzymes and substrates for bioluminescent imaging, such as firefly luciferase and L-luciferin as the substrate, or combinations thereof.

"Fluorescent labels" or "fluorescent groups" include, but are not limited to NBD (7-nitro-1,2,3-benzoxadiazole), Texas red, phycoerythrin (PE), Cy5, Cy 5.5, cytochrome c, and fluoresceine isothiocyanate (FITC).

"Magnetic or paramagnetic moieties or particles" include, but are not limited to MR contrast agents, e.g. chelates of paramagnetic, ferromagnetic, or diamagnetic metal ions, or magnetic particles. One specific example for a paramagnetic label is gadolinium (Gd) and chelates thereof.

According to preferred embodiments of the present invention, in case the compound of formula (I) comprises a detectable label, said detectable label is preferably a radiolabel or an organic complexation agent or a combination of a radiolabel and an organic complexation agent thereof.

In case the compound D, particularly the detectable label, comprises, preferably is a radiolabel, said radiolabel is preferably a radionuclide selected from the group consisting of $^{11}$C, $^{18}$F, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{72}$As, $^{77}$As, $^{75}$Br, $^{76}$Br, $^{77}$Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi and $^{225}$Ac; and more preferably from the group consisting of $^{18}$F, $^{68}$Ga, $^{99m}$Tc, $^{111}$In, $^{123}$I, and $^{177}$Lu. In certain embodiments of the invention, the radionucleotide is not $^{18}$F.

Thus, the present invention also refers to a compound of formula (I) as described above, wherein D comprises, preferably is, a radionuclide selected from the group consisting of $^{11}$C, $^{18}$F, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{72}$As, $^{77}$As, $^{75}$Br, $^{76}$Br, $^{77}$Br, $^{82}$Br, $^{89}$Zr, $^{90}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{120}$I, $^{123}$I, $^{124}$I, $^{125}$I, $^{131}$I, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi and $^{225}$Ac; and most preferably from the group consisting of $^{18}$F, $^{68}$Ga, $^{99m}$Tc, $^{111}$In, $^{123}$I, and $^{177}$Lu. In certain preferred embodiments, D comprises or is a Ga or In radionuclide, especially selected from $^{66}$Ga, $^{68}$Ga, $^{67}$Ga, $^{110m}$In, $^{111}$In, $^{113m}$In, and $^{114m}$In. In more preferred embodiments, D comprises or is a Ga radionuclide, such as $^{66}$Ga, $^{67}$Ga, or $^{68}$Ga, especially $^{68}$Ga.

"Radionuclide" and "radioisotope" are used interchangeably herein. A "radionuclide" as used herein may e.g. be a radiolabel or a cytotoxic moiety.

In case the compound of formula (I) comprises a radionuclide, said radionuclide is preferably complexed by an organic complexation agent, said complexation agent being attached to the moiety Ar as described above.

The Organic Complexation Agent

The term "organic complexation agent" refers to a chelating agent, preferably capable of complexing at least one radionuclide.

As regards complexation agents suitable for the present invention, reference is made to WO 2009/109332, pages 9 to 14, and the respective metal chelators disclosed therein as well as to WO 97/31657.

According to a preferred embodiment of the present invention, the organic complexation agent is a chelating agent like NODASA, NODAGA, TETA, TRITA, DTPA, EDTA, CDTA, CPTA, EGTA; HBED, TTHA, DTPA, DOTA, NOTA, HP-DOA3, CBTE2a, TE2A, TMT, DPDP, HYNIC, DFO, and HEDTA. Those chelating agents are well known to those skilled in the art for radiopharmaceuticals and radiodiagnosticals.

CBTE2a stands for bis(carboxymethyl)-1,4,8,11-tetraazabicyclo[6.6.2]hexadecane,
CDTA stands for cyclohexyl 1,2-diamine tetraacetic acid,
CPTA stand for [4-(1,4,8,11-tetraazacyclotetradec-1-yl)-methyl benzoic acid]hydrochloride,
DFO stands for N'[5-[acetyl(hydroxy)amino]pentyl]-N-[5-[[4-[5-aminopentyl(hydroxy)amino]-4-oxobutanoyl]amino]pentyl]-N-hydroxybutanediamide,
DO2A stands for 4,11-bis(carboxymethyl)-1,4,8,11-tetraazabicyclo[6.6.2]hexadecane,
DOTA stands for 1,4,7,10-tetracyclododecene-N,N',N'',N''', tetraacetic acid,
DPDP stands for (N,N'-dipyridoxylethylenediamine-N,N'-diacetate-5,5'-bis(phosphate),
DTPA stands for dietehylenetriaminepentaacetic acid,
EDTA stands for ethylenediamine-N,N'-tetraacetic acid,
EGTA stands ethyleneglycol-O,O-bis(2-aminoethyl), N,N,N',N' tetraacetic acid,
HBED stands for N,N-bis(hydroxybenzyl)-ethylenediamine-N,N'-diacetic acid,
HEDTA stands for hydroxyethylediamine triacetic acid,
HP-DOA3 stands for 1-(p-nitrobenzyl)-1,4,710-tetraazacyclodecane-4,7,10-triacetate,
HYNIC stands for 6-hydrazinyl-N-methylpyridine-3-carboxamide,
NODASA stands for 1,4,7-Triazacyclononane-1-succinic acid-4,7-diacetic acid,
NODAGA stands for 1-(1-Carboxy-3-carboxypropyl)-4,7-(carboxy)-1,4,7-triazacyclononane,
NOTA stands for 1,4,7-triazacyclononanetriacetic acid,
TE2A stands for 4,11-bis(carboxymethyl)-1,4,8,11-tetraazabicyclo[6.6.2]hexadecane,
TETA stands for 1,4,8,11-tetraazacyclododecane-1,4,8,11-tetraacetic acid,
TMT stands for terpyridine-bis(methylenaminetetraacetic acid,
TRITA stands for 1,4,7,10-tetraazacyclotridecane-N,N',N'', N'''-tetraacetic acid,
TTHA stands for triethylene tetraamine hexaacetic acid.

According to a further embodiment of the present invention, the organic complexation agent is a macrocyclic chelating agent, for example, a porphyrin-like molecule, a pentaaza-macrocycle as described by Zhang et al., 1998, a phthalocyanine, a crown ether, e.g. a nitrogen crown ether such as the sepulchrates, or crypates.

According to an alternative embodiment, the organic complexation agent is a $N_rS_{(4-r)}$ chelating agents, such as the chelating agents described on page 8 to page 9 in WO 97/31657.

Examples of suitable chelators are further described in the international patent application WO 89/07456, such as unsubstituted or substituted 2-imino-thiolanes and 2-iminothiacyclohexanes, in particular 2-imino-4-mercaptomethylthiolane.

According to a preferred embodiment of the present invention, the organic complexation agent is selected from the group consisting of DOTA, NOTA, TRITA, TETA, DTPA, HYNIC and CBTE2a, more preferably DOTA, NOTA, DTPA, and TETA.

Thus, the present invention also relates to a compound, as described above, wherein the organic complexation agent is selected from the group consisting of DOTA, NOTA, TRITA, TETA, DTPA, HYNIC and CBTE2a, more preferably DOTA, NOTA, DTPA, and TETA. More preferably, the organic complexation agent is DOTA.

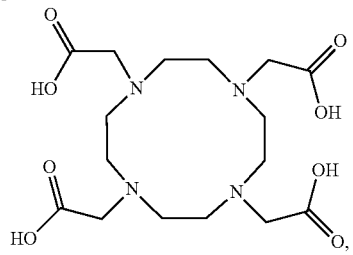 [SMILES: O=C(O)CN1CCN(CC(=O)O)CCN(CC(=O)O)CCN(CC(=O)O)CC1]

wherein DOTA is preferably coupled via one of its carboxy functions to the moiety Ar.

Thus, the present invention also relates to a compound, as described above, wherein D comprises an organic complexation agent, and wherein the organic complexation agent is selected from the group consisting of like NODASA, NODAGA, TETA, TRITA, DTPA, EDTA, CDTA, CPTA, EGTA, HBED, TTHA, DTPA, DOTA, NOTA, HP-DOA3, CBTE2a, TE2A, TMT, DPDP, HYNIC, DFO and HEDTA, in particular wherein the organic complexation agent is selected from the group consisting of DOTA, NOTA, TRITA, TETA, DTPA, HYNIC and CBTE2a, more preferably DOTA, NOTA, DTPA, and TETA, more preferably DOTA, NOTA and DTPA, most preferably DOTA.

In particularly preferred embodiments, D comprises, especially consists of a combination of an organic complexation agent and a radionuclide. Suitable such combinations are well-known to the skilled person. Preferred combinations involve Ga or In, preferably Ga. Exemplary combinations are Ga with DOTA, Ga with NODASA, Ga with NODAGA, Ga with DFO or Ga with NOTA. The combination of a Ga or In radionuclide, preferably Ga radionuclide, with DOTA is particularly preferred. Specific embodiments include $^{66}$Ga with DOTA, $^{68}$Ga with DOTA, $^{67}$Ga with DOTA, $^{110m}$In with DOTA, and $^{111}$In, DOTA; particularly $^{66}$Ga with DOTA, $^{68}$Ga with DOTA, and $^{67}$Ga with DOTA.

In particularly preferred embodiments, D comprises, in particular is, a combination of a radionuclide and a complexation agent, with the complexation agent being covalently bound to Ar and the radionuclide being complexed by the complexation agent.

In the following tables I to IV, preferred structures of the invention are mentioned by way of example, wherein the following abbreviations are used:

Structure 1:

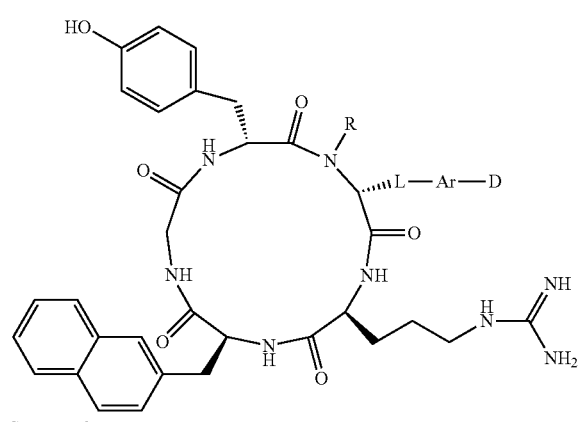

Structure 2:

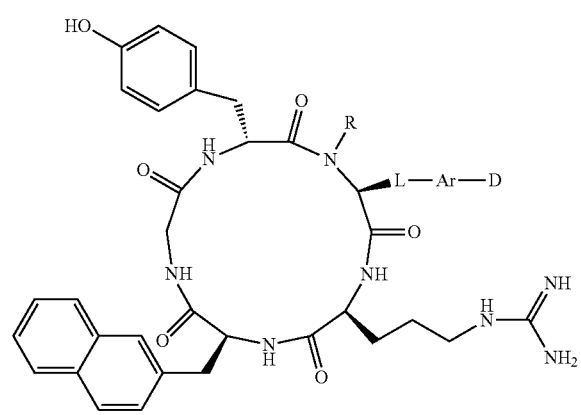

Ar-groups 1 to 6

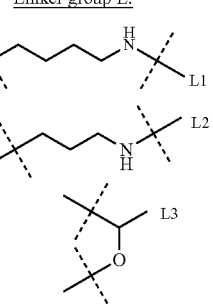

Linker group L:

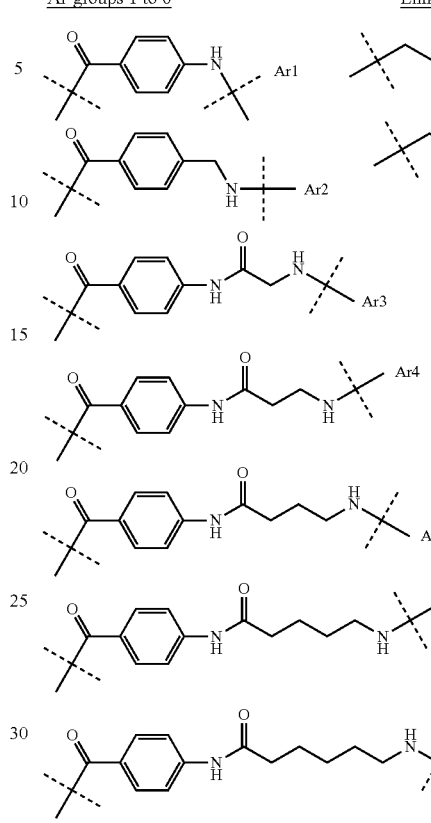

TABLE I

|   | Structure | L | Ar | R | D |
|---|---|---|---|---|---|
| 1 | Structure 1 | Selected from the group consisting of L1, L2, and L3 | Ar2 | H | DOTA |
| 2 | Structure 1 | Selected from the group consisting of L1, L2, and L3 | Ar2 | H | DOTA-Ga-complex |
| 3 | Structure 1 | Selected from the group consisting of L1, L2, and L3 | Ar2 | H | DOTA-In-complex |
| 4 | Structure 1 | Selected from the group consisting of L1, L2, and L3 | Ar1 | H | DOTA |
| 5 | Structure 1 | Selected from the group consisting of L1, L2, and L3 | Ar1 | H | DOTA-Ga-complex |
| 6 | Structure 1 | Selected from the group consisting of L1, L2, and L3 | Ar1 | H | DOTA-In-complex |
| 7 | Structure 1 | Selected from the group consisting of L1, L2, and L3 | Ar4 | H | DOTA |
| 8 | Structure 1 | Selected from the group consisting of L1, L2, and L3 | Ar4 | H | DOTA-Ga-complex |
| 9 | Structure 1 | Selected from the group consisting of L1, L2, and L3 | Ar4 | H | DOTA-In-complex |
| 10 | Structure 1 | L1 | Selected from the group consisting of Ar1, Ar2, Ar3, Ar4, Ar5 and Ar6 | H | DOTA |
| 11 | Structure 1 | L1 | Selected from the group consisting of Ar1, Ar2, Ar3, Ar4, Ar5 and Ar6 | H | DOTA-Ga-complex |
| 12 | Structure 1 | L1 | Selected from the group consisting of Ar1, Ar2, Ar3, Ar4, Ar5 and Ar6 | H | DOTA-In-complex |
| 13 | Structure 1 | L2 | Selected from the group consisting of Ar1, Ar2, Ar3, Ar4, Ar5 and Ar6 | H | DOTA |
| 14 | Structure 1 | L2 | Selected from the group consisting of Ar1, Ar2, Ar3, Ar4, Ar5 and Ar6 | H | DOTA-Ga-complex |

TABLE I-continued

| | Structure | L | Ar | R | D |
|---|---|---|---|---|---|
| 15 | Structure 1 | L2 | Selected from the group consisting of Ar1, Ar2, Ar3, Ar4, Ar5 and Ar6 | H | DOTA-In-complex |

TABLE II

| | Structure | L | Ar | R | D |
|---|---|---|---|---|---|
| 1 | Structure 1 | Selected from the group consisting of L1, L2, and L3 | Ar2 | Me | DOTA |
| 2 | Structure 1 | Selected from the group consisting of L1, L2, and L3 | Ar2 | Me | DOTA-Ga-complex |
| 3 | Structure 1 | Selected from the group consisting of L1, L2, and L3 | Ar2 | Me | DOTA-In-complex |
| 4 | Structure 1 | Selected from the group consisting of L1, L2, and L3 | Ar1 | Me | DOTA |
| 5 | Structure 1 | Selected from the group consisting of L1, L2, and L3 | Ar1 | Me | DOTA-Ga-complex |
| 6 | Structure 1 | Selected from the group consisting of L1, L2, and L3 | Ar1 | Me | DOTA-In-complex |
| 7 | Structure 1 | Selected from the group consisting of L1, L2, and L3 | Ar4 | Me | DOTA |
| 8 | Structure 1 | Selected from the group consisting of L1, L2, and L3 | Ar4 | Me | DOTA-Ga-complex |
| 9 | Structure 1 | Selected from the group consisting of L1, L2, and L3 | Ar4 | Me | DOTA-In-complex |
| 10 | Structure 1 | L1 | Selected from the group consisting of Ar1, Ar2, Ar3, Ar4, Ar5 and Ar6 | Me | DOTA |
| 11 | Structure 1 | L1 | Selected from the group consisting of Ar1, Ar2, Ar3, Ar4, Ar5 and Ar6 | Me | DOTA-Ga-complex |
| 12 | Structure 1 | L1 | Selected from the group consisting of Ar1, Ar2, Ar3, Ar4, Ar5 and Ar6 | Me | DOTA-In-complex |
| 13 | Structure 1 | L2 | Selected from the group consisting of Ar1, Ar2, Ar3, Ar4, Ar5 and Ar6 | Me | DOTA |
| 14 | Structure 1 | L2 | Selected from the group consisting of Ar1, Ar2, Ar3, Ar4, Ar5 and Ar6 | Me | DOTA-Ga-complex |
| 15 | Structure 1 | L2 | Selected from the group consisting of Ar1, Ar2, Ar3, Ar4, Ar5 and Ar6 | Me | DOTA-In-complex |

TABLE III

| | Structure | L | Ar | R | D |
|---|---|---|---|---|---|
| 1 | Structure 2 | Selected from the group consisting of L1, L2, and L3 | Ar2 | H | DOTA |
| 2 | Structure 2 | Selected from the group consisting of L1, L2, and L3 | Ar2 | H | DOTA-Ga-complex |
| 3 | Structure 2 | Selected from the group consisting of L1, L2, and L3 | Ar2 | H | DOTA-In-complex |
| 4 | Structure 2 | Selected from the group consisting of L1, L2, and L3 | Ar1 | H | DOTA |
| 5 | Structure 2 | Selected from the group consisting of L1, L2, and L3 | Ar1 | H | DOTA-Ga-complex |
| 6 | Structure 2 | Selected from the group consisting of L1, L2, and L3 | Ar1 | H | DOTA-In-complex |
| 7 | Structure 2 | Selected from the group consisting of L1, L2, and L3 | Ar4 | H | DOTA |
| 8 | Structure 2 | Selected from the group consisting of L1, L2, and L3 | Ar4 | H | DOTA-Ga-complex |
| 9 | Structure 2 | Selected from the group consisting of L1, L2, and L3 | Ar4 | H | DOTA-In-complex |
| 10 | Structure 2 | L1 | Selected from the group consisting of Ar1, Ar2, Ar3, Ar4, Ar5 and Ar6 | H | DOTA |

TABLE III-continued

| | Structure | L | Ar | R | D |
|---|---|---|---|---|---|
| 11 | Structure 2 | L1 | Selected from the group consisting of Ar1, Ar2, Ar3, Ar4, Ar5 and Ar6 | H | DOTA-Ga-complex |
| 12 | Structure 2 | L1 | Selected from the group consisting of Ar1, Ar2, Ar3, Ar4, Ar5 and Ar6 | H | DOTA-In-complex |
| 13 | Structure 2 | L2 | Selected from the group consisting of Ar1, Ar2, Ar3, Ar4, Ar5 and Ar6 | H | DOTA |
| 14 | Structure 2 | L2 | Selected from the group consisting of Ar1, Ar2, Ar3, Ar4, Ar5 and Ar6 | H | DOTA-Ga-complex |
| 15 | Structure 2 | L2 | Selected from the group consisting of Ar1, Ar2, Ar3, Ar4, Ar5 and Ar6 | H | DOTA-In-complex |

TABLE IV

| | Structure | L | Ar | R | D |
|---|---|---|---|---|---|
| 1 | Structure 2 | Selected from the group consisting of L1, L2, and L3 | Ar2 | Me | DOTA |
| 2 | Structure 2 | Selected from the group consisting of L1, L2, and L3 | Ar2 | Me | DOTA-Ga-complex |
| 3 | Structure 2 | Selected from the group consisting of L1, L2, and L3 | Ar2 | Me | DOTA-In-complex |
| 4 | Structure 2 | Selected from the group consisting of L1, L2, and L3 | Ar1 | Me | DOTA |
| 5 | Structure 2 | Selected from the group consisting of L1, L2, and L3 | Ar1 | Me | DOTA-Ga-complex |
| 6 | Structure 2 | Selected from the group consisting of L1, L2, and L3 | Ar1 | Me | DOTA-In-complex |
| 7 | Structure 2 | Selected from the group consisting of L1, L2, and L3 | Ar4 | Me | DOTA |
| 8 | Structure 2 | Selected from the group consisting of L1, L2, and L3 | Ar4 | Me | DOTA-Ga-complex |
| 9 | Structure 2 | Selected from the group consisting of L1, L2, and L3 | Ar4 | Me | DOTA-In-complex |
| 10 | Structure 2 | L1 | Selected from the group consisting of Ar1, Ar2, Ar3, Ar4, Ar5 and Ar6 | Me | DOTA |
| 11 | Structure 2 | L1 | Selected from the group consisting of Ar1, Ar2, Ar3, Ar4, Ar5 and Ar6 | Me | DOTA-Ga-complex |
| 12 | Structure 2 | L1 | Selected from the group consisting of Ar1, Ar2, Ar3, Ar4, Ar5 and Ar6 | Me | DOTA-In-complex |
| 13 | Structure 2 | L2 | Selected from the group consisting of Ar1, Ar2, Ar3, Ar4, Ar5 and Ar6 | Me | DOTA |
| 14 | Structure 2 | L2 | Selected from the group consisting of Ar1, Ar2, Ar3, Ar4, Ar5 and Ar6 | Me | DOTA-Ga-complex |
| 15 | Structure 2 | L2 | Selected from the group consisting of Ar1, Ar2, Ar3, Ar4, Ar5 and Ar6 | Me | DOTA-In-complex |

Particularly preferred compounds of the present invention are selected from the group of compounds consisting of yorn'(ABS, betaAla, DOTA)RNalG yorn'(ABS, Ahx, DOTA, In)RNalG, yorn'(ABS, Ahx, DOTA, Ga)RNalG, yorn'(ABS, betaAla, DOTA, In)RNalG, yorn'(ABS, betaAla, DOTA, Ga)RNalG ("CPCR4-1"), yorn'(ABS, AVS, DOTA, In)RNalG, yorn'(ABS, AVS, DOTA, Ga)RNalG, yorn'(AMBS, DOTA, In)RNalG, yorn'(AMBS, DOTA, Ga)RNalG ("CPCR4-2"), yorn'(ABS, G, DOTA)RNalG, yorn'(ABS, G, DOTA, In)RNalG, orn'(ABS, O, DOTA, Ga)RNalG, and yorn'(ABS, DOTA, Ga)RNalG (for abbreviations: see below).

Particularly preferred compounds of the present invention are selected from the group consisting of yorn'(ABS, DOTA) RNalG, yorn'(ABS, DOTA, In)RNalG, yorn'(ABS, DOTA, Ga)RNalG, yorn'(AMBS, DOTA)RNalG, yorn'(AMBS, DOTA, In)RNalG, yorn'(AMBS, DOTA, Ga)RNalG ("CPCR4-2"), yorn'(ABS, G, DOTA)RNalG, yorn'(ABS, G, DOTA, In)RNalG, yorn'(ABS, G, DOTA, Ga)RNalG, yorn' (ABS, betaAla, DOTA)RNalG, yorn'(ABS, betaAla, DOTA, In)RNalG, yorn'(ABS, betaAla, DOTA, Ga)RNalG ("CPCR4-1"), yorn'(ABS, AVS, DOTA)RNalG, yorn'(ABS, AVS, DOTA, In)RNalG, yorn'(ABS, AVS, DOTA, Ga)RNalG, yorn'(ABS, Ahx, DOTA)RNalG, yorn'(ABS, Ahx, DOTA, In)RNalG, yorn'(ABS, Ahx, DOTA, Ga)RNalG (for abbreviations: see below).

Particularly preferred examples include yorn'(ABS, betaAla, DOTA, Ga)RNalG ("CPCR4-1"), yorn'(ABS, AVS, DOTA, Ga)RNalG, yorn'(AMBS, DOTA, Ga)RNalG ("CPCR4-2") and yorn'(ABS, DOTA, Ga)RNalG.

Among those, each of yorn'(ABS, betaAla, DOTA, Ga)R-NalG ("CPCR4-1") and yorn'(AMBS, DOTA, Ga)RNalG ("CPCR4-2") is especially preferred.

Pharmaceutically Acceptable Salt

As described above, the compound of the present invention can be formulated as pharmaceutically acceptable salt. Typical pharmaceutically acceptable salts include those salts prepared by reaction of the compounds of the present invention with a pharmaceutically acceptable mineral or organic acid or an organic or inorganic base. Such salts are known as acid addition and base addition salts. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, .gamma.hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid. Salts of amine groups may also comprise quarternary ammonium salts in which the amino nitrogen carries a suitable organic group such as an alkyl, alkenyl, alkynyl, or aralkyl moiety. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. It should be recognized that the particular counterion forming a part of any salt of this invention is usually not of a critical nature, so long as the salt as a whole is pharmacologically acceptable and as long as the counterion does not contribute undesired qualities to the salt as a whole. The term acceptable salt encompasses also pharmaceutically acceptable solvates of the compounds of the invention, wherein the compound combines with a solvent such as water, methanol, ethanol or acetonitrile to form a pharmaceutically acceptable solvate such as the corresponding hydrate, methanolate, ethanolate or acetonitrilate.

In an even further aspect, the present invention relates to a compound, or a pharmaceutically acceptable salt thereof, having a structure according to formula (II)

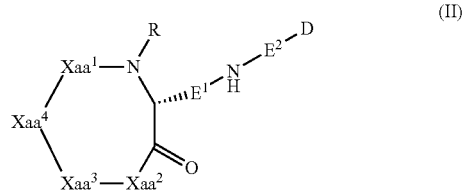

(II)

wherein $Xaa^1$ to $Xaa^4$ are independently of each other, an optionally N-alkylated natural or unnatural amino acid, R is H or methyl, $E^1$ is —$(CH_2)_e$— with e being selected from 1, 2 and 3, particularly 3, $E^2$ is a spacing moiety composed of 0 to 20 units of bifunctional linkers, and D comprises, preferably is i) a combination of an organic complexation agent and a detectable label;

or ii) a detectable label, an organic complexation agent or an active substance, said active substance particularly being selected from cytotoxic agents, lipids, sugars, sugar conjugates, sugar derivatives, proteins and combinations thereof, with the proviso that $-E^1-NH-E^2-D$ does not comprise a $^{18}F$-benzoyl residue.

Said 0 to 20 bifunctional linkers may be arranged in any conceivable order, as long as they together form a spacing moiety that is capable of linking —NH— to D.

According to this aspect, each of $Xaa^1$ to $Xaa^4$, R, D, and preferably also the bifunctional linker, as well as their respective preferred embodiments, are as defined herein above and below. Moreover, according to this aspect, D is preferably selected from DOTA and a combination of DOTA and a radionuclide.

Preferably, $E^2$ is selected from —(C=O)—$CH_2$—NH—, —(C=O)—$(CH_2)_2$—NH—, —(C=O)—$(CH_2)_3$—NH—, —(C=O)—$(CH_2)_4$—NH—C(=O)—$(CH_2)_4$—NH—, —C(=O)—$CH_2$—O—$(CH_2)_2$—O—$(CH_2)_2$—NH— and —(C=O)—$CH_2$—NH—C(=O)—$CH_2$—O—$(CH_2)_2$—O—$(CH_2)_2$—NH—, particularly selected from —(C=O)—$(CH_2)_4$—NH—C(=O)—$(CH_2)_4$—NH— and —(C=O)—$CH_2$—NH—C(=O)—$CH_2$—O—$(CH_2)_2$—O—$(CH_2)_2$—NH.

More preferably, $E^1$ is —$(CH_2)_3$— and $E^2$ is selected from —(C=O)—$(CH_2)_4$—NH—C(=O)—$(CH_2)_4$—NH— and —(C=O)—$CH_2$—NH—C(=O)—$CH_2$—O—$(CH_2)_2$—O—$(CH_2)_2$—NH—. Preferred groups -E'—NH— $E^2$- are also disclosed in the particular Examples herein.

In particular embodiments, -$E^1$-NH-$E^2$- differs from a respective linking moiety disclosed in WO 07096662 A2.

Preferably, said compound has a structure according to formula (II'):

(II')

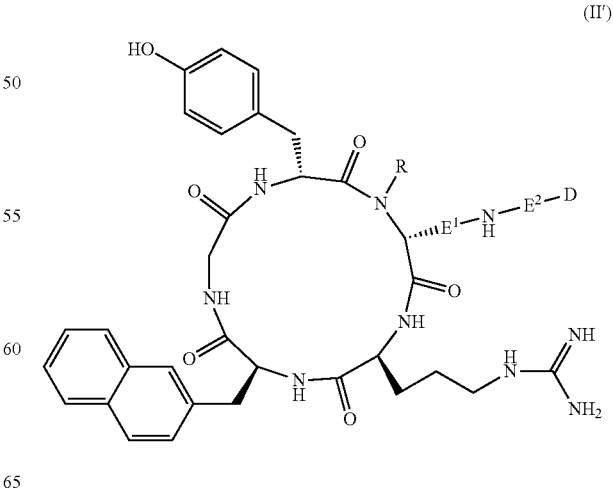

In preferred embodiments of this aspect, said compound has a structure according to a formula selected from i)
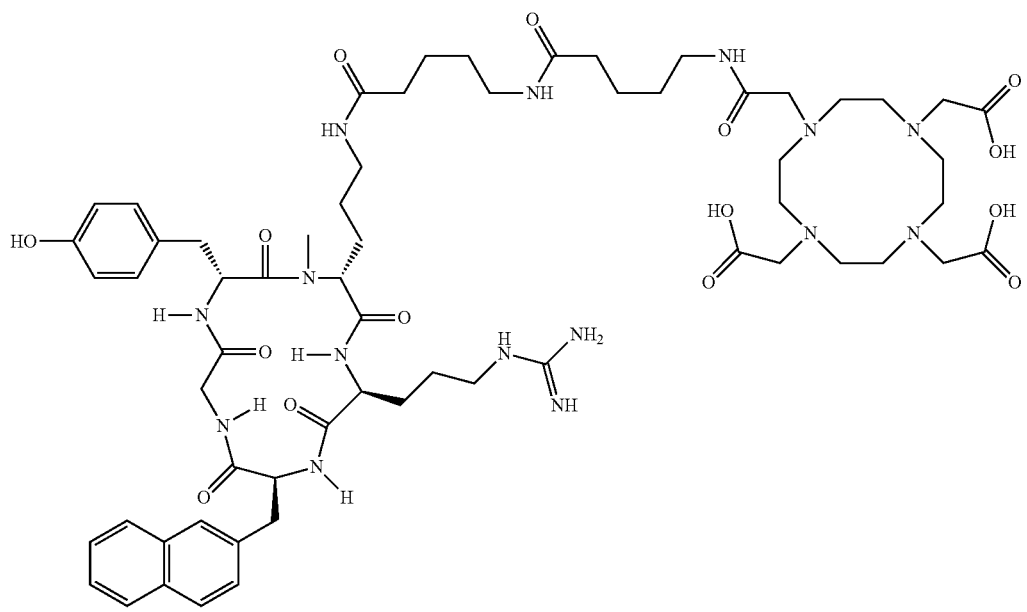
ii)
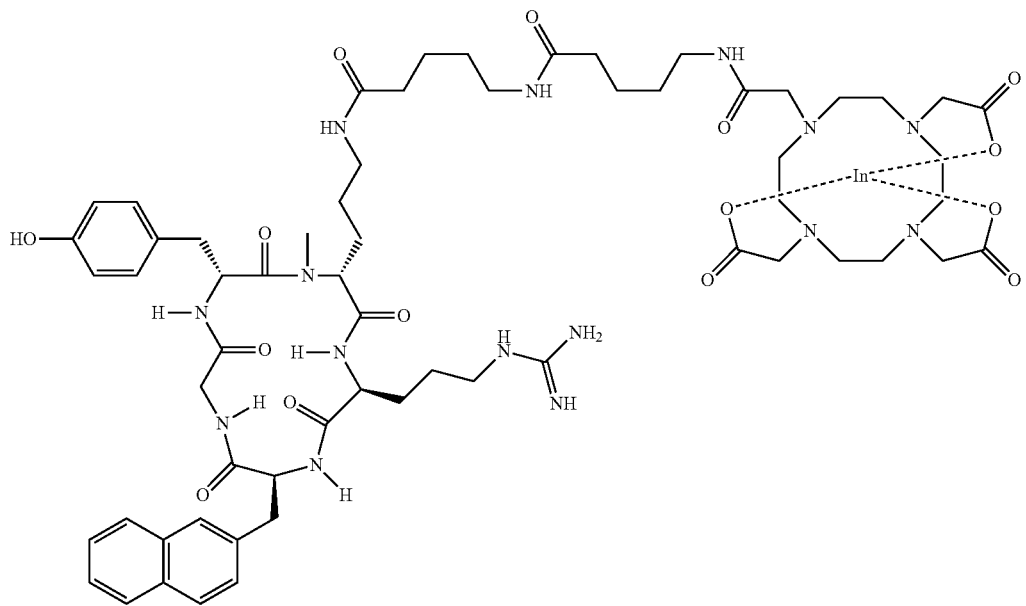

-continued
iii)
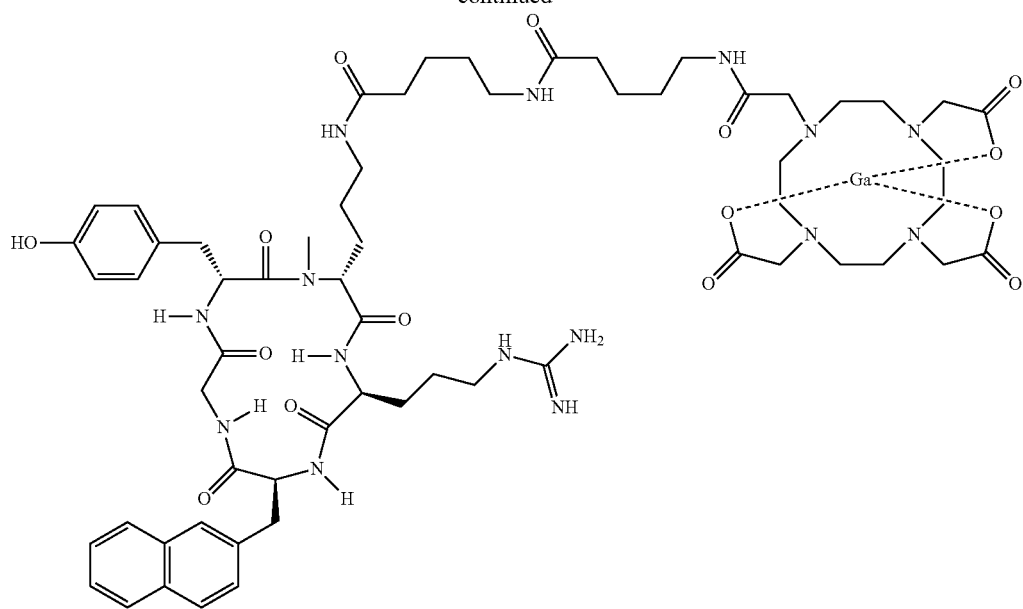
iv)
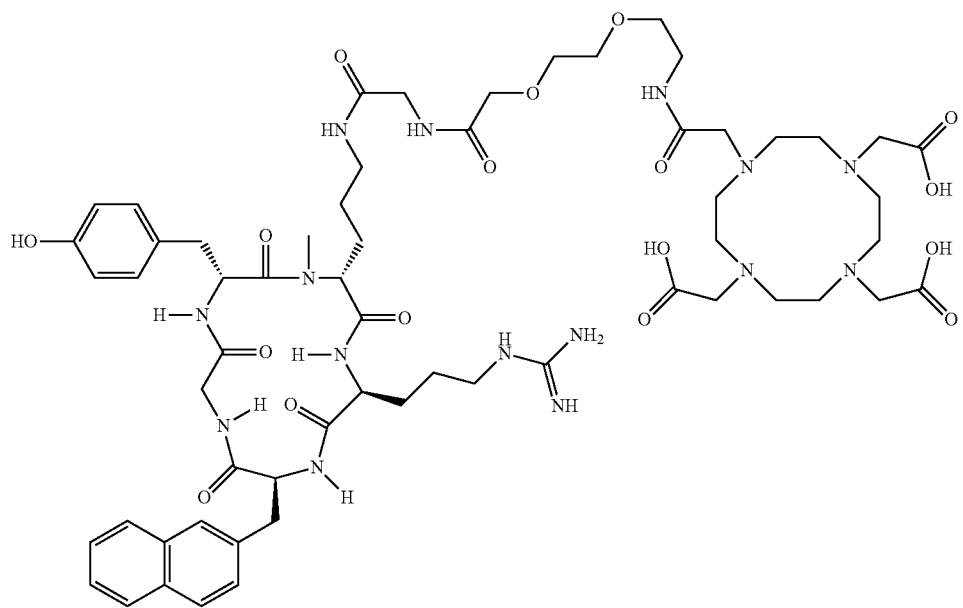

v)

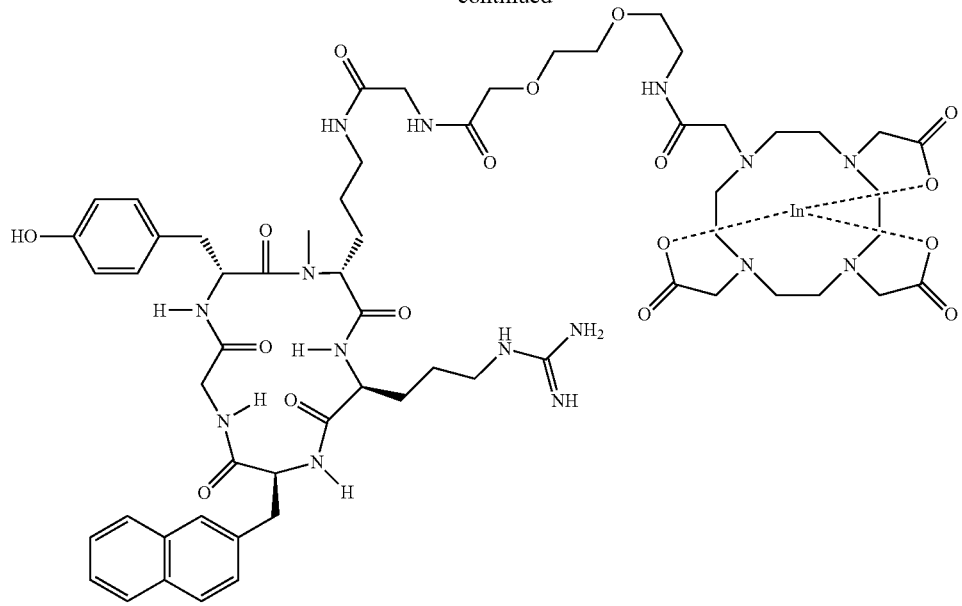

vi)

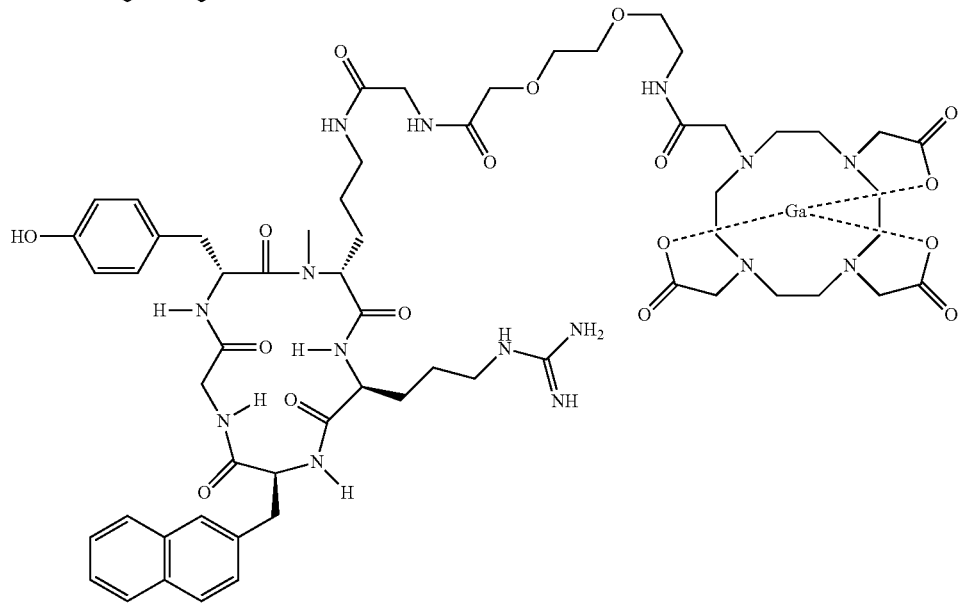

In a further aspect, the present invention relates to a pharmaceutical composition comprising a compound of the invention and at least one pharmaceutically acceptable excipient.

"Pharmaceutically acceptable excipients" are well known in the art as substances other than the active ingredients that may be part of pharmaceutical compositions. Examples for excipients include, but are not limited to one or more carriers, coatings, disintegrants, binders, fillers, diluents, lubricants, stabilizers, surfactants, preservatives, flavouring agents, colouring agents, sorbents, sweeteners, and any combinations thereof.

The pharmaceutical composition may also comprise one or more additional active ingredients known to the skilled person to provide a combination therapy, such as of a disease or disorder described herein.

An exemplary dosage of the compound of the invention may be in the range from about 0.01 to about 1000 mg, such as from about 0.05 to about 500 mg, such as from about 0.1 to about 100 mg, such as from about 0.2 to about 10 mg per kg body weight per day. As used herein, "about" refers to a range around a given value plus/minus 10% thereof. Accordingly, about 10 mg per kg body weight per day refers to 9 to 11 mg per kg body weight per day.

It will be understood that a person skilled in the art can readily determine suitable dosages and administration schemes on the basis of his knowledge, wherein preferred dosages and administration schemes will depend on the condition to be treated.

The pharmaceutical compositions of the invention may be administered by routine methods, for example via oral/peroral, parenteral (preferably intravenous, e.g. by injection), intraperitoneal, intradermal, transdermal, inhalational, topical, nasal, buccal, rectal or vaginal administration routes or via an implanted reservoir. Suitable dosage forms include, but are not limited to capsules, tablets, pellets, aqueous suspensions, aqueous solutions, aerosols, suppositories, creams, gels, ointments and transdermal patches. According to a preferred embodiment, the pharmaceutical composition is administered intravenously. Preferred embodiments involve injection. Other preferred embodiments involve infusion. According to another preferred embodiment, the pharmaceutical composition is administered perorally. Other preferred embodiments involve subcutaneous depots.

The compounds of the invention, which are believed to bind the CXCR4 receptor with high affinity, may be suitable for blocking, disrupting or otherwise interfering with the interaction between the CXCR4 receptor and its natural ligand. Likewise, they may be suitable for targeting cytotoxic moieties or the like to CXCR4 receptors.

Therefore, the compounds and compositions of the invention may be used in methods of treating CXCR4 receptor-related conditions, disorders and diseases.

Accordingly, in a further aspect, the present invention relates to a compound as defined above for use as a medicament.

In a further aspect, the present invention relates to a compound as defined above or composition as defined above for use in a method for the prevention or treatment of a CXCR4 receptor-related disease or disorder.

In addition, the invention relates to the use of a compound as defined above or composition as defined above for the manufacture of a medicament for preventing a CXCR4 receptor-related disease or disorder, as well as to the use of a compound or composition as defined above for the manufacture of a medicament for treating a CXCR4 receptor-related disease or disorder.

In addition, the invention relates to a method of preventing a CXCR4 receptor-related disease or disorder, the method comprising a step of administering a compound as defined above or composition as defined above to a subject in need thereof, as well as to a method of treating a CXCR4 receptor-related disease or disorder, the method comprising a step of administering a compound as defined above or composition as defined above to a subject in need thereof.

"CXCR4" or "CXCR4 receptor" as used herein, refers to a particular receptor, the CXC chemokine receptor 4, which well-known to the skilled person, and which is also called "fusin". It is e.g. expressed on many stem cells, but also in numerous cancers.

Term "CXCR4" or "CXCR4 receptor" as used herein also includes variants thereof. Variants particularly include isoforms encoded by alternative transcriptional splice variants, as well as mutated or truncated forms of said receptor. Preferably the gene or protein sequences of a variant CXCR4 has at least 10%, 20%, 30%, 40%, 50%, 60%, 70%, particularly at least 80% or 90%, more particularly at least 95% or 97%, especially at least 99% sequence identity to a native sequence of CXCR4. As used herein, a gene or protein is said to have "X % sequence identity" to a given sequence if upon an alignment with the best matching sequence of said given sequence the number of matching nucleotides or amino acids, respectively, divided by the number of nucleotides or amino acids of the shorter sequence multiplied by 100 is X. Methods and tools of aligning sequences are well known to the skilled person.

Mutations of a CXCR4 encoding sequence leading to truncated forms of the CXCR4 receptor may e.g. influence the extent of an inflammatory reaction or the metastatic potential of a cancer. Besides, mutations in the CXCR4 gene have been shown to be associated with e.g. WHIM (warts, hypogammaglobulinemia, infections, and myelokathexis) syndrome.

A "CXCR4 receptor-related disease or disorder" as used herein includes any pathological condition, a disease or a disorder, which is directly or indirectly related to the CXCR4 receptor per se or to its function, such as to the interaction of the CXCR4 receptor with its natural ligand CXCL12 (SDF-1). CXCR4 receptor-related disease or disorder particularly includes any disease or disorder that is related directly, indirectly, immediately and/or not immediately to the CXCR4 receptor, the CXCR4 receptor status or CXCR4 receptor signaling. Numerous CXCR4 receptor-related diseases or disorders are known in the art (cf. e.g. Taniuchi et al., 2005; Kim et al., 2005; Phillips et al., 2003).

As to the prevention or treatment of a CXCR4 receptor-related disease or disorder, said CXCR4 receptor-related disease or disorder e.g. also includes any disease or disorder involving cells expressing the CXCR4 receptor, such as cancer cells. It may also be a disease or disorder caused or promoted by a cellular pathway such as a signaling pathway involving the CXCR4 receptor. It may also be a disease or disorder caused or promoted by an altered expression such as an overexpression of the CXCR4 receptor and/or by a modification of the CXCR4 receptor.

Particularly as to aspects of the invention that involve imaging or monitoring of CXCR4 receptors, a CXCR4 receptor-related disease or disorder may be any disease or disorder involving any alteration in the status of the CXCR4 receptor, e.g. an altered expression such as an overexpression or decreased expression of the CXCR4 receptor. Likewise, also any CXCR4 receptor-related disease or disorder is envisaged, the therapy or treatment of which is directly or indirectly related to an alteration in the status of the CXCR4 receptor, e.g. an altered expression such as an overexpression or decreased expression of the CXCR4 receptor.

As one non-limiting example in this respect, reference is made to Her2/neu expression in mammacarcinoma, where Her2/neu stabilizes the CXCR4 receptor status, and where an antibody therapy towards Her2/neu leads to a destabilization the CXCR4 receptor status and finally a decreased CXCR4 expression.

As referred to herein, the CXCR4 receptor-related disease or disorder may be a neoplastic condition, an immune disease, an autoimmune disease, a vascular disease, an inflammatory condition and/or a neurological disease.

A "neoplastic condition" as used herein refers to a condition characterized by an increase in mass of a tissue resulting in a neoplasm. Said neoplasm results from a neoplasia, i.e. the proliferation of cells. Preferably, according to the invention, such neoplastic condition relates to an abnormal mass of a tissue, such as a tumor, particularly a malignant tumor. Accordingly, in a preferred embodiment the neoplastic condition is a cancer.

"Immune diseases" are diseases involving a dysfunction of the immune system, such as by an overactive or insufficiently active immune system, which diseases may be congenital or acquired and may affect various components of the immune system.

"Autoimmune diseases" are particular immune diseases, which are known within the art as diseases arising from an overly active immune response of the body against substances and tissues that are normally present in the body. They include, but are not limited to multiple sclerosis (MS), lupus erythematosus, Sjögren's syndrome, ulcerative colitis and rheumatoid arthritis.

"Vascular diseases" are known to the skilled person as diseases primarily affecting the blood vessels. They include e.g. atherosclerosis, hypertonic diseases and thrombosis. Vascular diseases may involve an inadequate ratio of oxygen need to oxygen supply.

"Inflammatory conditions" as used herein comprise diseases or disorders associated with inflammation which include, but are not limited to atherosclerosis, rheumatoid arthritis, vasculitis and asthma. Preferably, the inflammatory condition is a vascular inflammatory condition such as atherosclerosis or a disease related to atherosclerosis such as coronary heart disease (CHD).

"Neurological diseases" include diseases and disorders that can affect the central nervous system, the peripheral nervous system, or the autonomic nervous system. They include but are not limited to multiple sclerosis (MS) and Alzheimer's disease.

In a preferred embodiment of the invention, the CXCR4 receptor-related disease or disorder is any one selected from HIV infection, cancer, rheumatoid arthritis, multiple sclerosis, atherosclerosis and asthma. In one particular embodiment, the CXCR4 receptor-related disease or disorder is atherosclerosis. In another particular embodiment, the CXCR4 receptor-related disease or disorder is a leukaemia, particularly chronic lymphocytic B-cell leukaemia (B-CLL). In another particular embodiment, the CXCR4 receptor-related disease or disorder is pain or involves pain.

In another embodiment of the invention, the CXCR4 receptor-related disease or disorder is selected from any of the diseases and disorders referred to on pages 49 to 58 of WO2008/08854A, which is specifically incorporated herein by reference.

According to a particular preferred embodiment, the CXCR4 receptor-related disease or disorder is a cancer. The term "cancer" as used herein particularly includes carcinomas, sarcomas, melanomas, blastomas and lymphomas. The term "cancer" may refer to a cancer not including metastases, a cancer including metastases, or to cancer metastases. Hence, it may refer to primary tumors with or without at least one metastasis, or solely refer to cancer metastasis/metastases. Preferably, the cancer and/or cancer metastases expresses the CXCR4 receptor. Accordingly, "cancer metastasis" or "cancer metastases" per se is/are another preferred example for a CXCR4 receptor-related disease or disorder.

In one embodiment of the invention, the cancer is selected from the group consisting of astrocytoma, B-cell lymphoma, breast adenocarcinoma, breast carcinoma, cervical adenocarcinoma, colon adenocarcinoma, colorectal adenocarcinoma, colorectal carcinoma, glioblastoma, hepatocellular carcinoma, hepatoma and pancreatic carcinoma, leukaemia, large cell lung cancer, lung adenocarcinoma, lung carcinoma, lung mesothelioma, lung squamous cell carcinoma, melanoma, neuroblastoma, non small cell and small cell lung cancer (NSCLC and SCLC), ovarian adenocarcinoma, pancreatic adenocarcinoma, pancreatic carcinoma, prostate adenocarcinoma, prostate carcinoma, rectal adenocarcinoma, and renal cell adenocarcinoma.

In another embodiment, the cancer is selected from the group consisting of breast adenocarcinomas, Burkitt's B-cell lymphoma, cervical adenocarcinomas, colon and rectal adenocarcinomas, oesophageal cancer, gliomas, glioblastomas, hepatocellular carcinomas (malignant hepatomas), hepatomas, leukaemia, mamma-carcinomas, melanoma, neuroblastoma, nasopharyngeal adenocarcinoma, non small cell lung cancer (NSCLC), pancreatic adenocarcinomas, prostate cancer, small cell lung cancer (SCLC), T-cell lymphoma, and thyroid cancer.

In a preferred embodiment, the cancer is selected from the group consisting of breast adenocarcinoma, colorectal adenocarcinoma, lymphoma, melanoma carcinoma, prostate carcinoma, prostate adenocarcinoma, small cell lung cancer.

The CXCR4 receptor-related diseases and disorders described herein may be treated by a compound of the invention by administering it to a subject in need thereof. The compound may be administered in form of a pharmaceutical composition as described hereinabove. It may be administered by any known administration route including the ones described hereinabove. In a preferred embodiment, the compound is formulated as pharmaceutically acceptable salt as described hereinabove.

A "subject" as used herein may be an animal or human subject. In preferred embodiments, the subject is a mammalian subject, more preferably a human subject. In one embodiment, the subject is a human subject having a neoplasia such as a cancer or suspected of having a neoplasia such as a cancer, wherein the cancer may or may not involve metastases.

Without the intention of being bound by theory, the present inventors consider that cancer metastasis may be caused by circulating cancer cells expressing CXCR4 that are targeted to sites that attract CXCR4-expressing cells such as stem cells, e.g. to the lungs, liver and bone marrow. CXCR4 overexpression has been shown on numerous tumors. CXCR4 expression on cancer cells may particularly be increased under hypoxic conditions. Accordingly, in a particular embodiment, the invention relates to a compound of the invention for use in reducing, preferably preventing, cancer metastases. In another embodiment, the invention relates to a method of reducing, preferably preventing metastases, the method comprising administering a compound of the present invention to a subject in need thereof, particularly a subject having cancer or suspecting of having cancer.

When used in preventing or treating a CXCR4 receptor-related disease or disorder such as a cancer, the compounds of the invention may or may not include one or more cytotoxic moieties. In one embodiment, the compounds include one or more cytotoxic moieties for targeted chemotherapy of CXCR4-positive tumors, such as CXCR4-expressing cancer.

Examples for "cytotoxic moieties" are well-known within the art and include radionuclides as described herein and chemotherapeutical agents. Chemotherapeutical agents include, but are not limited to bleomycin, carboplatin, cisplatin, cyclophosphamide, chlorambucil, docetaxel, doxorubicin, etoposide, methotrexate, mitoxantrone, paclitaxel, prednisone, teniposide, valrubicin, vinblastine, vincristine, vindesine, vinorelbine. Preferred cytotoxic moieties may be selected from any of those cytotoxic compounds generally used for chemotherapy of the tumor concerned.

In addition, the compounds of the invention, which are thought to bind the CXCR4 receptor with high affinity, may be particularly suitable for use in any type of imaging applications and/or any applications involving the labelling of CXCR4 receptor(s).

Accordingly, in a further aspect, the invention relates to the use of a compound as defined above, wherein the compound comprises a detectable label, for the imaging of CXCR4 receptors, in particular for medical imaging, especially for diagnostic imaging.

The imaging may be any one of in vivo-imaging, ex vivo-imaging, and in vitro-imaging.

Likewise, in another aspect, the invention relates to a method of imaging CXCR4 receptors, in particular of medical imaging, especially of diagnostic imaging, the method comprising administering a compound as defined above or composition as defined above to a sample or a subject, wherein the compound comprises a detectable label.

Said method may be any one of an in vivo-method, an ex vivo-method, and an in vitro-method. Preferably, said method is neither a method for treatment of the human or animal body by surgery or therapy nor a diagnostic method practiced on the human or animal body. Generally, in certain embodiments, a method of the invention does not comprise, preferably is not, a method for treatment of the human or animal body by surgery or therapy or a diagnostic method practiced on the human or animal body.

"Imaging" is well known to the skilled person. Non-limiting suitable imaging techniques and methods are e.g. described in Weissleder R et al, 2008, Shah K et al, 2005, Weissleder R et al, 2003 and Kuehl H et al, 2007.

As used herein, imaging preferably relates to "biological imaging" and/or "molecular imaging", particularly to "medical imaging", and especially to "diagnostic imaging".

"Biological imaging" as used herein generally refers to any imaging used in biology or medicine, particularly to imaging for examining biological material such as a biological sample or a biological subject or part thereof.

"Molecular imaging" is well known in the art (cf. e.g. Shah K et al, 2005) and includes imaging any type of molecular and/or cellular processes, e.g. with the aim of monitoring gene expression, simultaneous molecular events, progression or regression of a disease such as cancer.

"Medical imaging", which is generally well-known within the art, concerns imaging for medical purposes. It preferably includes creating images of a sample derived from a subject, or of a subject or part of a subject. Medical imaging may be performed to reveal, diagnose or examine a disease or disorder, preferably a CXCR4 receptor-related disease or disorder such as any of the ones described hereinabove.

"Diagnostic imaging" as used herein refers to imaging for diagnostic purposes, such as for diagnosing a disease or disorder, preferably a CXCR4 receptor-related disease or disorder such as any of the ones described hereinabove.

A method of diagnostic imaging may or may not be a diagnostic method practised on the human or animal body.

A "sample" may be any sample. Non-limiting examples for a sample are cells, tissue section(s), tissue(s), and organ(s).

Preferably, the sample is derived from a subject, particularly from a human subject.

According to the invention, imaging may be carried out on any sample or subject or part of a subject comprising CXCR4 receptors.

According to the invention, imaging may involve any kind of imaging techniques known to the skilled person, wherein said techniques include, but are not limited to positron emission tomography (PET), single photon emission computed tomography (SPECT), magnetic resonance imaging (MRI), tomography such as computed tomography (CT), imaging via gamma cameras, imaging via autoradiography, imaging via phosphor imagers, and any combination(s) thereof.

Preferably, imaging occurs via any of positron emission tomography (PET), single photon emission computed tomography (SPECT), and magnetic resonance imaging (MRI). As will be understood by the skilled person, particularly preferred embodiments for such techniques depend on the respective detectable label used. Generally, when the label is a radionuclide, the detection step may preferably be performed using positron emission tomography (PET) or single photon emission computed tomography (SPECT). Magnetic resonance imaging (MRI) is preferred when magnetic or paramagnetic labels, such as a gadolinium label, are employed. Detectable labels for use with the compounds of the present invention are described hereinabove. In one embodiment, the detectable label is a fluorescent label. In one embodiment, the detectable label allows simultaneous imaging, such as dual PET/CT or PET/MRI. In this case, CT or MRI are preferably employed to analyze the morphology of the sample, subject, or part thereof, which is subjected to imaging.

Imaging may be carried out to determine the distribution or the accumulation of the detectable label, preferably via commonly used methods, such as autoradiography or phosphor imagers. Imaging may e.g. be carried out to obtain relative or quantitative distribution or accumulation data.

In an exemplary embodiment, (a method of) in vitro- or ex vivo-imaging involves the following steps: A compound of the invention comprising a detectable label is contacted with a sample such as cells, tissue section(s), tissue(s) or organ(s). The compound is preferably dissolved in a suitable buffer and said sample is incubated with this buffer. Incubation may occur for any suitable period of time such as in the range of seconds, minutes or hours. Subsequently, the detectable label is detected. This is effected by a suitable device, the nature of which depends on the imaging method used. Preferably or alternatively, in a further step, one or more images are obtained. This may e.g. be by direct imaging or imaging of slices of the incubated tissues.

In an exemplary embodiment, (a method of) in vivo-imaging involves the following steps: A compound of the invention comprising a detectable label is introduced into the living organism e.g. by injection, and, subsequently, the detectable label is detected. This is effected by a suitable device, the nature of which depends on the imaging method used. Preferably or alternatively, in a further step, one or more images are obtained. The acquisition of the imaging data such as the emission data is carried out over a suitable period of time such as for minutes to hours. Using commonly employed equipment and suitable software packages, these data may e.g. result in planar or 3D distribution pattern of the activity distribution in the organism. Depending on the method, the obtained data can be qualitative or quantitative.

In an exemplary embodiment, (a method of) in vivo-imaging involves the following steps: a) positioning a subject in an imaging device, b) delivering a compound of the invention to the subject, c) acquiring at least one image; or a) delivering a compound of the invention to the subject, b) positioning a subject in an imaging device, c) acquiring at least one image.

In preferred embodiments, a method of imaging does not involve a step of treatment of the human or animal body by surgery or therapy. Yet, certain aspects of the invention explicitly concern a compound or composition of the invention for use in a method of imaging CXCR4 receptors, in particular of medical imaging, especially of diagnostic imaging, wherein said method involves at least one step of treatment of the human or animal body by surgery or therapy.

Preferably, any of the (methods of) imaging referred to herein is employed for the imaging of CXCR4 receptors on stem cells, tumor stem cells, hematopoietic stem cells and other progenitor cells and tissues under remodeling and repair by stem and progenitor cell adhesion.

"Tissues under remodeling and repair by stein and progenitor cell adhesion" as used herein relates to, without being limited thereto, cells or tissues such as cells or tissues engaged in a neoangiogenic process, cells or tissues affected by vascular injury and cells or tissues affected by myocardial infarction.

Preferably, in vivo-imaging of CXCR4 expression using compounds of the present invention that are radiolabeled with appropriate radionuclides is effected via PET or SPECT. In in vivo-imaging, images of the subject may be taken after a short time after administration, by which stage any tissues having a relatively high expression of CXCR4 will show a relative concentration of the compound of the invention.

In case of in vivo-methods for imaging, the compound preferably comprises a radiolabel and the imaging is preferably performed using PET or SPECT. Preferred embodiments concern in viva-methods for the diagnostic imaging of a neoplastic condition.

In case of in vitro-methods for imaging, the compound preferably comprises a radiolabel or fluorescent label and the imaging is preferably performed using autoradiography or fluorescence. Preferred embodiments concern in vitro-methods for the diagnostic imaging of a neoplastic condition.

In preferred embodiments, the invention relates to the imaging of tumors such as cancer. As described above, cancer may refer to a cancer not including metastases, to a cancer including metastases, or to cancer metastases.

In one embodiment, the cancer is selected from the group consisting of astrocytoma, B-cell lymphoma, breast adenocarcinoma, breast carcinoma, cervical adenocarcinoma, colon adenocarcinoma, colorectal adenocarcinoma, colorectal carcinoma, glioblastoma, hepatocellular carcinoma, hepatoma and pancreatic carcinoma, leukaemia, large cell lung cancer, lung adenocarcinoma, lung carcinoma, lung mesothelioma, lung squamous cell carcinoma, melanoma, neuroblastoma, non small cell and small cell lung cancer (NSCLC and SCLC), ovarian adenocarcinoma, pancreatic adenocarcinoma, pancreatic carcinoma, prostate adenocarcinoma, prostate carcinoma, rectal adenocarcinoma, and renal cell adenocarcinoma.

In another embodiment, the cancer is selected from the group consisting of breast adenocarcinomas, Burkitt's B-cell lymphoma, cervical adenocarcinomas, colon and rectal adenocarcinomas, oesophageal cancer, gliomas, glioblastomas, hepatocellular carcinomas (malignant hepatomas), hepatomas, leukaemia, mamma-carcinomas, melanoma, neuroblastoma, nasopharyngeal adenocarcinoma, non small cell lung cancer (NSCLC), pancreatic adenocarcinomas, prostate cancer, small cell lung cancer (SCLC), T-cell lymphoma, and thyroid cancer.

In a preferred embodiment, the cancer is selected from the group consisting of breast adenocarcinoma, colorectal adenocarcinoma, lymphoma, melanoma carcinoma, prostate carcinoma, prostate adenocarcinoma, small cell lung cancer.

Preferably, the imaging allows a clear delineation of CXCR4 positive tumors (including or not including any metastases), e.g. in vivo. Imaging according to the invention may provide tools for the diagnosis of cancer, the detection of tumors and/or tumor metastases, the investigation of tumors and/or tumor metastases, the removal of tumors and/or tumor metastases via surgery, and the like.

In one embodiment of the invention, the imaging is employed for diagnosing or investigating any CXCR4 receptor-related disease or disorder, such as the ones referred to herein.

In one particular embodiment, said disease or disorder is selected from any of the diseases and disorders referred to on pages 49 to 58 of WO2008/08854A, which is specifically incorporated herein by reference.

In one preferred embodiment, imaging is employed for diagnosing or investigating an immune disease, an autoimmune disease, an inflammatory condition and/or a neurological disease, preferred examples thereof being as described above.

In other preferred embodiments, (a method of) imaging is employed for monitoring any CXCR4 receptor-related disease or disorder, such as the ones referred to herein. In particular embodiments, (a method of) imaging is employed for monitoring for investigating inflammatory processes or angiogenic processes.

Accordingly, in a further aspect, the invention relates to a method for monitoring a CXCR4 receptor-related disease or disorder. The invention also relates to a compound or composition of the invention for use in monitoring a CXCR4 receptor-related disease or disorder.

The invention also relates to a compound or composition of the invention for use in a method of monitoring a CXCR4 receptor-related disease or disorder.

Using a compound of the invention in imaging as described herein, or employing a method of imaging as described herein, is preferably done to determine the localization, the extent and/or the kinetics of a disease or disorder. In the case of analyzing kinetics, the extent of the disease is preferably analyzed early during therapy in order to be able to quickly detect a response to therapy.

The compounds of the invention are expected to allow early response monitoring as well as the selection of patients that may especially benefit from a planned therapy. A selection of patients means that patients are selected before commencing any therapy, for which disease it is know that the density of CXCR4 receptors correlates with the reaction to therapy or with the expected response. The therapy must not necessarily be a therapy directed to CXCR4, such as by employing a compound of the invention as an antagonist, but can be directed to any target structure which correlates with CXCR4 receptor density.

One exemplary embodiment relates to the qualitative or quantitative imaging of the CXCR4 receptor status in vivo using compounds of the invention comprising a detectable label, e.g. by means of PET using the aforementioned compounds, for planning of individualized therapies that directly address (are mediated by) the CXCR4 receptor status or indirectly affect or modulate the CXCR4 receptor status.

Non-limiting examples in this respect relate to the therapy of maminacarcinomas by means of anti-Her2/neu antibodies (e.g. with trastuzumab, trade name Herceptin®) and the anti-angiogenetic antibody therapy of colon carcinomas using anti-VEGF-A antibody bevacizumab (trade name Avastin®).

In another embodiment, a compound of the invention is employed to follow or monitor the efficiency of such therapies by therapy response evaluation, preferably early therapy response evaluation. For this purpose the compounds of interest may be injected prior to or early after beginning of such therapies to evaluate response to therapy via comparison of the signal, such as the CXCR4-PET signal, prior to (baseline scan) as well as early after or during therapy.

Other preferred embodiments relate to the use of a compound of the invention for imaging inflammatory processes, preferably in vivo, particularly via PET imaging, and to a corresponding method.

Other preferred embodiments relates to the use of a compound of the invention for imaging angiogenetic processes/angiogenesis processes as well as to a corresponding method.

A further aspect of the invention relates to the use of a CXCR4 receptor ligand, preferably a compound as defined hereinabove, to monitor the extent of stein cell depletion, such as during an endoradiotherapeutic approach. Preferably, the use alternatively or further includes monitoring an increasing pool of stem cells in the bone marrow, such as after stem cell transplantation.

One embodiment concerns a method of monitoring the extent of stem cell depletion during an endoradiotherapeutic approach, the method comprising administering a CXCR4 receptor ligand, preferably a compound as defined hereinabove, to a sample or a subject. Preferably, the method includes a subsequent step of monitoring the increasing pool of stein cells in the bone marrow after stein cell transplantation.

Said CXCR4 receptor ligand may be any known molecule that specifically binds to the CXCR4 receptor. Examples include but are not limited to FC131 referred to above and its derivatives, particularly i) the ligands disclosed in WO 2007/096662 A2, ii) the ligands disclosed in WO 2009/027706 A2. Preferably, the CXCR4 receptor ligand is any of the compounds described hereinabove. Preferably, said ligand comprises a detectable label, particularly the ones described herein.

In one embodiment, the invention relates to the use of a compound of the invention for the diagnostic imaging of changes of the status of CXCR4 expressing cells, particularly stem cells, in the bone marrow.

In a further aspect, the present invention relates to a compound as defined above or composition as defined above for use in a diagnostic method practiced on the human or animal body for the diagnosis of a CXCR4 receptor-related disease or disorder.

Such diagnostic method includes technical steps that are constitutive for making the diagnosis, wherein specific interactions with the human or animal body occur when carrying out these steps, as well as the diagnosis for curative purposes. Said diagnosis stricto sensu represents the deductive medical decision phase as a purely intellectual exercise.

In one embodiment, such diagnostic method comprises the steps of administering a compound of the invention to a subject, collecting imaging data from the subject, comparing the imaging data with standard values, finding a symptom of a CXCR4 receptor-related disease or disorder during the comparison, attributing the symptom to a particular clinical picture to establish the diagnosis.

Moreover, the invention relates to a method of diagnosing a CXCR4 receptor-related disease or disorder, wherein the method comprises a step of administering a compound as defined above or composition as defined above to a sample derived from a subject or to a subject, and a subsequent step of imaging CXCR4 receptors.

Preferably, the compound comprises a detectable label, and the method comprises a step of administering a compound as defined above to a sample derived from a subject or to a subject, and particularly comprises a subsequent step of detecting the detectable label and/or a subsequent step of obtaining one or more images.

Due to their features, the compounds of the invention may be suitably used for various other applications directly or indirectly related to the CXCR4 receptor. Accordingly, in even further aspects, the present invention relates to any of the following embodiments:

Use of a compound of the invention, particularly wherein the compound comprises a detectable label, in the visualization of CXCR4 receptor and CXCR4 receptor containing tissue.

Use of a compound of the invention for affinity purification of CXCR4 receptors or cells containing one or more CXCR4 receptors.

Use of a compound of the invention for the diagnostic imaging of changes of CXCR4 receptor expression of cells, preferably stem cells, particularly cells in the bone marrow.

A method of affinity purification of CXCR4 receptors or cells containing one or more CXCR4 receptors, comprising a step of contacting a compound of the invention with a sample containing a CXCR4 receptor or cells containing one or more CXCR4 receptors, particularly wherein the method further comprises one or more steps of removing other constituents from the sample to increase purity of the CXCR4 receptor or cells containing one or more CXCR4 receptors.

The CXCR4 ligands of the present invention may be modified with additional (functional) moieties and/or moieties that immobilize the CXCR4 ligands.

A method of determining the metastatic potential of cells of a neoplasia, the method comprising exposing said cells to a compound of the invention, so as to allow the compound to bind to CXCR4 receptors on the surface of the cells, and determining the presence and/or amount of compound bound to the cells. In this method, an increased number of CXCR4 receptors correlates to an increased metastatic potential of the primary tumor. Accordingly, conclusions as to the metastatic potential of cells of a neoplasia may be drawn from the presence and/or amount of a compound described above bound to the cells via CXCR4 receptors. According to the current knowledge of the inventors, the compounds of the invention may allow for imaging of the metastatic potential of primary tumors of e.g. a cancer selected from the group consisting breast adenocarcinomas, Burkitt's B-cell lymphoma, cervical adenocarcinomas, colon and rectal adenocarcinomas, oesophageal cancer, gliomas, glioblastomas, hepatocellular carcinomas (malignant hepatomas), hepatomas, leukaemia, mamma-carcinomas, melanoma, neuroblastoma, nasopharyngeal adenocarcinoma, non small cell lung cancer (NSCLC), pancreatic adenocarcinomas, prostate cancer, small cell lung cancer (SCLC), T-cell lymphoma, and thyroid cancer. Said method of determining the metastatic potential of cells may be carried out in viva or in vitro (i.e. using a sample of cells or tissue removed from a patient). When the compound of the invention comprises a radionuclide, the imaging, or the determination of the presence and/or amount of bound compound, may in particular be performed using PET or SPECT. When magnetic or paramagnetic labels are employed, magnetic resonance imaging is preferred.

The compounds described hereinabove may also be suitably employed in the field of stem cell mobilization and/or transplantation. As it is known in the art (cf. Levesque et al., 2008), hematopoietic stem cells (HSCs), which normally reside in the bone marrow, can be forced into the blood by mobilization, which is used clinically to harvest large numbers of HSCs for transplantation. One example for a suitable compound is plerixafor described above. The mobilization of hematopoietic stem cells from the bone marrow to the bloodstream makes use of the interaction between the chemokine SDF-1/CXCL12 and its receptor CXCR4, which serves to retain HSCs within the bone marrow. For mobilization, this interaction may be disturbed by molecules acting as CXCR4 ligands, which is why the compounds of the present invention, e.g. as direct antagonists of the interaction between SDF-1 and CXCR4, may be suitable for inducing mobilization of stem cells. Therefore, it is envisaged that the compounds of the present invention may function as such mobilizing agents and may be used for improving the stem-cell harvest from bone-marrow donors and shorten the collection time as compared to originally employed methods.

Accordingly, in a further aspect, the invention relates to the use of a compound described hereinabove for mobilizing and/or harvesting stem cells. The invention further relates to a compound as defined hereinabove for use in a method of mobilizing and/or harvesting stem cells.

The invention also relates to a method of mobilizing stem cells in a subject, the method comprising a step of administering a compound of the present invention to a sample containing stem cells or to a subject. Also envisaged is a method of harvesting stem cells, the method comprising a step of administering a compound of the present invention to a sample containing stem cells or to a subject and a subsequent step of collecting stem cells from said sample or subject. Preferably, the latter methods are no methods for the treatment of the human or animal body by surgery or therapy.

One exemplary application for stem cell mobilization is its use during cancer therapy, such as by radioimmunotherapeutic treatment, e.g. of lymphomas by means of anti-CD20 radiolabeled antibodies. To overcome the side effects of such therapies, i.e. complete stem cell (bone marrow) depletion, stem cell transplantations are carried out. Prior to the radiotherapeutic approach, stem cells are mobilized from their niches in the bone marrow, are collected from the blood, stored and re-injected after the therapy. Since CXCR4 ligands have been described to mobilize stem cell from the bone marrow niches, the compounds of the invention may be valuable compounds for this therapeutic approach.

Thus, in a further aspect, the invention relates to a compound as defined above or composition as defined above for use in a method of stem cell transplantation comprising the following steps
i) administering a compound of the present invention to a subject,
ii) collecting stem cells from said subject,
iii) optionally storing the collected stem cells, and
iv) re-introducing the collected stem cells into the subject.

Further uses and methods in which the compounds of the invention may be employed will be readily apparent to a person skilled in the art based on the disclosures herein.

EXAMPLES

Abbreviations

DCM: Dichloromethane, RP-HPLC: Reversed Phase High Pressure Liquid Chromatography, TFA; Trifluoroacetic acid, NMR: Nuclear Magnetic Resonance, THF: Tetrahydrofuran, EtOAc: Ethylacetate, RT: room temperature, Boc: tert-butyloxycarbonyl, DIEA: Diisopropylethylamine, MeOH: methanol, NMP: N-methyl-pyrollidone, DPPA: Diphenylphosphoryl azide, DMF: N,N-dimethylformamide, Ac: acetate, Fmoc: Fluorenylmethyloxycarbonyl, Alloc: Allyloxycarbonyl, Xaa: undefined amino acid, SPPS: Solid Phase Peptide Synthesis, Orn: ornithine, Nal: L-3-(2-naphthyl)alanine, R(Pbf): arginine with Pbf protected side chain, Tyr (tBu): tyrosine with tBu protected side chain, Fmoc-Tyr(tBu): tyrosine with tBu protected side chain and Fmoc protected $N^{\alpha}$, Aba/ABS: 4-aminobenzoic acid, Fmoc-Aba: N-Fmoc protected 4-aminobenzoic acid, Amba/AMBS: 4-aminomethylbenzoic acid, Fmoc-Aba: N-Fmoc protected 4-aminomethylbenzoic acid, betaAla: beta-alanine; 3-aminopropanoic acid, Fmoc-betaAla: N-Fmoc protected beta-alanine, Ava/AVS: 5-aminovaleric acid, Fmoc-Ava: N-Fmoc protected 5-aminovaleric acid, Ahx: 6-aminohexanoic acid, Fmoc-Ahx: N-Fmoc protected 6-aminohexanoic acid, Trigas: triethylenglycol-8-amino-1-acid, Fmoc-Trigas: N-fluorenylmethoxycarbonyl-triethyleneglycol-8-amino-1-acid, RNalG/RNalG: arginine, L-3-(2-naphthyl)alanine, glycine. Besides, the abbreviation "yorn" specifies that in the respective cyclopeptide, $Xaa^1$ is D-Tyr, the residue between $Xaa^1$ and $Xaa^2$ is derived from D-Orn, and R is H; whereas the abbreviation "yorn" specifies that in the respective cyclopeptide, $Xaa^1$ is D-Tyr, the residue between $Xaa^1$ and $Xaa^2$ is derived from D-Orn, and R is Me.

General Description of Synthetic Pathways

Building Blocks for Solid Phase Peptide Synthesis (SPPS).

$N^{\alpha}$-o-nitrobenzoesulfonyl-$N^{\delta}$-Alloc-D-ornithine ($N^{\alpha}$-Ns-$N^{\delta}$-Alloc-D-Orn) was synthesized starting from $N^{\alpha}$—H—$N^{\delta}$-Boc-D-Orn by Ns protection, Boc deprotection, and Alloc reprotection. 1,4,7-tris(tert-butoxycarbonylmethyl)-1,4,7,10-tetraazacyclododecane-10-acetic acid (tris(t-Bu)DOTA) (Mizukami et al., 2008), 4-(9-Fluorenylmethyloxycarbonylaminomethyl)-benzoic acid (Yang et al., 2008), 4-(9-Fluorenylmethyloxycarbonylamino)-benzoic acid (Van der Plas et al., 2008), and N-fluorenylmethoxycarbonyl-triethyleneglycol-8-amino-1-acid (Fmoc-Trigas) (Aldrich et al., 2003), were synthesized according to literature.

Peptide Synthesis.

Standard Fmoc strategy with acid labile side chain protecting groups (tBu for Tyr and 2,2,4,6,7-pentamethyldihydrobenzofurane-5-sulfonyl (Pbf) for Arg) was employed to construct peptides on tritylchloridpolystyrene (TCP) Resin. Standard peptide bonds were built by coupling with O-(benzotriazol-1-yl)-N,N,N',N'-tetramethyluronium tetrafluoroborate (TBTU) and addition of N-hydroxybenzotriazole (HOBt) to suppress racemization. N-alkylated amines were acylated using 2-(7-aza-1H-benzotriazole-1-yl)-1,1,3,3-tetramethyluronium hexafluorophosphate (HATU) with 1-hydroxy-7-azabenzotriazole (HOAt) as racemization suppressant. HATU was also used to acylate anilines and to attach tris(t-Bu)DOTA. Gly was chosen as C-terminal residue to avoid racemization in the cyclization step and at the same time raise its yields by turn preformation of the N-terminal D-amino acid.

N-methylation was achieved via the Fukuyama-Mitsunobu reaction by treating Ns-protected amines with methanol under typical Mitsunobu conditions (diisopropylazodicarboxylate (DIAD) and triphenylphosphine) (Demmer et al., 2008). Ns was cleaved by treatment with 1,8-diazabicyclo [5.4.0]undec-7-ene (DBU) and 2-mercaptoethanol to yield the secondary amine.

$N^{\alpha}$-methylated peptides were built from resin-bound $N^{\alpha}$-Ns-$N^{\epsilon}$-Alloc-D-Orn-Arg(Pbf)Nal-Gly by N-methylation, Alloc deprotection, modification of the side chain with standard Fmoc strategy, Ns deprotection, attachment of Fmoc-D-Tyr(t-Bu) with HATU followed by Fmoc deprotection, cleavage of the peptide, cyclization and deprotection of the acid labile protection groups (Scheme 1). Alloc was chosen as orthogonal protecting group as it is—in contrast to Fmoc— stable under Mitsunobu as well as under alkaline Ns deprotection conditions.

Scheme 1. Synthesis strategies for branched cyclic pentapeptides with $N^{\alpha}$-methylated backbones. The numbers refer to the general procedures given in the text.

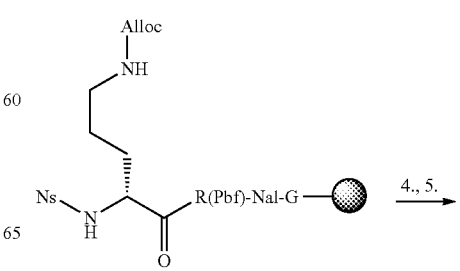

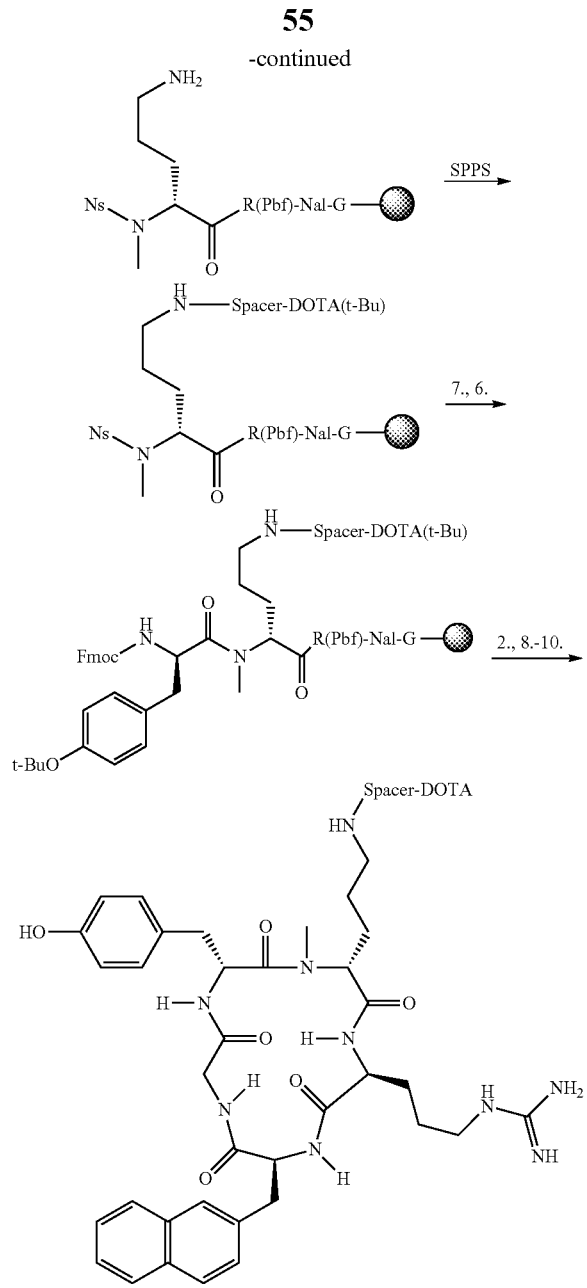

The branched peptides were cleaved from the resin with 20% 1,1,1,3,3,3-hexafluoroisopropanol (HFIP) in DCM and cyclized with DPPA and NaHCO$_3$ in DMF. Final deprotection of acid labile groups was done in 95% trifluoroacetic acid (TFA) containing 2.5% 1120 and 2.5% triisopropylsilane (TIPS) before RP-HPLC purification. ESI-MS was used to identify the peptides and the purity determined by analytical RP-HPLC was better than 95%. Indium and Gallium ions were chelated by DOTA bearing peptides in an additional step in aqueous NH$_4$Ac solution and again purified by RP-HPLC.

Materials and Methods

All commercially available chemical reagents were used without further purification. Technical solvents were distilled before use.

Trityl resins were purchased from PepChem and amino acid derivatives from Iris Biotech GmbH, NovaBiochem, Merck, Bachem, Neosystem, Aldrich, while all other chemicals were bought from Aldrich, Fluka and Merck if not stated otherwise.

NMP was obtained from BASF and used without further distillation. Dry solvents were purchased from Aldrich, Fluka and Merck. Dry dichloromethane was distilled from calciumhydride under argon and kept over 4 Å molecular sieve. Water for RP-HPLC was filtered through a 0.22 μm filter (Millipore, Millipak40).

RP-HPLC analyses were performed using an Omnicrom YMC column (4.6 mm×250 mm, 5 μm C$_{18}$, 1 mL/min). The eluent was a linear gradient from water (0.1% TFA) to acetonitrile (0.1% TFA) over 30 minutes and detection at 220 nm and 254 nm. The retention time (R$_t$) of the analytical RP-HPLC is given in minutes with the gradient in percentage of acetonitrile. Purities were determined at 220 nm with the Unicorn software package and are given relative to their starting compound.

Semi-preparative RP-HPLC was done on a Beckman System Gold equipped with high pressure module 125, UV-detector 166, and using an Omnicrom ODS-A C18 (120 Å, 5 μm, 250 mm×20 mm) column in combination with the same solvents as stated above.

NMR spectra were recorded on a Bruker Avance 250 or Bruker DMX 500 at 298K. The chemical shifts are reported in ppm on the δ scale relative to the solvent signal. $^{13}$C-NMR-spectra were recorded using $^1$H-broad band decoupling. Pulse programs were taken from the Bruker library or written by members of our group. Samples were prepared in tubes with a diameter of 5 mm using 0.5 ml of deuterated solvent with a final concentration of approximately 20-50 mM. The resulting spectra were processed on a PC workstation using Bruker TOPSPIN 1.3 and MestRe Nova software.

ESI mass spectra were recorded on a Finnigan LCQ in combination with a Agilent/HP 1100 RP-HPLC system using a Omnicrom YMC ODS-A C18 column (120 Å, 3 μm, 125 mm×2 mm) with a flow rate of 0.2 mL/min. The eluent was a linear gradient from water to acetonitrile with 0.1% formic acid over 20 min with detection at 220 nm.

A. General Amine Protection Procedure.

To a 0.2 M solution of amino acid and NaHCO$_3$ (0.5 M) the same volume of a 0.2 M reagent solution in THF was added and stirred at RT for 1 h. The THF was evaporated under reduced pressure, the aqueous phase washed once with diethyl ether and acidified with conc. HCl to pH 1 and the product extracted with EtOAc. The combined organic layers were dried (Na$_2$SO$_4$), filtered, concentrated and dried in vacuo.

B. Boc Deprotection.

3-8 mmol of Boc protected amino acid were dissolved in 10 ml DCM and 5 ml of TPA added slowly. The solution was stirred at RT for 45 min and the solvent evaporated in vacuo to yield the crude product ready for reprotection.

1. Loading of Tritylchloridpolystyrene (TCP) Resin.

Peptide synthesis was carried out using TCP-resin (0.9 mmol/g) following standard Fmoc-strategy. Fmoc-Xaa-OH (1.2 eq.) were attached to the TCP resin with DIEA (2.5 eq.) in anhydrous DCM (0.8 mL/g resin) at room temperature for 1 h. The remaining trityl chloride groups were capped by addition of 1 mL/g (resin) of a solution of MeOH, DIEA (5:1; v:v) for 15 min. The resin was filtered and washed 5 times with DCM and 3 times with MeOH. The loading capacity was determined by weight after drying the resin under vacuum and ranged from 0.4-0.9 mmol/g.

2. On-Resin Fmoc Deprotection.

The resin-bound Fmoc peptide was treated with 20% piperidine in NMP (v:v) for 10 minutes and a second time for 5 minutes. The resin was washed 5 times with NMP.

3. TBTU/HOBt Coupling.

A solution of Fmoc-Xaa-OH (2 eq.), TBTU (2 eq.), HOBt (2 eq.), DIEA (5.2 eq.) in NMP (1 mL/g resin) was added to the resin-bound free amine peptide and shaken for 60 min at room temperature and washed 5 times with NMP.

4. N-Methylation Under Mitsunobu Conditions.

A solution of triphenylphosphine (5 eq.), DIAD (5eq.) and MeOH (10 eq.) in dry THF (1 mL/g resin) was added to the resin-bound Ns protected peptides and shaken at room temperature for 10 minutes. The resin was filtered off, and washed 3 times with dry THF and 3 times with NMP.

5. Alloc Deprotection.

Pd(PPh$_3$)$_4$ (0.125 eq.) in dry DCM (0.5 mL/g resin) was added to the resin-bound Alloc peptide followed by an addition of phenylsilan in dry DCM (0.5 ml/g resin) and shaken for 1 hour. The resin was washed 5 times with DCM.

6. HATU/HOAt Coupling.

A solution of Fmoc-Xaa-OH or tris(t-Bu)DOTA (2 eq.), HATU (2 eq.), HOAt (2 eq.), DIEA (4 eq.) in NMP (1 mL/g resin) was added to the resin-bound peptides and shaken for 3 hours at room temperature and washed 5 times with NMP.

7. On-Resin Ns Deprotection.

For Ns deprotection, the resin-bound Ns-peptides were stirred in a solution of mercaptoethanol (10 eq.) and DBU (5 eq.) in NMP (1 mL/g resin) for 5 minutes. The deprotection procedure was repeated one more time and the resin was washed 5 times with NMP.

8. Peptide Cleavage.

For complete cleavage from the resin the peptides were treated three times with a solution of DCM and HFIP (4:1; v:v) at room temperature for half an hour and the solvent evaporated under reduced pressure.

9. Cyclization.

To a solution of peptide in DMF (1 mM peptide concentration) and NaHCO$_3$ (5 eq.) DPPA (3 eq.) was added at RT and stirred over night or until no linear peptide could be observed by ESI-MS. The solvent was evaporated to a small volume under reduced pressure and the peptides precipitated in saturated NaCl solution and washed two times in HPLC grade water.

10. Removal of Acid Labile Side Chain Protecting Groups.

Cyclized peptides were stirred in a solution of TFA, water and TIPS (95:2.5:2.5; v:v:v) at room temperature for one hour or until no more protected peptide could be observed by ESI-MS and precipitated in diethyl ether and washed two more times.

11. Chelation of In with DOTA Ligands.

DOTA ligands were dissolved in 5 M aqueous ammonium acetate (0.5 ml; pH 4.5) and treated with InCl$_3$ (5 eq.) dissolved in 5 M ammonium acetate (0.05 ml). After 15 min of stirring at RT the solution was subjected to HPLC purification.

12. Chelation of Ga with DOTA Ligands.

DOTA ligands were dissolved in 0.01 M aqueous ammonium acetate (0.5 ml; pH 4.5) and treated with Ga(NO$_3$)$_3$ (10 eq.) dissolved in 0.01 M ammonium acetate (0.05 ml) resulting in a final pH of 3. After 2-4 h of stirring at RT the solution was subjected to HPLC purification.

Synthetic Description for Individual Compounds

N$^\alpha$-Ns-N$^\delta$-Boc-D-ornithine

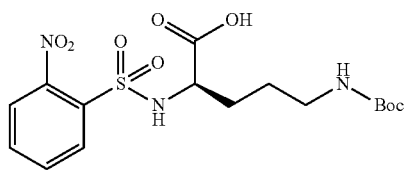

C$_{16}$H$_{23}$N$_3$O$_8$S
Mol. Wt.: 417.43

N$^\delta$-Boc-D-ornithine (1.51 g, 6.5 mmol) was protected with o-nitrobenzenesulfonylchloride (NsCl) (1.44 g, 6.5 mmol) after procedure A, and gave a slightly yellow, sticky oil as sufficiently pure product (2.43 g, 90%). $^1$H NMR (250 MHz, DMSO-d$_6$): δ 12.72 (s, 1H), 8.46 (d, 1H), 8.01 (m, 1H), 7.93 (m, 1H), 7.86 (m, 2H), 6.78 (t, 1H), 3.85 (m, 1H), 2.85 (m, 2H), 1.38 (m, 13H). $^{13}$C NMR (125 MHz, DMSO-d$_6$): 172.3, 147.7, 134.4, 133.8, 132.9, 130.3, 124.5, 110.7, 77.9, 56.2, 29.7, 28.7, 26.4. R$_t$ (10-100%): 18.6 min. m/z calculated for C$_{16}$H$_{23}$N$_3$O$_8$S: 417.12. found 440.1 [M+Na$^+$].

Example 2

N$^\alpha$-Ns-N$^\delta$-Alloc-D-ornithine

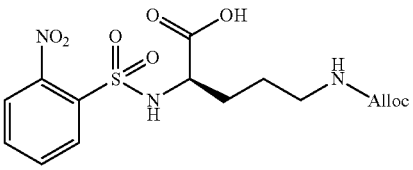

C$_{15}$H$_{19}$N$_3$O$_8$S
Mol. Wt.: 401.39

N$^\alpha$-Ns-N$^\delta$-Boc-L-ornithine (2.41 g, 5.78 mmol) was subjected to Boc deprotection (procedure B.) and subsequently reprotected with allyl chloroformate (0.61 mL, 5.78 mmol) after procedure A, and gave a colorless, sticky syrup as sufficiently pure product (2.18 g, 94%). $^1$H NMR (250 MHz, DMSO-d$_6$): δ 8.1 (dd, 1H), 8.0 (dd, 1H), 7.8 (m, 2H), 7.2 (t, 1H), 5.9 (br m, 1H), 5.2 (m, 2H), 4.5 (d, 2H), 3.5 (t, 1H), 2.9 (dd, 2H), 1.7 (m, 2H), 1.4 (br m, 2H). $^{13}$C NMR (125 MHz, DMSO-d$_6$): 172.9, 156.4 147.9, 134.4, 134.3, 133.3, 133.2, 130.3, 125.1, 117.3, 64.6, 57.5, 30.7, 25.8. R$_t$ (10-100%): 16.9 min. m/z calculated for C$_{15}$H$_{19}$N$_3$O$_8$S: 401.09. found 402.2 [M+H$^+$].

N-Fmoc-5-aminopentanoic acid 5-aminopentanoic acid (0.35 g, 3 mmol) was protected with o-Fmoc-OSu (1.01 g, 3 mmol) after procedure A, and gave a slightly yellow, sticky oil as sufficiently pure product (0.92 g, 90%). $^1$H NMR (500 MHz, DMSO-d$_6$): δ 12.02 (br s, 1H), 7.86 (d, 2H), 7.67 (d, 2H), 7.39 (t, 2H), 7.31 (t, 2H), 7.26 (t, 1H), 4.28 (d, 2H), 4.19 (t, 1H), 2.97 (dd, 2H), 2.19 (t, 2H), 1.43 (br m, 4H). $^{13}$C NMR (125 MHz, DMSO-d$_6$): 174.9, 156.7, 144.4, 141.2, 128.0, 127.5, 125.6, 120.5, 65.6, 64, 47.2, 33.8, 29.3, 22.2. R$_t$ (10-100%): 20.73 min. m/z calculated for C$_{20}$H$_{21}$NO$_4$: 339.15. found 701.3 [2M+Na$^+$].

yorn'(DOTA)RNalG

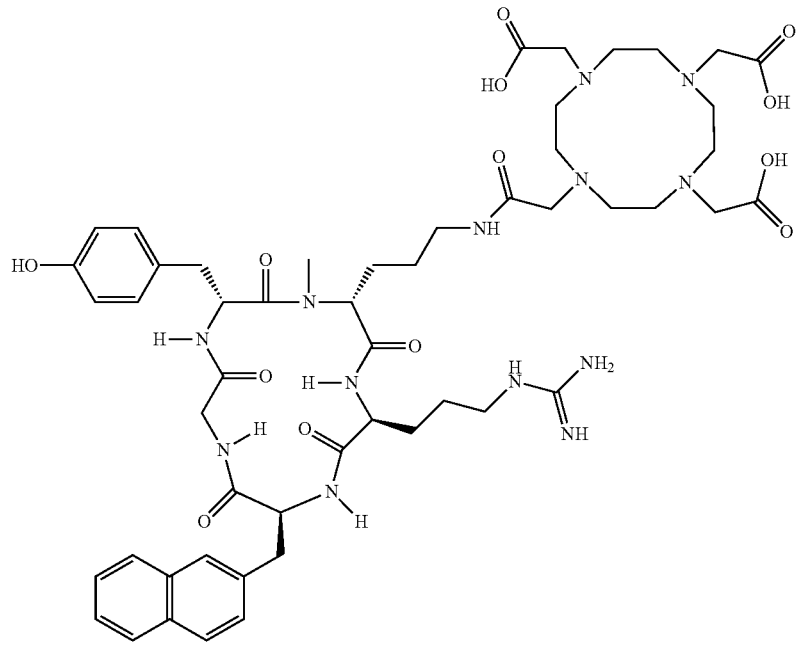

yorn'(DOTA)RNalG
cyclo(-D-Tyr-(α-methyl, δ-DOTA)-D-Orn-R-Nal-G)
C$_{52}$H$_{73}$N$_{13}$O$_{13}$
Exact Mass: 1087,55
Mol. Wt.: 1088,22

The linear peptide R$^α$-Ns-N$^δ$-Alloc-D-Orn-R(Pbf)-Nal-G was synthesized with standard Fmoc peptide chemistry following general protocols for resin-attachment (1.) of Gly and repeated Fmoc deprotection (2.) and attachment of the following (protected) amino acid (3.). Subsequently the Orn N$^α$ was N-methylated (4.), Alloc cleaved (5.), and tris(tBu) DOTA attached (6.). After this modification of the side-chain the Orn N$^α$-Ns group was cleaved (7.), Fmoc-Tyr(tBu) attached (6.), its Fmoc group cleaved (2.) and the resulting branched peptide cleaved from the resin (8.). The peptide was cyclized (9.), deprotected (10.) and purified by RP-HPLC. The metal chelates of the pure peptides were obtained by labeling with Indium (11.) or Gallium (12.) with subsequent RP-HPLC purification.

yorn'(Aba, DOTA)RNalG

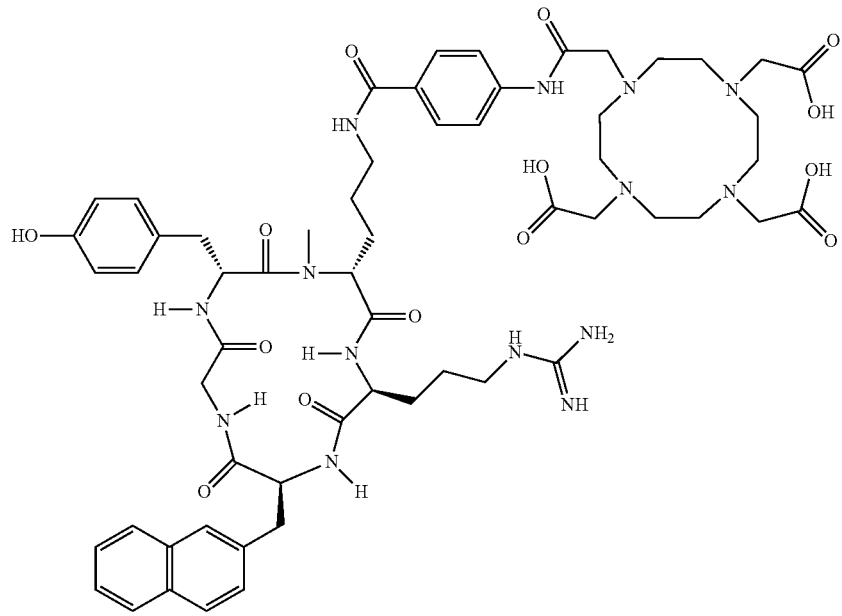

yorn'(Aba, DOTA)RNalG
cyclo(-D-Tyr-(α-methyl, δ-4-aminobenzoic acid, DOTA)-D-Orn-R-Nal-G)
$C_{59}H_{78}N_{14}O_{14}$
Exact Mass: 1206,58
Mol. Wt.: 1207,34

The linear peptide $N^\alpha$-Ns-$N^\delta$-Alloc-D-Orn-R(Pbf)-Nal-G was synthesized with standard Fmoc peptide chemistry following general protocols for resin-attachment (1.) of Gly and repeated Fmoc deprotection (2.) and attachment of the following (protected) amino acid (3.). Subsequently the Orn $N^\alpha$ was N-methylated (4.), Alloc cleaved (5.), 4-(Fluorenylmethyloxycarbonylamino)-benzoic acid attached (3.), Fmoc cleaved (2.), and tris(t-Bu)DOTA attached (6.). After this modification of the side-chain the Orn $N^\alpha$-Ns group was cleaved (7.), Fmoc-Tyr(tBu) attached (6.), its Fmoc group cleaved (2.) and the resulting branched peptide cleaved from the resin (8.). The peptide was cyclized (9.), deprotected (10.) and purified by RP-HPLC. The metal chelates of the pure peptides were obtained by labeling with Indium (11.) or Gallium (12.) with subsequent RP-HPLC purification.

yorn'(Amba, DOTA)RNalG

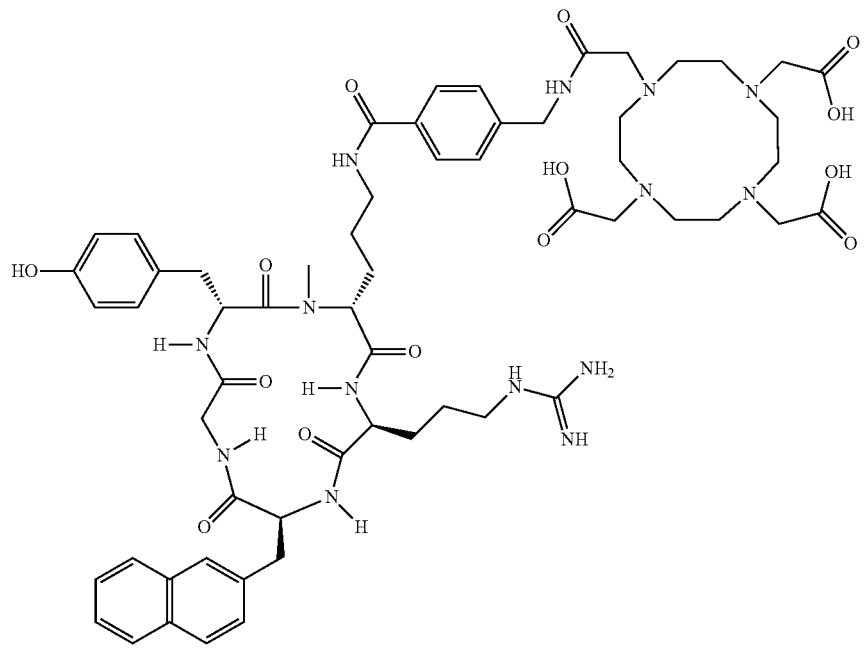

yorn'(Amba, DOTA)RNalG
cyclo(-D-Tyr-(α-methyl, δ-4-(aminomethyl)benzoic acid, DOTA)-D-Orn-R-Nal-G)
$C_{60}H_{80}N_{14}O_{14}$
Exact Mass: 1220,6
Mol. Wt.: 1221,36

The linear peptide $N^\alpha$-Ns-$N^\delta$-Alloc-D-Orn-R(Pbf)-Nal-G was synthesized with standard Film peptide chemistry following general protocols for resin-attachment (1.) of Gly and repeated Fmoc deprotection (2.) and attachment of the following (protected) amino acid (3.). Subsequently the Orn $N^\alpha$ was N-methylated (4.), Alloc cleaved (5.), 4-(Fluorenylmethyloxycarbonylaminomethyl)-benzoic acid attached (3.), Fmoc cleaved (2.), and tris(t-Bu)DOTA attached (6.). After this modification of the side-chain the Orn $N^\alpha$-Ns group was cleaved (7.), Fmoc-Tyr(tBu) attached (6.), its Fmoc group cleaved (2.) and the resulting branched peptide cleaved from the resin (8.). The peptide was cyclized (9.), deprotected (10.) and purified by RP-HPLC. The metal chelates of the pure peptides were obtained by labeling with Indium (11.) or Gallium (12.) with subsequent RP-HPLC purification.

yorn'(Aba, G, DOTA)RNalG

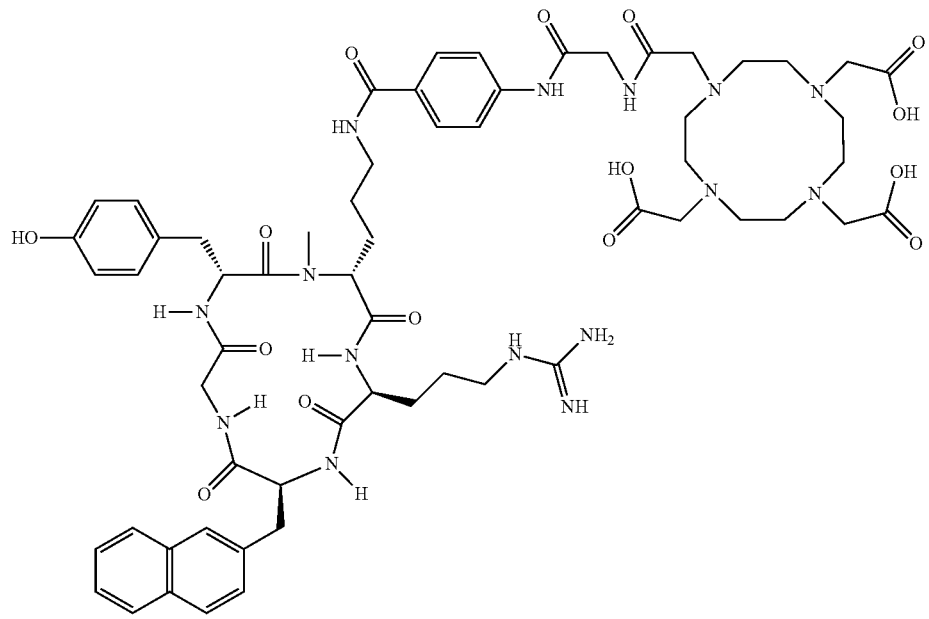

yorn'(Aba, G, DOTA)RNalG
cyclo(-D-Tyr-(α-methyl, δ-4-aminobenzoic acid, G, DOTA)-D-Orn-R-Nal-G)
$C_{61}H_{81}N_{15}O_{15}$
Exact Mass: 1263,6
Mol. Wt.: 1264,39

The linear peptide $N^\alpha$-Ns-$N^\delta$-Alloc-D-Orn-R(Pbf)-Nal-G was synthesized with standard Fmoc peptide chemistry following general protocols for resin-attachment (1.) of Gly and repeated Fmoc deprotection (2.) and attachment of the following (protected) amino acid (3.). Subsequently the Orn $N^\alpha$ was N-methylated (4.), Alloc cleaved (5.), 4-(Fluorenylmethyloxycarbonylamino)-benzoic acid attached (3.), Fmoc cleaved (2.), Fmoc-Gly attached (6.), Fmoc cleaved (2.), and tris(t-Bu)DOTA attached (6.). After this modification of the side-chain the Orn $N^\alpha$-Ns group was cleaved (7.), Fmoc-Tyr (tBu) attached (6.), its Fmoc group cleaved (2.) and the resulting branched peptide cleaved from the resin (8.). The peptide was cyclized (9.), deprotected (10.) and purified by RP-HPLC. The metal chelates of the pure peptides were obtained by labeling with Indium (11.) or Gallium (12.) with subsequent RP-HPLC purification.

yorn'(Aba, betaAla, DOTA)RNalG

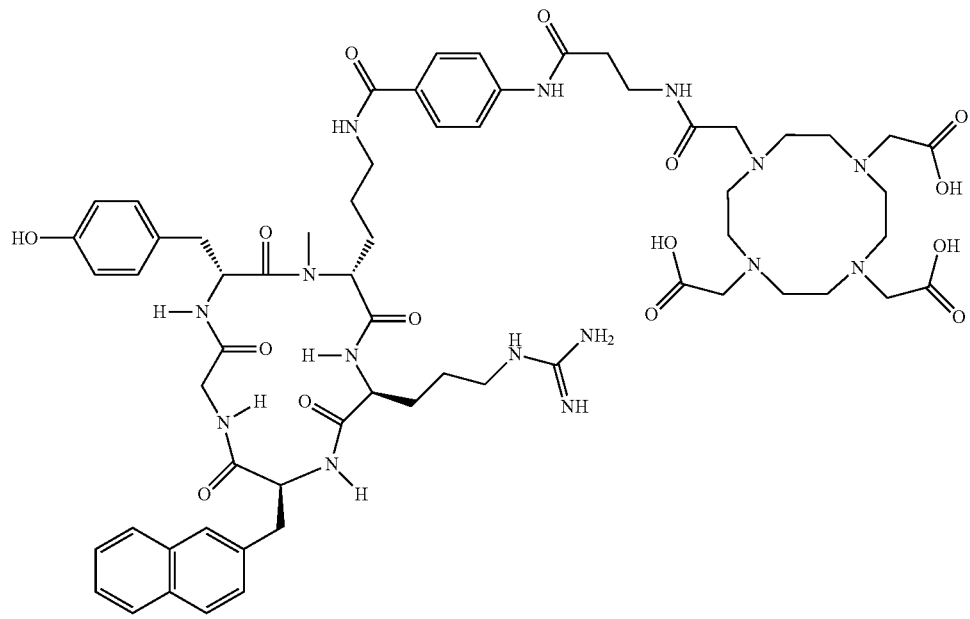

yorn'(Aba, betaAla, DOTA)RNalG
cyclo(-D-Tyr-(α-methyl, δ-4-aminobenzoic acid, beta-alanine, DOTA)-D-Orn-R-Nal-G)
$C_{62}H_{83}N_{15}O_{15}$
Exact Mass: 1277,62
Mol. Wt.: 1278,41

The linear peptide $N^\alpha$-Ns-$N^\delta$-Alloc-D-Orn-R(Pbf)-Nal-G was synthesized with standard Fmoc peptide chemistry following general protocols for resin-attachment (1.) of Gly and repeated Fmoc deprotection (2.) and attachment of the following (protected) amino acid (3.). Subsequently the Orn $N^\alpha$ was N-methylated (4.), Alloc cleaved (5.), 4-(Fluorenylmethyloxycarbonylamino)-benzoic acid attached (3.), Fmoc cleaved (2.), Fmoc-betaAla attached (6.), Fmoc cleaved (2.), and tris(t-Bu)DOTA attached (6.). After this modification of the side-chain the Orn $N^\alpha$-Ns group was cleaved (7.), Fmoc-Tyr(tBu) attached (6.), its Fmoc group cleaved (2.) and the resulting branched peptide cleaved from the resin (8.). The peptide was cyclized (9.), deprotected (10.) and purified by RP-HPLC. The metal chelates of the pure peptides were obtained by labeling with Indium (11.) or Gallium (12.) with subsequent RP-HPLC purification.

yorn'(Aba, Ava, DOTA)RNalG

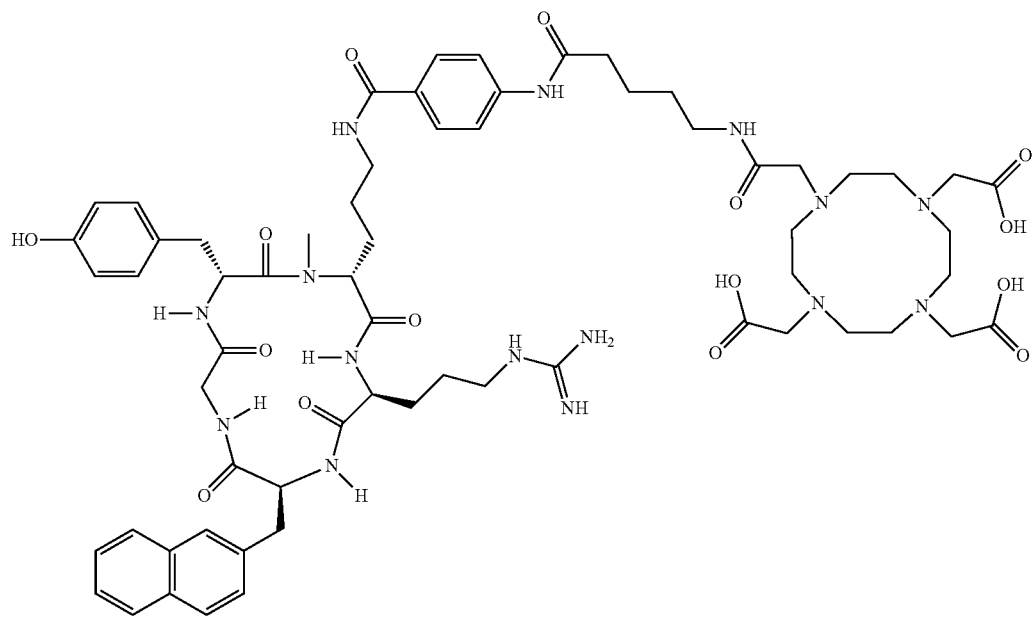

yorn'(Aba, Ava, DOTA)RNalG
cyclo(-D-Tyr-(α-methyl, δ-4-aminobenzoic acid, 5-aminovaleric acid, DOTA)-D-Orn-R-Nal-G)
$C_{64}H_{87}N_{15}O_{15}$
Exact Mass: 1305,65
Mol. Wt.: 1306,47

The linear peptide $N^\alpha$-Ns-$N^\delta$-Alloc-D-Orn-R(Pbf)-Nal-G was synthesized with standard Fmoc peptide chemistry following general protocols for resin-attachment (1.) of Gly and repeated Fmoc deprotection (2.) and attachment of the following (protected) amino acid (3.). Subsequently the Orn $N^\alpha$ was N-methylated (4.), Alloc cleaved (5.), 4-(Fluorenylmethyloxycarbonylamino)-benzoic acid attached (3.), Fmoc cleaved (2.), Fmoc-Ava attached (6.), Fmoc cleaved (2.), and tris(t-Bu)DOTA attached (6.). After this modification of the side-chain the Orn $N^\alpha$-Ns group was cleaved (7.), Fmoc-Tyr(tBu) attached (6.), its Fmoc group cleaved (2.) and the resulting branched peptide cleaved from the resin (8.). The peptide was cyclized (9.), deprotected (10.) and purified by RP-HPLC. The metal chelates of the pure peptides were obtained by labeling with Indium (11.) or Gallium (12.) with subsequent RP-HPLC purification.

yorn'(Aba, Ahx, DOTA)RNalG

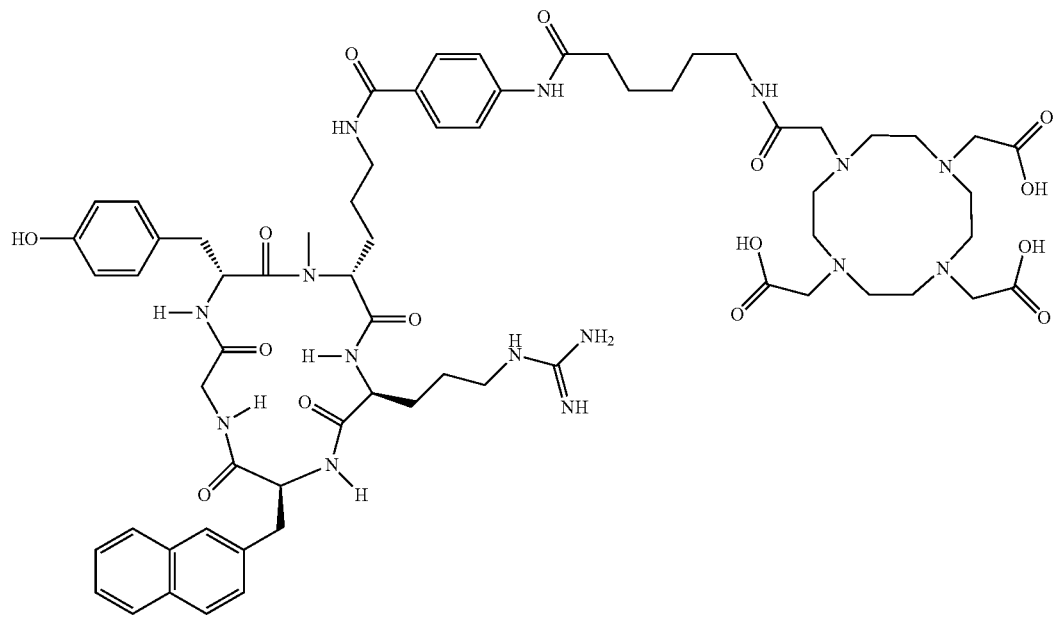

yorn'(Aba, Ahx, DOTA)RNalG
cyclo(-D-Tyr-(α-methyl, δ-4-aminobenzoic acid, 6-aminohexanoic acid, DOTA)-D-Orn-R-Nal-G)
$C_{65}H_{89}N_{15}O_{15}$
Exact Mass: 1319,67
Mol. Wt.: 1320,49

The linear peptide $N^\alpha$-Ns-$N^\delta$-Alloc-D-Orn-R(Pbf)-Nal-G was synthesized with standard Fmoc peptide chemistry following general protocols for resin-attachment (1.) of Gly and repeated Fmoc deprotection (2.) and attachment of the following (protected) amino acid (3.). Subsequently the Orn $N^\alpha$ was N-methylated (4.), Alloc cleaved (5.), 4-(Fluorenylmethyloxycarbonylamino)-benzoic acid attached (3.), Fmoc cleaved (2.), Fmoc-Ahx attached (6.), Fmoc cleaved (2.), and tris(t-Bu)DOTA attached (6.). After this modification of the side-chain the Orn $N^\alpha$-Ns group was cleaved (7.), Fmoc-Tyr(tBu) attached (6.), its Fmoc group cleaved (2.) and the resulting branched peptide cleaved from the resin (8.). The peptide was cyclized (9.), deprotected (10.) and purified by RP-HPLC. The metal chelates of the pure peptides were obtained by labeling with Indium (11.) or Gallium (12.) with subsequent RP-HPLC purification.

yorn'(Ava, Ava, DOTA)RNalG

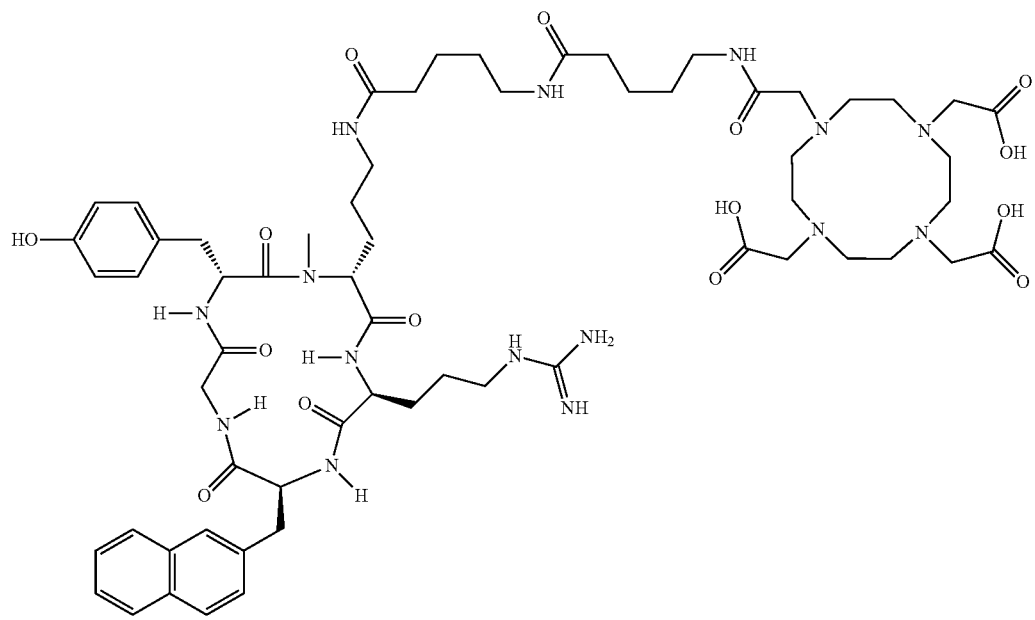

yorn'(Ava, Ava, DOTA)RNalG
cyclo(-D-Tyr-(α-methyl, δ-5-aminovaleric acid, 5-aminovaleric acid, DOTA)-D-Orn-R-Nal-G)
$C_{62}H_{91}N_{15}O_{15}$
Exact Mass: 1285,68
Mol. Wt.: 1286,48

The linear peptide $N^\alpha$-Ns-$N^\delta$-Alloc-D-Orn-R(Pbf)-Nal-G was synthesized with standard Fmoc peptide chemistry following general protocols for resin-attachment (1.) of Gly and repeated Fmoc deprotection (2.) and attachment of the following (protected) amino acid (3.). Subsequently the Orn $N^\alpha$ was N-methylated (4.), Alloc cleaved (5.), Fmoc-Ava attached (3.), Fmoc cleaved (2.), Fmoc-Ava attached (3.), Fmoc cleaved (2.), and tris(tBu)DOTA attached (6.). After this modification of the side-chain the Orn $N^\alpha$-Ns group was cleaved (7.), Fmoc-Tyr(tBu) attached (6.), its Fmoc group cleaved (2.) and the resulting branched peptide cleaved from the resin (8.). The peptide was cyclized (9.), deprotected (10.) and purified by RP-HPLC. The metal chelates of the pure peptides were obtained by labeling with Indium (11.) or Gallium (12.) with subsequent RP-HPLC purification.

yorn'(G, Trigas, DOTA)RNalG

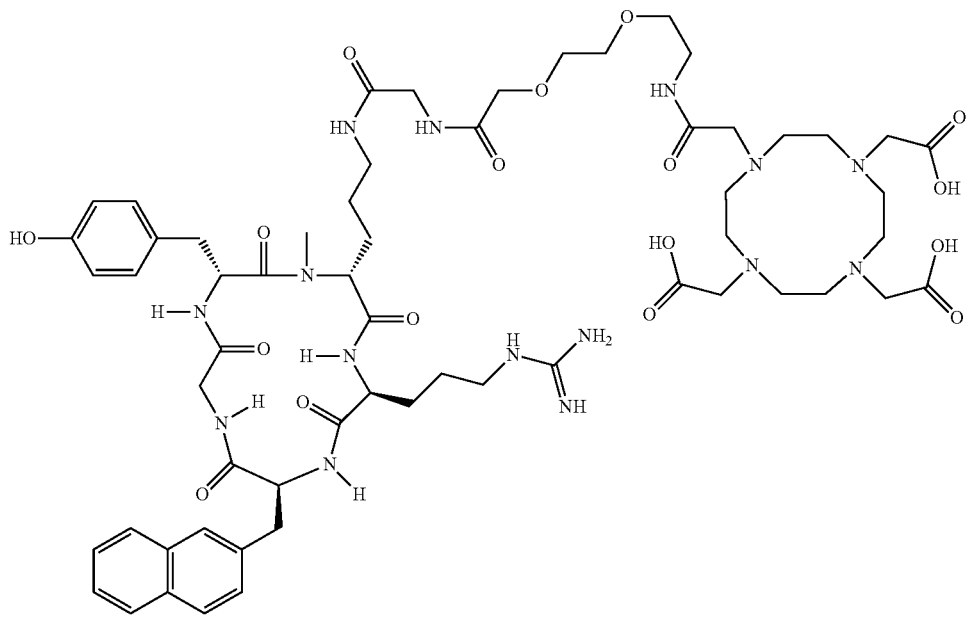

yorn'(G, Trigas, DOTA)RNalG
cyclo(-D-Tyr-(α-methyl, δ-G, 2-(2-(2-aminoethoxy)ethoxy)acetic acid, DOTA)-D-Orn-R-Nal-G)
$C_{60}H_{87}N_{15}O_{17}$
Exact Mass: 1289,64
Mol. Wt.: 1290,42

The linear peptide $N^{\alpha}$-Ns-$N^{\delta}$-Alloc-D-Orn-R(Pbf)-Nal-G was synthesized with standard Fmoc peptide chemistry following general protocols for resin-attachment (1.) of Gly and repeated Fmoc deprotection (2.) and attachment of the following (protected) amino acid (3.). Subsequently the Orn $N^{\alpha}$ was N-methylated (4.), Alloc cleaved (5.), Fmoc-Gly attached (3.), Fmoc cleaved (2.), Fmoc-Trigas attached (6.), Fmoc cleaved (2.), and tris(tBu)DOTA attached (6.). After this modification of the side-chain the Orn $N^{\alpha}$-Ns group was cleaved (7.), Fmoc-Tyr(tBu) attached (6.), its Fmoc group cleaved (2.) and the resulting branched peptide cleaved from the resin (8.). The peptide was cyclized (9.), deprotected (10.) and purified by RP-HPLC. The metal chelate of the pure peptide was obtained by labeling with Indium (11.) and subsequent RP-HPLC purification.

Biological Assays

Receptor Binding Assays.

For receptor binding assays cells may be resuspended in PBS/0.2% BSA. A total of 200 µl of the suspension containing 400,000 Jurkat cells may be incubated with 25 µl of the tracer solution (containing 3.1 kBq, approx. 0.1 nM) and 25 µl of the diluent or the competitor at different concentrations. For determination of $IC_{50}$ values, cyclo(-D-Tyr$^1$-[$^{124}$I]-Arg$^2$-Arg$^3$-Nal$^4$-Gly$^5$) may be used as a tracer. Nonspecific binding may be determined in the presence of 1 µM cold cyclo(-D-Tyr$^1$-[$^{127}$I]-Arg$^2$-Arg$^3$-Nal$^4$-Gly$^5$). After shaking for 2 h at room temperature, the incubation may be terminated by centrifugation at 1300 rpm for 5 min, Cell pellets may be washed once with cold PBS followed by a second centrifugation step. Cell bound radioactivity may be determined by using a gamma counter. Experiments may be repeated 2-3 times in triplicates. $IC_{50}$ values of the compounds may be calculated by nonlinear regression using GraphPad Prism (GraphPad Prism 4.0 Software, Inc., San Diego, Calif., USA). Each data point may be the average of three determinations.

Detailed Medical Examples

Labelling of CPCR4-Ligands with $^{68}$Ga

Binding Studies

The affinity of peptides to human-CXCR4 was tested in binding studies. $^{125}$I-CPCR4 was used as radiotracer, the cold reference peptides as competitors.

Description

The suitability of e.g. CPCR4 as a CXCR4-radioligand was tested first at Jurkat cells that endogenously express the CXCR4 receptor.

Cells were resuspended in 0.2% PBS/0.2% BSA. A total of 200 µL of the suspension containing 2×10$^6$ Jurkat cells/ml or 400000 cell/200 µl were incubated with 25 µL of the tracer solution (containing 100,000 cpm, approx. 0.1 nM) and 25 µL of competitor dissolved in ultra pure H$_2$O or, if necessary, up to 20% DMSO at different concentrations. The tracer concentration was varied from 5 to 500 pM. Nonspecific binding was determined in the presence of 1 µM cold CPCR4. Nonspecific binding is present in case of a total blockage upon addition of 1 µM cold, unlabelled CPCR4 to the tracer.

After 2 h at room temperature, the incubation was terminated by centrifugation at 2000 rpm for 5 min. Cell pellets were washed once with 400 µL cold PBS. Cell bound radioactivity was determined by using a gamma counter. Experiments were repeated three times in triplicates. $IC_{50}$ values of the peptides were calculated by nonlinear regression using GraphPad Prism (GraphPad Prism 4.0 Software, San Diego, Calif., USA).

Preparing of the $^{125}$I-CPCR4-Stock-Solution

50 μg Iodogen iodination reagent ("IODO-GEN Iodination Reagent", Perbio Science Deutschland GmbH) was dissolved in 50 μl dry dichloromethane, transferred into a 1.5 ml Eppendorf tube, carefully dried with argon gas. Tubes prepared in the aforementioned manner were stored at −20° C.

20 μg of the cyclic pentapeptide cyclo(D-Tyr-Arg-Arg-Nal-Gly) ("CPCR4-peptide") were dissolved in 100 μl phosphate buffered saline (PBS) and transferred into an Iodogen coated cup. Approximately 37-74 MBq sodium $^{125}$I-iodide in 10 μl-200 μl 0.04 M NaOH solution was added (also feasible are e.g. 185 MBq sodium $^{125}$I-iodide in 50 μl 0.04 M NaOH solution). After reaction at room temperature for 15 min the solution was removed from the Iodogen cup and the peptide purified by radio-HPLC (UV-detection at 220 nm, NaI well counter, Nucleosil 100-5 C18 column, eluent A=0.1% TFA in water; eluent B=0.1% TFA in acetonitril (MeCN), gradient: 20% B 35% B in 20 min; flow rate: 1 ml/min; product: k'=7.25; k' parent peptide 5.1. Quality control was carried out on a second HPLC using otherwise identical conditions. After removal of solvents the product was diluted with ethanol and stored for up to 2 months. For the binding assays, a precalculated volume of the stock solution was diluted with PBS to yield a 2 mL solution with an activity concentration of 100,000 cpm/25 μL.

Preparing of Jurkat Cell Solution

Confluent Jurkat cells were cultured in RPMI 1640 Medium with 10% Nu-serum. After centrifugation of 3-4 culture flasks, the supernatant were discarded and the aggregated pellets were resuspended in 40 mL PBS. The cell concentration was determined with a Casy cell counter (500 cell suspension in 10 ml Casy solution (Innovartis AG, Casy technology). The desired cell suspension volume was transferred into an Eppendorf tube, centrifuged, the supernatant was discarded and the pellet was resuspended in 20 ml 0.2% PBS-BSA-buffer.

Cell Test Procedure:

The competition assay was carried out at competitor concentrations of $10^{-11}$ to $10^{-5}$ M. To these tubes 200 μl of the prepared Jurkat-cell solution was added followed by 25 μl $^{125}$I-CPCR4 stock solution. Subsequently, the tubes were placed on a shaker for 2 h (200 mot/min). Thereafter, the tubes were centrifuged for 5 min at 2000 rpm and the supernatant carefully removed. The pellets were washed with 400 μl PBS and the tubes were again centrifuged for 5 min at 2000 rpm. After the supernatant was carefully removed, the tubes were measured in a gamma counter. All data were analyzed with a suitable software package, i.e. GraphPad Prism 4 with the following parameters: Equation: Sigmoidal dose-response, Y=Bottom+(Top−Bottom)/(1+10^((Log EC50−X))); X is the logarithm of concentration; Y is the response; Y starts at bottom and goes to top with a sigmoid shape.

Exemplary Binding Study A

CPCR4-2 (yorn'(AMBS, DOTA, Ga)RNalG); IC$_{50}$=4.78±0.73 nM (n=4)

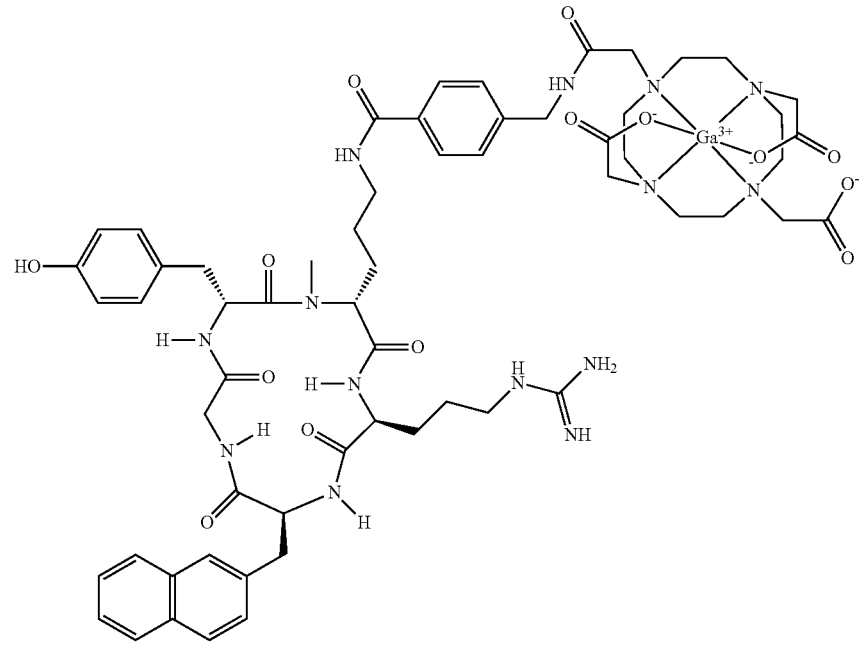

Labelling with $^{68}$Ga:

Gallium-68 (β$^+$=89%, t$_{1/2}$=68.1 min, E$_{β+max}$ 1.90 MeV) was eluted from a commercially available Ge-68/Ga-68 generator by diluted HCl. The collected eluate was fractionated and one fraction of approx. 1-1.2 mL with approx. 80% of the entire eluted activity was used for labelling of yorn'(AMBS, DOTA)RNalG using a commercially available fully automated labelling module (Gallelut-Synthesizer, Scintomics GmbH, Fürstenfeldbruck, Germany). Briefly, the eluate was buffered with a suitable amount of HEPES (4-(2-hydroxyethyl)-1-piperazineethanesulfonic acid) buffer and 20 μg of the peptide. After reaction for 5 min at 95° C., the solution was passed through a water RP-cartridge. To remove residual and non-complexed Ga-68 radioactivity, the cartridge was flushed with 10 mL water. Finally, the labelled peptide was removed from the cartridge with 500 μL ethanol, followed by 10 mL phosphate buffered saline. These solutions were directly passed through a sterile filter into a sterile vial.

In some cases, the aforementioned cartridge purification was replaced by a HPLC-purification of the labelled peptide (radio HPLC—conditions: Sykam HPLC system, Ray-test software system, Linear UVIS 200 spectrophotometer, NaI-well type activity detector; Multosphere 100 RP18—5μ column; eluent A=0.2 M ammonium acetate (15.461 g in 1 l $H_2O$ Millipore), eluent B=methanol; 49%-60% (B) in 20 min; flow rate: 5 ml/min; product at 11.0-12.5 min).

Quality control of product was carried out by radio thin layer chromatography on Silica gel 60-plates using 0.5 μl of product solution on 2 different TLC systems: a) eluent TLC-1: 0.1 M sodium citrate (5.882 g tri-sodium citrate dihydrate in 200 ml ultrapure water); eluent TLC-2: (1/1, v/v) methanol/1M ammonium acetate (15.461 g ammonium acetate in 200 ml ultra pure water). Using the TLC method 1, the product and Ga-colloid stay at the starting point, whereas free $Ga^{3+}$ moves with front. Using the TLC method 2, uncomplexed Ga-species stay at starting point, whereas the labelled peptide moves with front.

Figure 2:
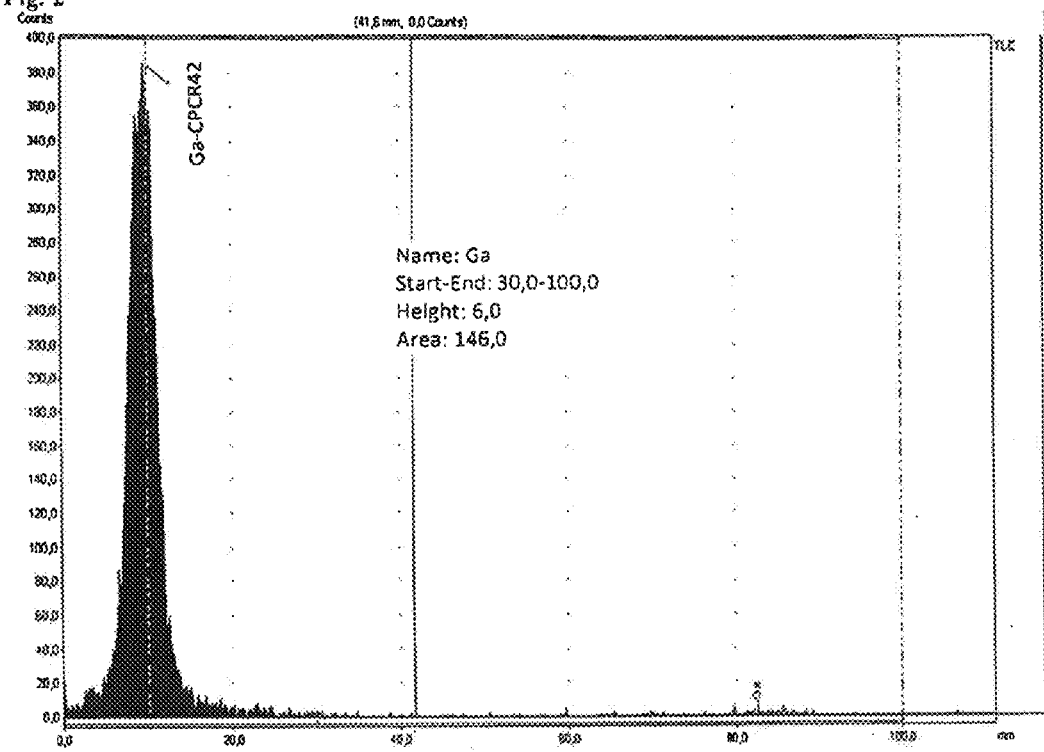
FIG. 2 shows an exemplary radio-TLC profile under TLC condition 1; start (at 1 cm): Ga-CPCR4-2, 98.18% purity, non-complexed Ga-68 at the front (8-9 cm): 1.78%
Figure 3:
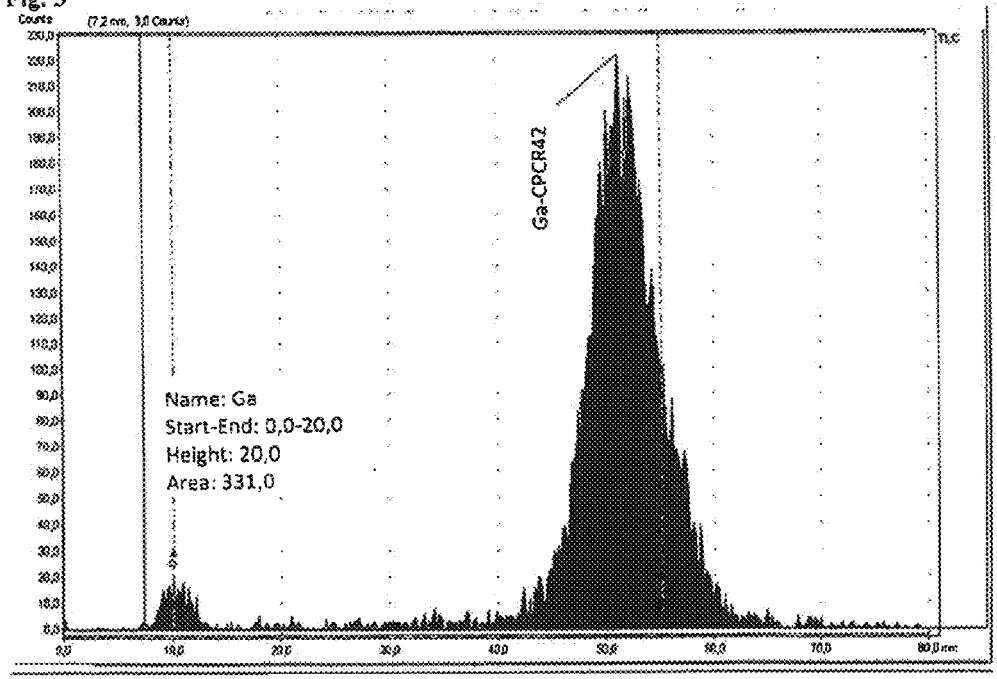
FIG. 3 shows an exemplary radio-TLC profile under TLC condition 2; start (at 1 cm): non-complexed Ga-68, 3.89%, at the front Ga-CPCR4-2 (4.5-6.5 cm): 96.11% purity.

FIGS. 2 and 3 show radio-TLC profiles. FIG. 2 shows an exemplary radio-TLC profile under TLC condition 1; start (at 1 cm): Ga-CPCR4-2, 98.18% purity, non-complexed Ga-68 at the front (8-9 cm): 1.78%. FIG. 3 shows an exemplary radio-TLC profile under TLC condition 2; start (at 1 cm): non-complexed Ga-68, 3.89%, at the front Ga-CPCR4-2 (4.5-6.5 cm): 96.11% purity.

After the quality control via TLC was finished, the solvent of the product solution was completely removed by evaporation under reduced pressure and the product dissolved in isotonic saline/5% ethanol.

Labelling with Lu-177

[$^{177}$Lu]CPCR4-2 was prepared by dissolving 20 μg of CPCR4-2 in 300 μL sodium acetate buffer (0.4 mol/L, pH 5.0) and by incubation with $^{177}LuCl_3$ for 1 hour at room temperature. Subsequently, the radiometalated peptide was purified using a water RP-cartridge (see the above described procedure for $^{68}$Ga-CPCR4-2).

Labelling with In

Labelling of e.g. DOTA ligands with In is known to the skilled person. It may e.g. essentially be performed as described above.

Binding Data of Exemplary Compounds of the Invention

The binding data ($IC_{50}$ values) of exemplary compounds of the invention are depicted in the following:

TABLE V

Binding Data

| No. | Abbreviation | $IC_{50}$ [nM] |
|---|---|---|
| 1 | yorn'(ABS, betaAla, DOTA)RNalG | 37.6 ± 14.7 |
| 2 | yorn'(ABS, Ahx, DOTA, In)RNalG | 26.5 ± 22.6 |
| 3 | yorn'(ABS, Ahx, DOTA, Ga)RNalG | 30.3 ± 6.52 |
| 4 | yorn'(ABS, betaAla, DOTA, In)RNalG | 30.4 ± 3.68 |
| 5 | yorn'(ABS, betaAla, DOTA, Ga)RNalG CPCR4-1 | 33.3 ± 3.68 |
| 6 | yorn'(ABS, AVS, DOTA, In)RNalG | 40.9 ± 21.6 |
| 7 | yorn'(ABS, AVS, DOTA, Ga)RNalG | 14.2 ± 3.01 |
| 8 | yorn'(AMBS, DOTA, In)RNalG | 44.9 ± 10.4 |
| 9 | yorn'(AMBS, DOTA, Ga)RNalG CPCR4-2 | 4.78 ± 0.73 |
| 10 | yorn'(ABS, G, DOTA)RNalG | 88.8 ± 18.4 |
| 11 | yorn'(ABS, G, DOTA, In)RNalG | 20.9 ± 3.46 |
| 12 | yorn'(ABS, G, DOTA, Ga)RNalG | 16.7 ± 3.28 |
| 13 | yorn'(ABS, DOTA, Ga)RNalG | 11.5 ± 4.4 |
| 14 | yorn'(ABS, Ahx, DOTA)RNalG | >1000 |
| 15 | yorn'(ABS, DOTA)RNalG | 334.7 |
| 16 | yorn'(ABS, DOTA, In)RNalG | 105.2 |
| 17 | yorn'(ABS, DOTA, Ga)RNalG | 11.5 ± 4.4 |
| 18 | yorn'(ABS, AVS, DOTA)RNalG | 121 ± 17 |
| 19 | yorn'(DOTA)RNalG | 807 ± 477 |
| 20 | yorn'(DOTA, In)RNalG | >1000 |
| 21 | yorn'(DOTA, Ga)RNalG | 288.9 |
| 22 | yorn'(AVS, AVS, DOTA)RNalG | >1000 |
| 23 | yorn'(AVS, AVS, DOTA, In)RNalG | 123.0 ± 25.02 |
| 24 | yorn'(AVS, AVS, DOTA, Ga)RNalG | 89.7 ± 18.3 |
| 25 | yorn'(G, Trigas, DOTA)RNalG | 903 ± 439 |
| 26 | yorn'(G, Trigas, DOTA, In)RNalG | 456.8 (n = 1) |

TABLE V-continued
Binding Data
| No. | Abbreviation | IC$_{50}$ [nM] |
|---|---|---|
| 1 | yorn'(ABS, betaAla, DOTA)RNalG | 37.6 ± 14.7 |
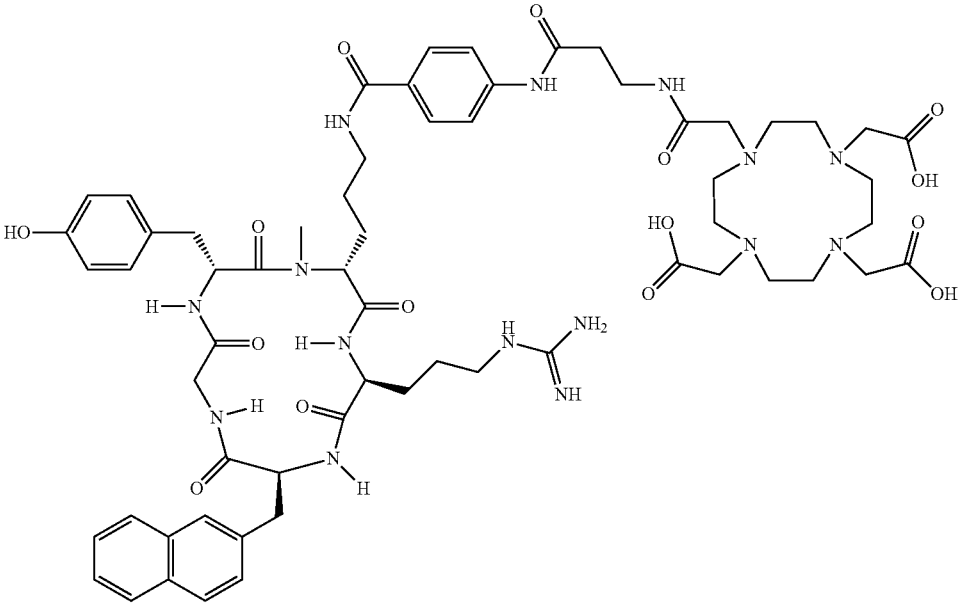 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)c1ccc(NC(=O)CCNC(=O)CN2CCN(CC(=O)O)CCN(CC(=O)O)CCN(CC(=O)O)CC2)cc1]
| | | |
|---|---|---|
| 2 | yorn'(ABS, Ahx, DOTA, In)RNalG | 26.5 ± 22.6 |
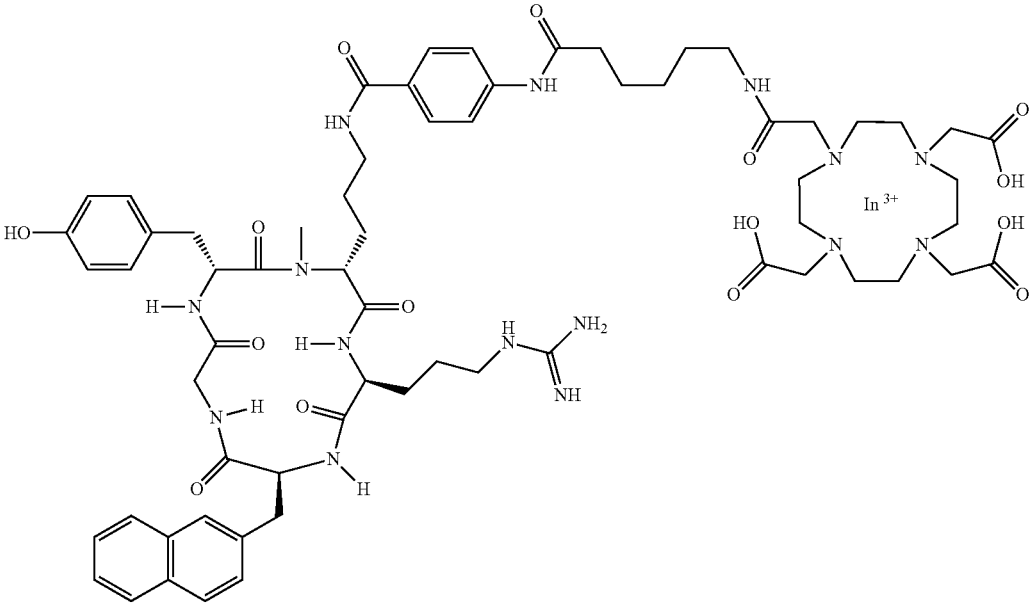

TABLE V-continued

Binding Data

| No. | Abbreviation | IC$_{50}$ [nM] |
|---|---|---|
| 3 | yorn'(ABS, Ahx, DOTA, Ga)RNalG | 30.3 ± 6.52 |
| 4 | yorn'(ABS, betaAla, DOTA, In)RNalG | 30.4 ± 3.68 |

TABLE V-continued
| Binding Data | | |
|---|---|---|
| No. | Abbreviation | IC$_{50}$ [nM] |
| 5 | yorn'(ABS, betaAla, DOTA, Ga)RNalG (CPCR4-1) | 33.3 ± 3.68 |
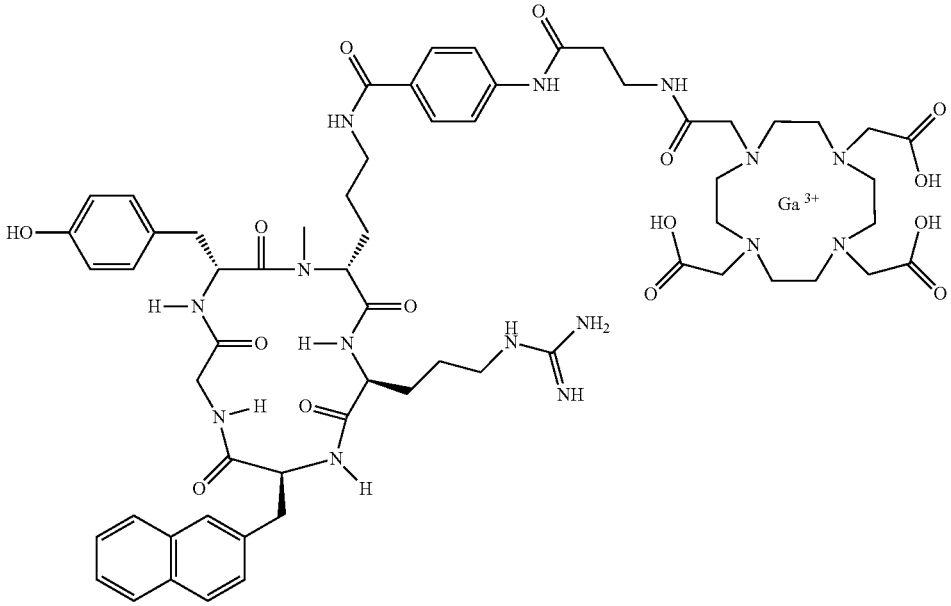 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)c1ccc(NC(=O)CCNC(=O)CN2CCN(CC(=O)O)CCN(CC(=O)O)CCN(CC(=O)O)CC2)cc1]
| | | |
|---|---|---|
| 6 | yorn'(ABS, AVS, DOTA, In)RNalG | 40.9 ± 21.6 |
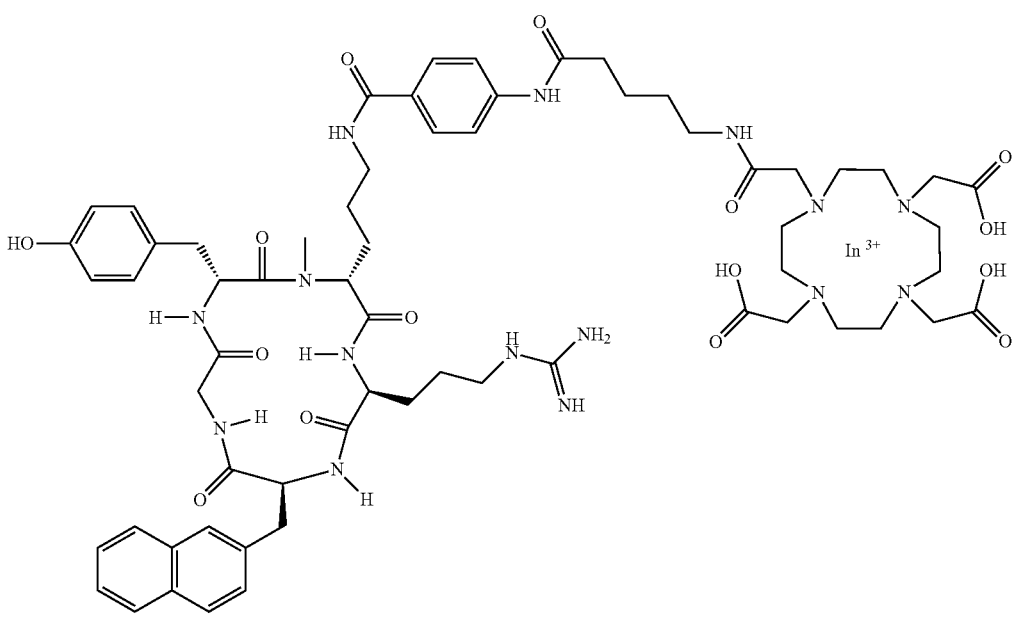 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)c1ccc(NC(=O)CCCCNC(=O)CN2CCN(CC(=O)O)CCN(CC(=O)O)CCN(CC(=O)O)CC2)cc1]

TABLE V-continued

| | Binding Data | |
|---|---|---|
| No. | Abbreviation | $IC_{50}$ [nM] |
| 7 | yorn'(ABS, AVS, DOTA, Ga)RNalG | 14.2 ± 3.01 |
| 8 | yorn'(AMBS, DOTA, In)RNalG | 44.9 ± 10.4 |

TABLE V-continued
Binding Data
| No. | Abbreviation | IC$_{50}$ [nM] |
|---|---|---|
| 9 | yorn'(AMBS, DOTA, Ga)RnalG (CPCR4-2) | 7.0 ± 4.25 |
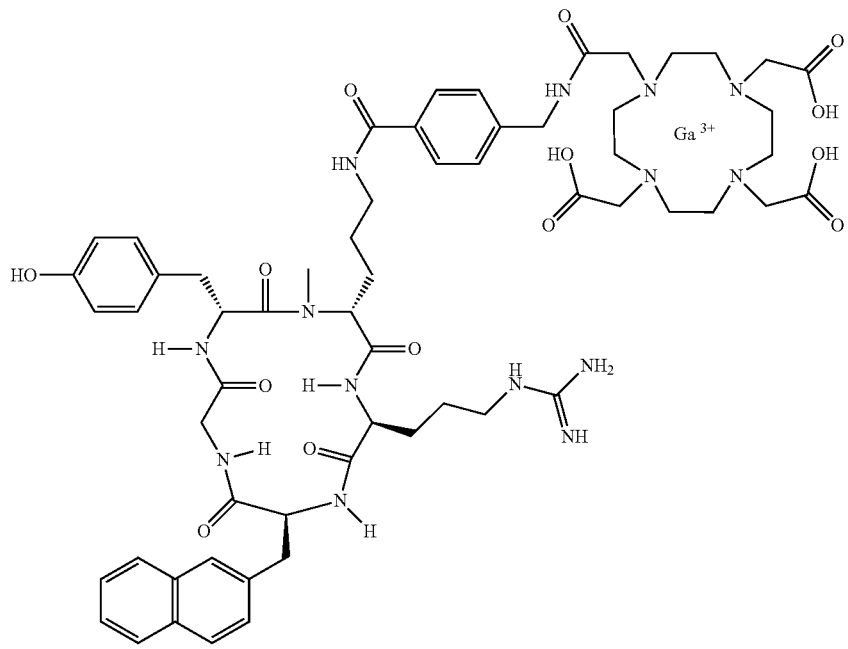 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)c1ccc(CNC(=O)CN2CCN(CC(=O)O)CCN(CC(=O)O)CCN(CC(=O)O)CC2)cc1]
| 10 | yorn'(ABS, G, DOTA)RNalG | 88.8 ± 18.4 |
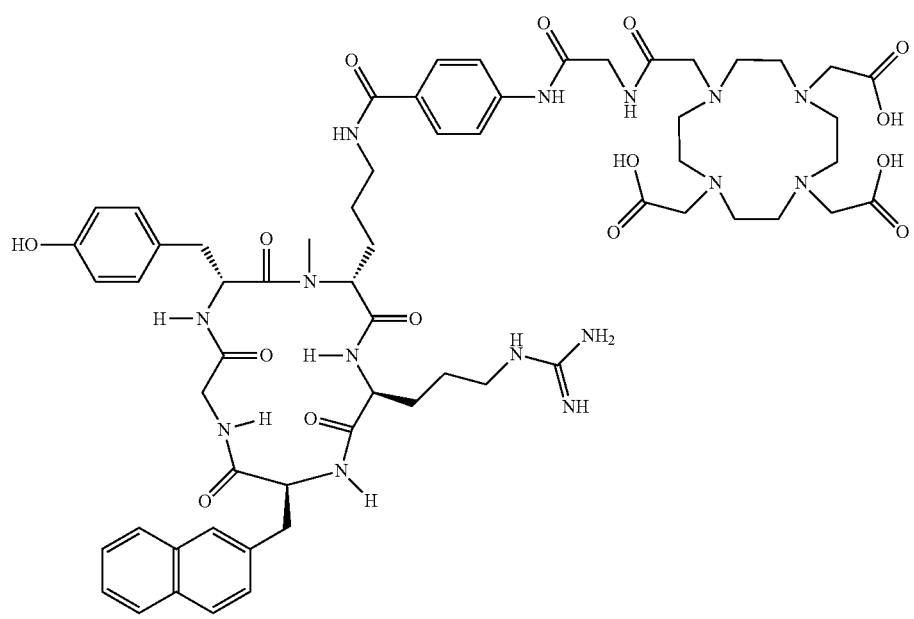 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)c1ccc(NC(=O)CNC(=O)CN2CCN(CC(=O)O)CCN(CC(=O)O)CCN(CC(=O)O)CC2)cc1]

TABLE V-continued

| Binding Data | | |
|---|---|---|
| No. | Abbreviation | IC$_{50}$ [nM] |
| 11 | yorn'(ABS, G, DOTA, In)RNalG | 20.9 ± 3.46 |
| 12 | yorn'(ABS, G, DOTA, Ga)RNalG | 116.7 ± 3.28 |

TABLE V-continued
| No. | Abbreviation | IC$_{50}$ [nM] |
|---|---|---|
| 13 | yorn'(ABS, DOTA, Ga)RNalG | 11.5 ± 4.4 |
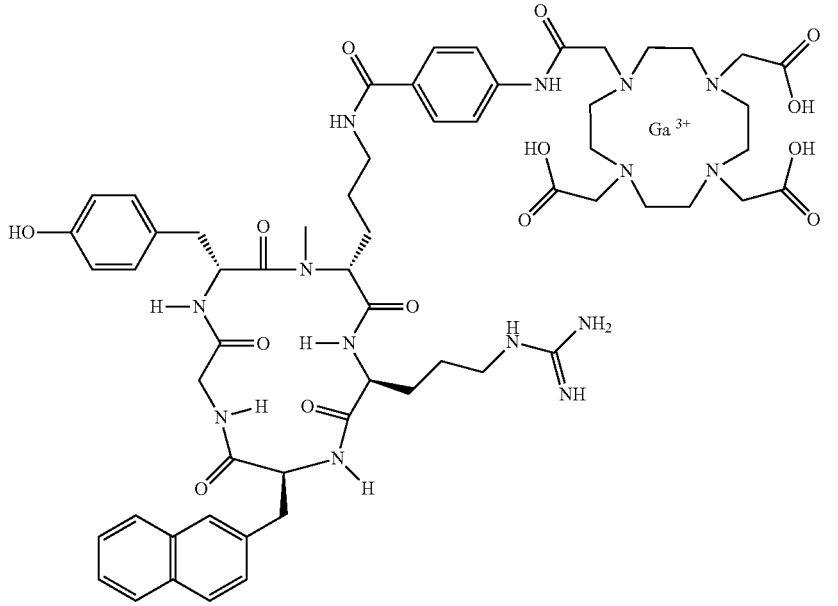 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)c1ccc(NC(=O)CN2CCN(CC(=O)O)CCN(CC(=O)O)CCN(CC(=O)O)CC2)cc1]
| 14 | yorn'(ABS, Ahx, DOTA)RNalG | >1000 |
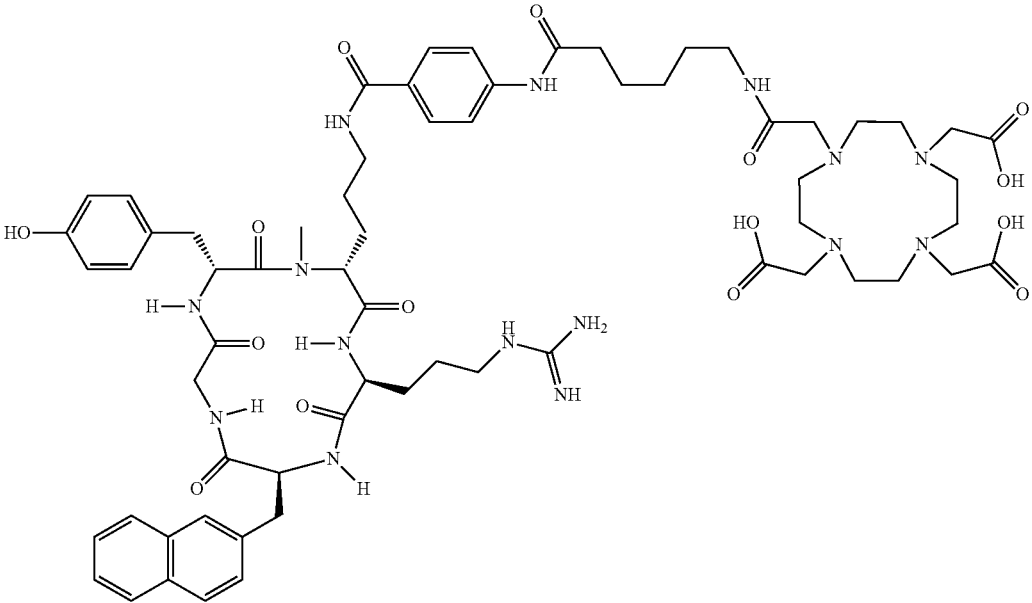 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)c1ccc(NC(=O)CCCCCNC(=O)CN2CCN(CC(=O)O)CCN(CC(=O)O)CCN(CC(=O)O)CC2)cc1]

TABLE V-continued
| No. | Abbreviation | IC$_{50}$ [nM] |
|---|---|---|
| 15 | yorn'(ABS, DOTA)RNalG | 334.7 |
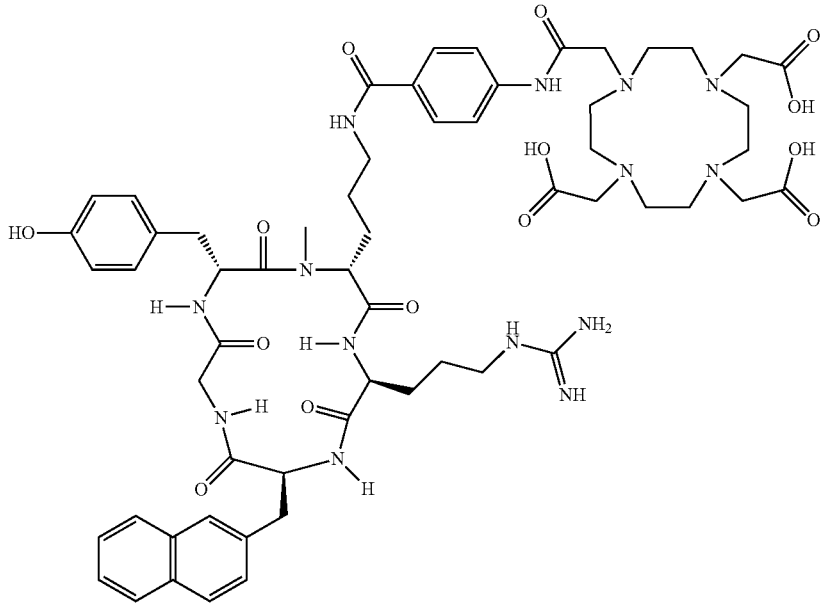 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)c1ccc(NC(=O)CN2CCN(CC(=O)O)CCN(CC(=O)O)CCN(CC(=O)O)CC2)cc1]
| 16 | yorn'(ABS, DOTA, In)RNalG | 105.2 |
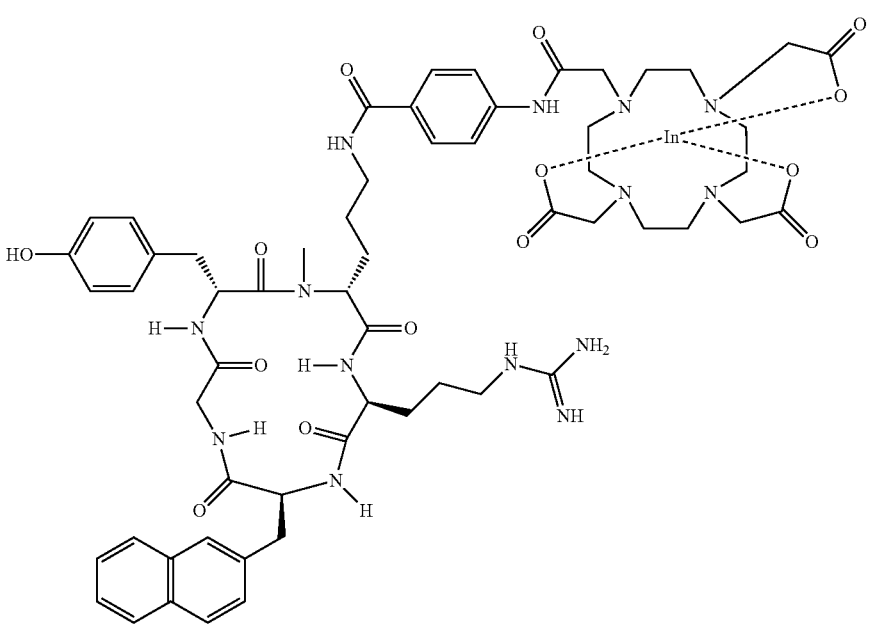

TABLE V-continued

| Binding Data | | |
|---|---|---|
| No. | Abbreviation | IC$_{50}$ [nM] |
| 17 | yorn'(ABS, DOTA, Ga)RNalG | 11.5 ± 4.4 |
| 18 | yorn'(ABS, AVS, DOTA)RNalG | 121 ± 17 |

TABLE V-continued
Binding Data
| No. | Abbreviation | IC$_{50}$ [nM] |
|---|---|---|
| 19 | yorn'(DOTA)RNalG | 807 ± 477 |
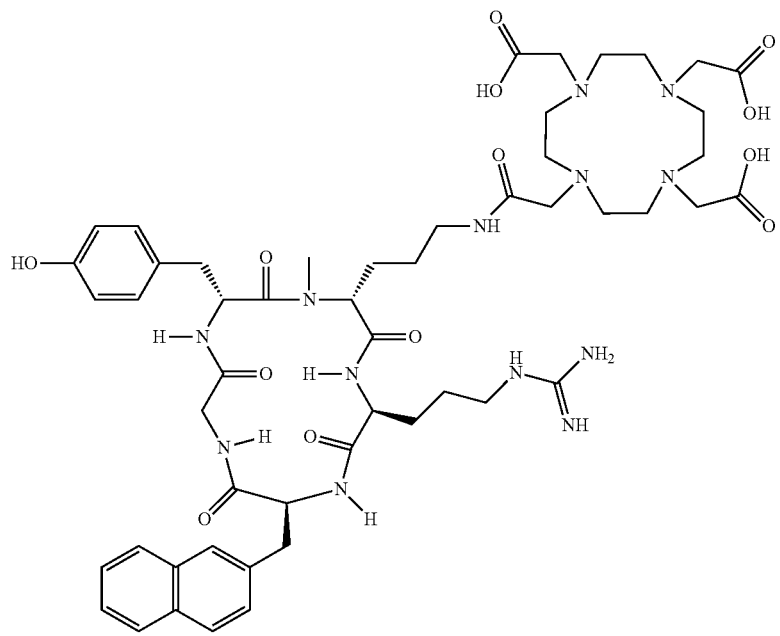 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)CN1CCN(CC(=O)O)CCN(CC(=O)O)CCN(CC(=O)O)CC1]
| | | |
|---|---|---|
| 20 | yorn'(DOTA, In)RNalG | >1000 |
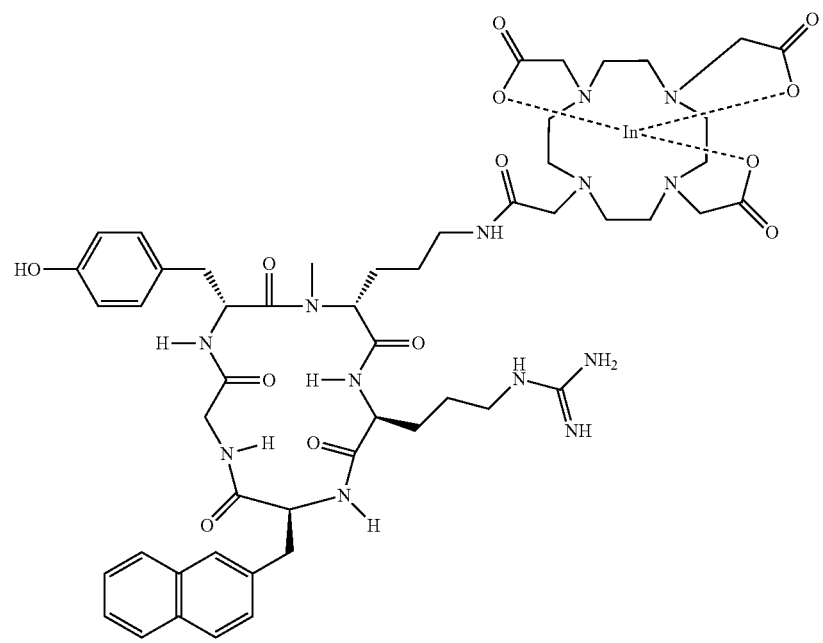

TABLE V-continued

| | Binding Data | |
|---|---|---|
| No. | Abbreviation | IC$_{50}$ [nM] |
| 21 | yorn'(DOTA, Ga)RNalG | 288.9 |
| 22 | yorn'(AVS, AVS, DOTA)RNalG | >1000 |

TABLE V-continued

Binding Data

| No. | Abbreviation | IC$_{50}$ [nM] |
|---|---|---|
| 23 | yorn'(AVS, AVS, DOTA, In)RNalG | 123.0 ± 25.02 |
| 24 | yorn'(AVS, AVS, DOTA, Ga)RNalG | 89.7 ± 18.3 |

TABLE V-continued

Binding Data

| No. | Abbreviation | $IC_{50}$ [nM] |
|---|---|---|
| 25 | yorn'(G, Trigas, DOTA)RNalG | 903 ± 439 |

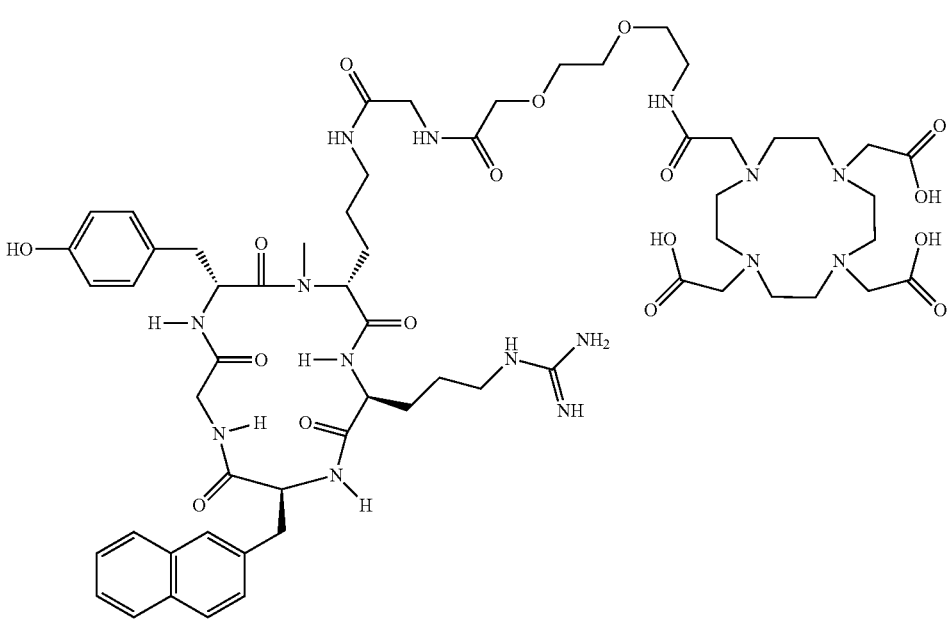 [SMILES: CN1C(=O)[C@@H](Cc2ccc(O)cc2)NC(=O)CNC(=O)[C@H](Cc2ccc3ccccc3c2)NC(=O)[C@H](CCCNC(=N)N)NC(=O)[C@H]1CCCNC(=O)CNC(=O)COCCOCCNC(=O)CN1CCN(CC(=O)O)CCN(CC(=O)O)CCN(CC(=O)O)CC1]

| 26 | yorn'(G, Trigas, DOTA, In)RNalG | 456.8 (n = 1) |

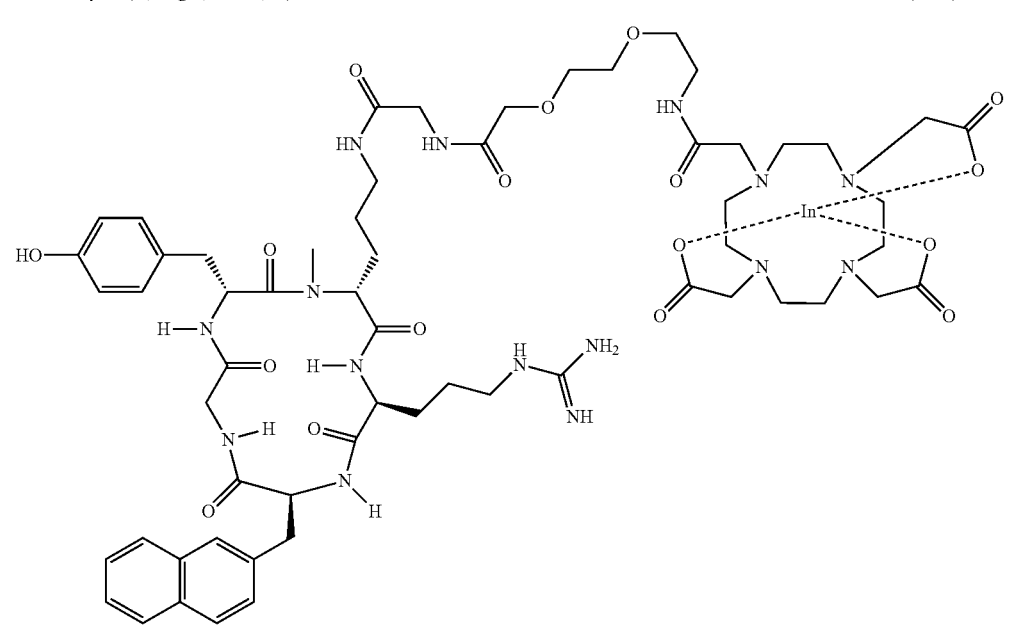

It is noted that among the above compounds comprising L-Ar, compound 14 shows a higher $IC_{50}$ value. Without intending to be bound by theory, the present inventors consider it possible that this is due to a longer alkyl chain between the aromatic moiety and the complexing agent. In any case, it is observed that upon addition of Ga or In to said compound, tight binding was observed as well (cf. compounds 2 and 3).

Evaluation of CPCR4-2 in Different Tumor Models

Table VI summarizes in vivo experiments performed in different tumor models for the evaluation of CPCR4-2, labelled with either Ga-68 or Lu-177.

For all tumor models, biodistribution studies (BD) were performed at 1 h p.i. of the $^{68}$Ga-labeled tracer, both under n.c.a. (non carrier added; n=4-5) and competition (co-injection of unlabeled CPCR4, 50 μg/mouse, n=3) conditions to evaluate binding specificity. PET and SPECT imaging studies were not conducted uniformly, but exact experimental procedures (amount of injected activity, type of camera, duration of scan etc.) are given for each respective experiment.

TABLE VI

Summary of in vivo experiments performed for the evaluation of CPCR4-2 (DOTA-peptide), labelled with either Ga-68 or Lu-177.

| No | Cell line | Human tumor type | Media & supplements | Number of injected cells | Tumor growth (days) | Tumor weight (g) |
|----|-----------|------------------|---------------------|--------------------------|---------------------|------------------|
| 1 | A431 | Melanoma | DMEM + GlutaMAX, 10% FCS | $2 \times 10^6$ | 35-63 | 0.07-1.0 |
| 2 | HT29 | Colorectal Carcinoma | DMEM, 10% FCS, 1% P/S | $1 \times 10^6$ | 33 | 0.03-1.0 |
| 3 | OH1 | Small Cell Lung Cancer | RPMI, 10% FCS, 1% L-Glutamin, 1% P/S | $5 \times 10^6$ | 35-63 | 0.4-1.0 |
| 4 | PC3 | Prostate Carcinoma | RPMI, 10% FCS, 1% P/S, 1% NEA | $1 \times 10^7$ | 30-50 | 0.01-3.1 |
| 5 | SKBR3 | Breast Cancer | DMEM, 10% FCS, 1% P/S | $3 \times 10^6$ | 63 | 0.6-0.8 |
| 6 | SUDHL4 | Lymphoma | RPMI, 10% FCS | $5 \times 10^6$ | 63 days | 0.7-3.0 g |

Methods

Cell Lines and Tissue Culture

All cell lines were maintained at 37° C., 5% $CO_2$: 95% air atmosphere and cultured in Medium with supplements (Table VI). Media and supplements were obtained from Biochrom (Berlin, Germany).

In Vivo Studies

For all in vivo studies female CD1 nu/nu mice (Charles River, Germany) were used. All animal experiments were approved by the local authorities and are in compliance with the institution guidelines.

For tumor inoculation, a suspension of cells (cell number see Table VI) in 100 μl of medium was injected subcutaneously in one of the flanks or one of the shoulders of the mice. After 4-9 weeks of tumor growth mice were used for imaging and biodistribution purposes.

Biodistribution Studies $^{68}$Ga-labeled CPCR4-2 (usually 2-3 MBq/mouse in 100 pa of PBS) was injected intravenously into the tail vein of tumor bearing mice. For competition studies, 50 μg of unlabeled CPCR4 in 50 μl of PBS were co-injected. The animals were sacrificed and dissected at 1 h p.i. Organs of interest were removed and radioactivity was counted in weighted tissue samples using a 1480 Wizard3 gamma counter from Wallac (Turku, Finland). Data are represented as % injected dose per gram tissue (% iD/g) and are means±SD (n=3-5).

Results of biodistribution studies and imaging experiments are shown in FIGS. 4 to 18.

Results

Figure 4:
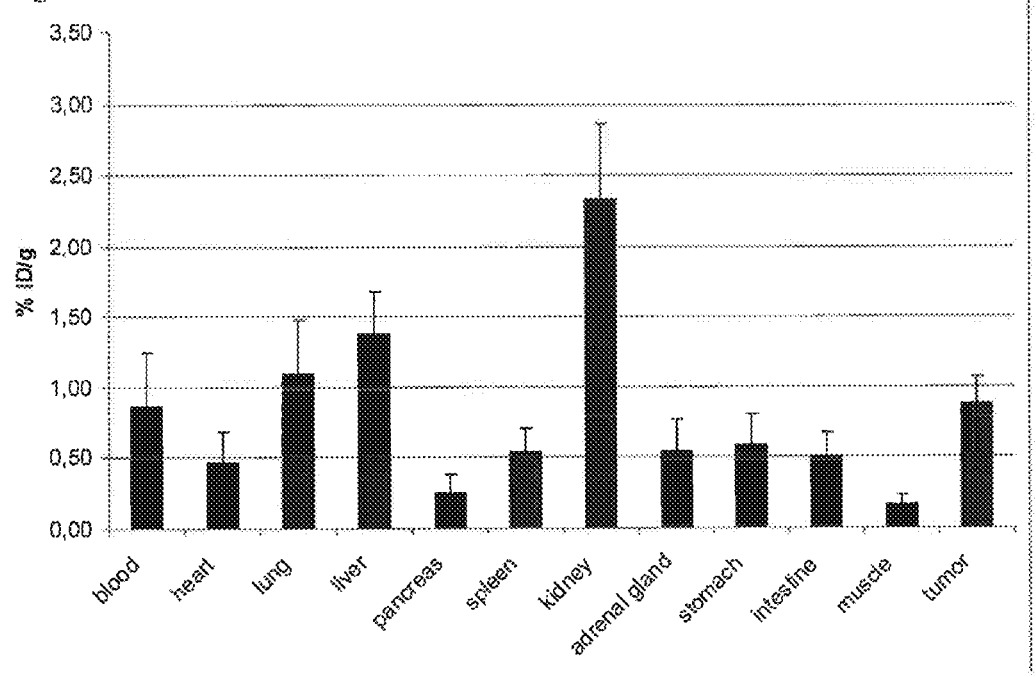
FIG. 4 shows biodistribution of [$^{68}$Ga]CPCR4-2 in A431 tumor bearing CD1 nu/nu mice at 1 h p.i.
Figure 5:
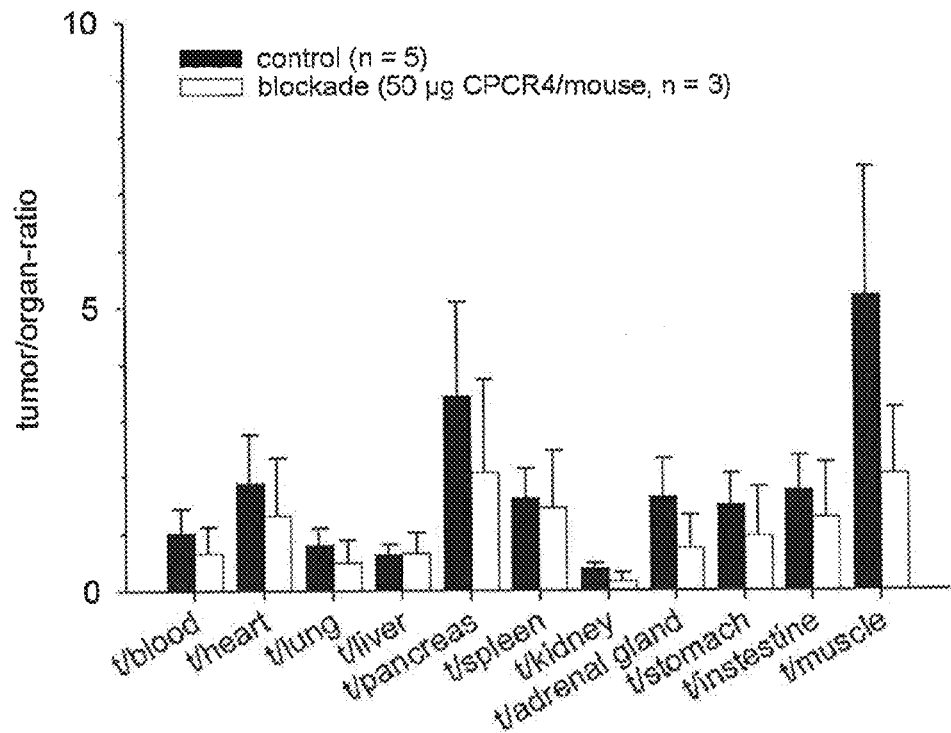
FIG. 5 shows tumor-to-organ ratios of yorn'(AMBS-[$^{68}$Ga]DOTA) RNalG (A431 tumor bearing CD-1 nude, 60 min p.i., n=3-5.
Figure 6:
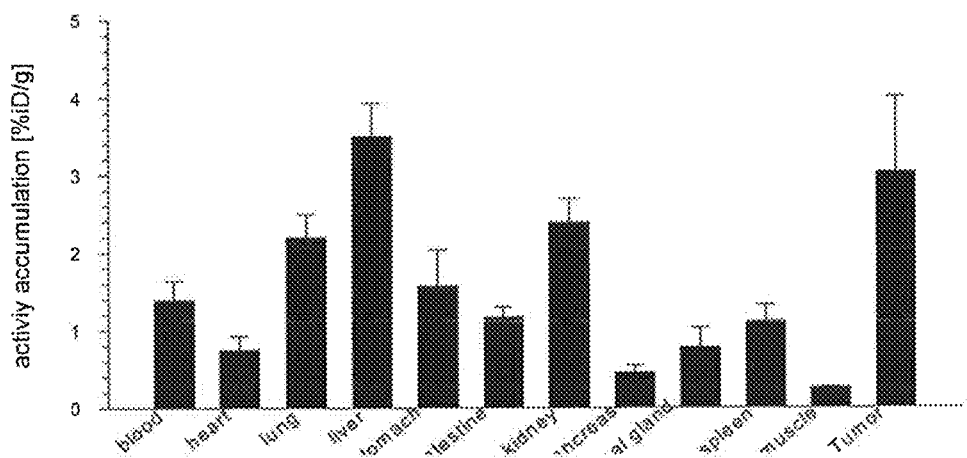
FIG. 6 shows biodistribution of [$^{125}$I]yorn'(AMBS-DOTA(Ga))RNalG ([$^{125}$I]Ga-CPCR4-2) in HT-29 tumor bearing CD1 nu/nu mice at 60 min p.i., n=4.
Figure 7:
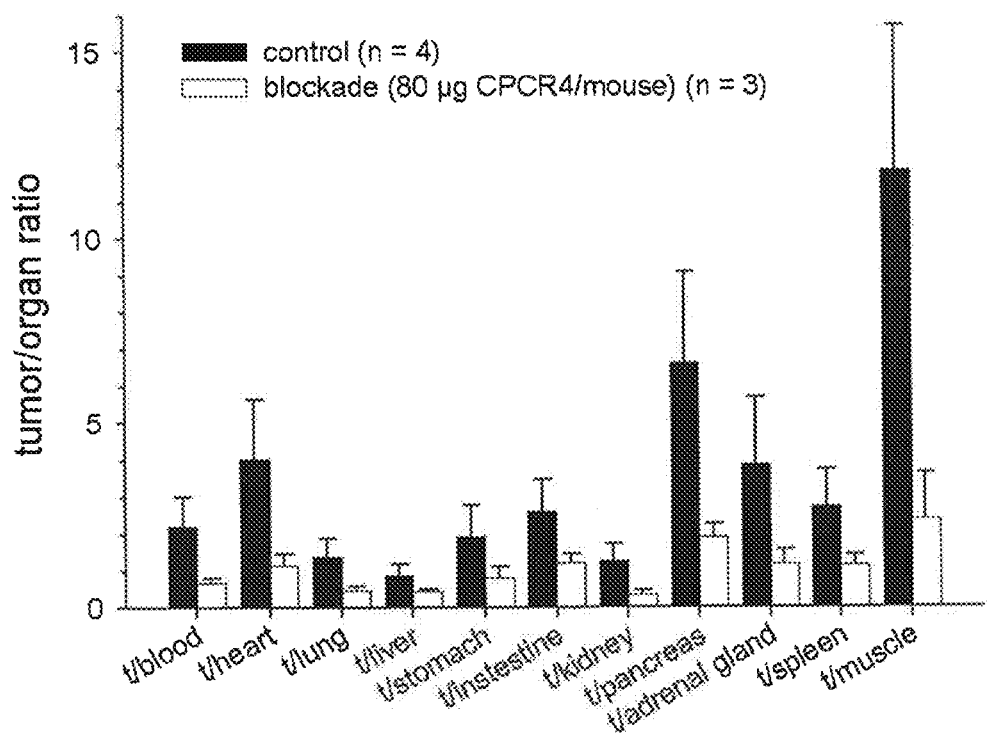
FIG. 7 shows tumor-to-organ ratios of [$^{125}$I]yorn'(AMBS-DOTA(Ga))RNalG (HT-29 tumor bearing CD1 nude mice, 60 min p.i., n=4).
Figure 8:
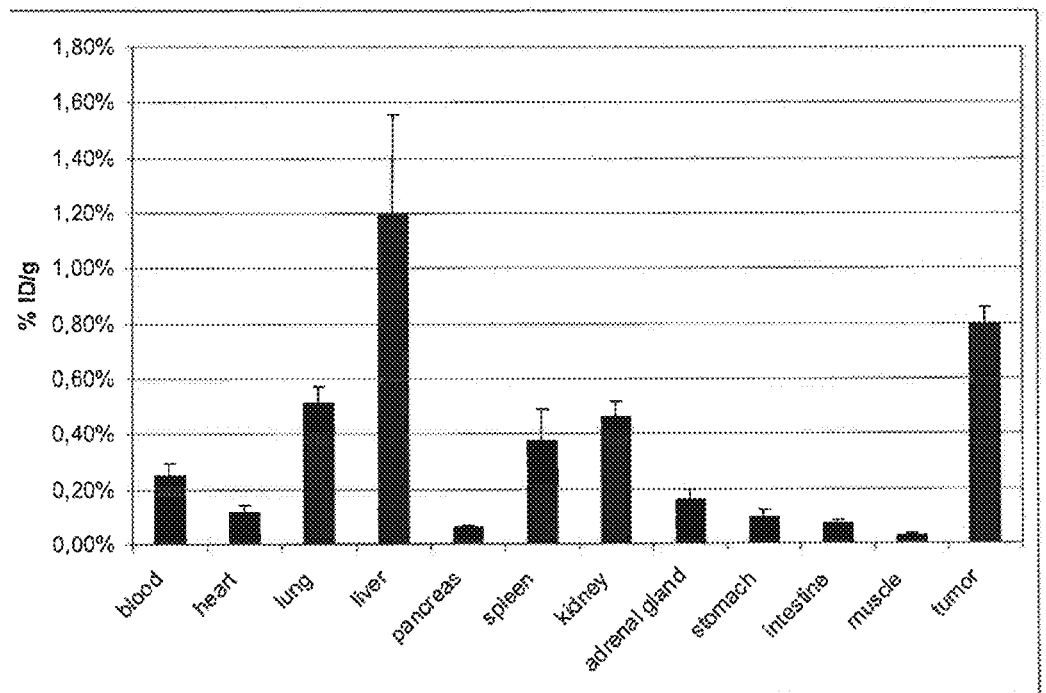
FIG. 8 shows biodistribution of [$^{68}$Ga]CPCR4-2 in OH-1 tumor bearing CD1 nu/nu mice at 1 h p.i.
Figure 9:
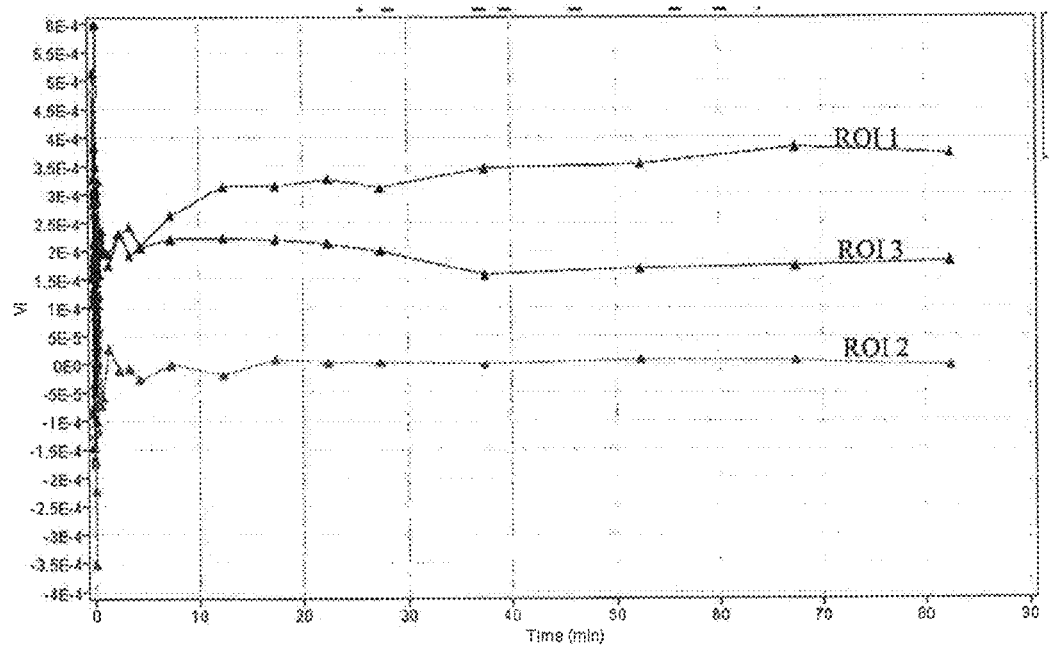
FIG. 9 shows ROI quantification of [$^{68}$Ga]CPCR4-2 activity levels in OH-1 tumor, muscle and background.
Figure 14:
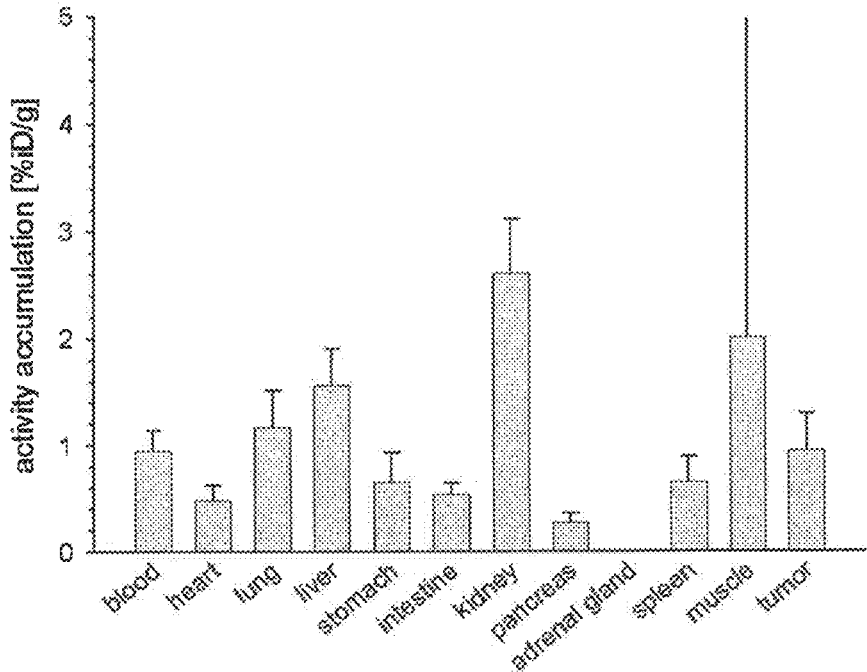
FIG. 14 shows biodistribution of yorn'(AMBS-[$^{68}$Ga]DOTA)RNalG ([$^{68}$Ga]CPCR4-2) in SKBR3 tumor bearing CD1 nu/nu mice at 60 min p.i., n 4.
Figure 15:
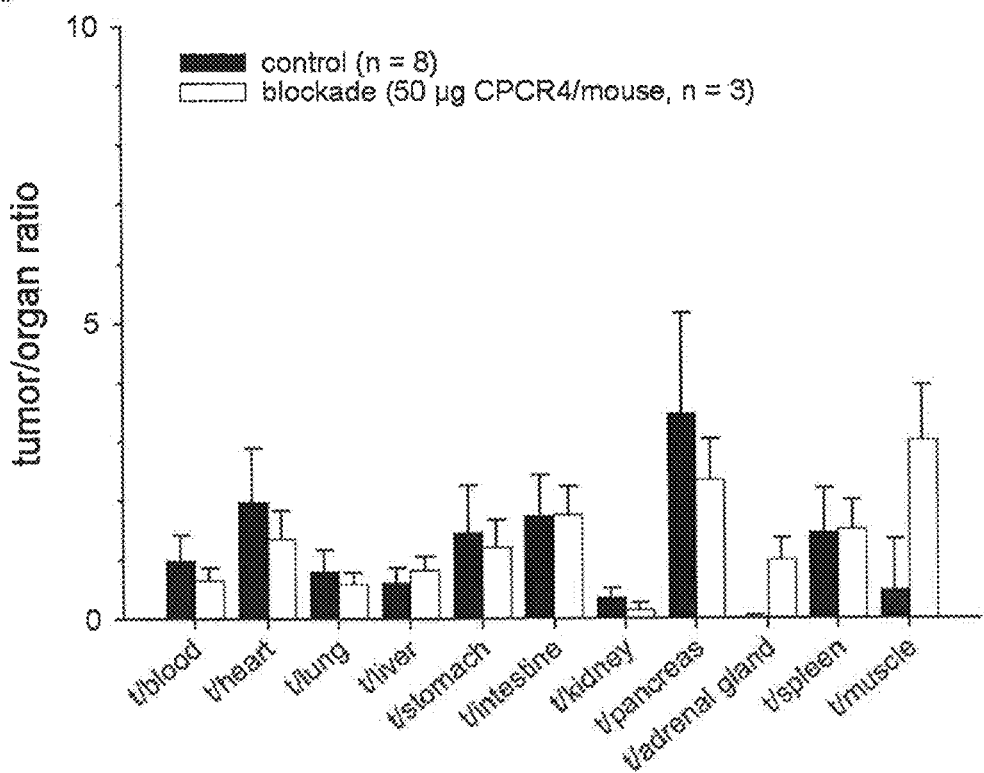
FIG. 15 shows tumor-to-organ ratios of yorn'(AMBS-[$^{68}$Ga]DOTA)RNalG (SKBR3 tumor bearing CD1 nude mice, 60 min p.i., n=3-4. Results are expressed as tumor-to-organ ratio.
Figure 16:
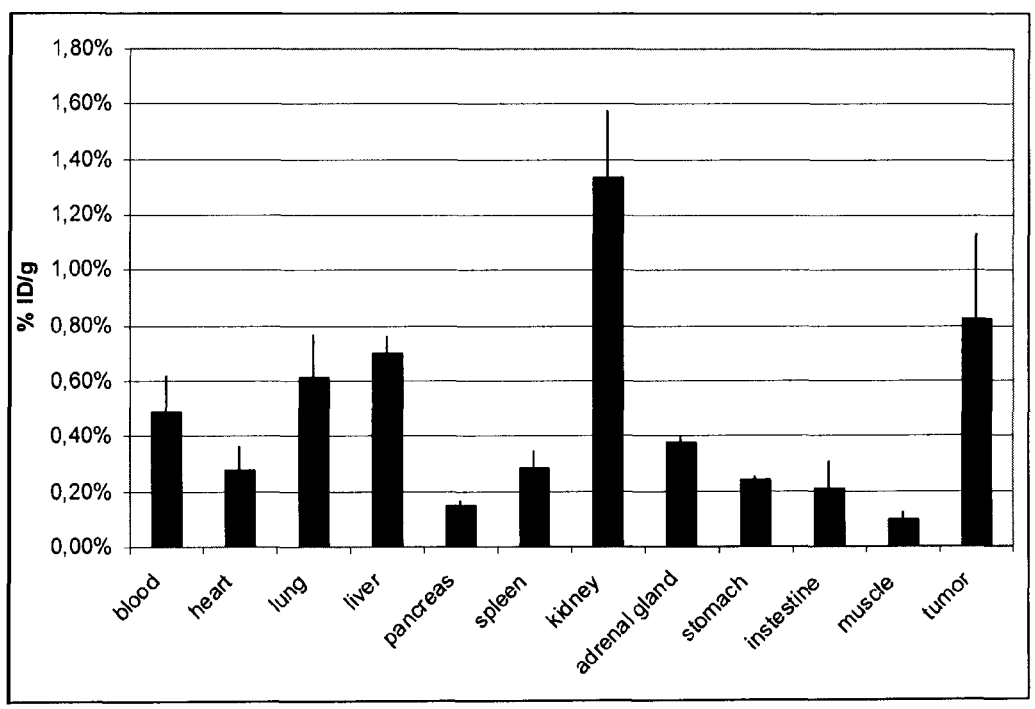
FIG. 16 shows biodistribution of [$^{68}$Ga]CPCR4-2 in SUDHL4 tumor bearing CD1 nu/nu mice.
Figure 17A:
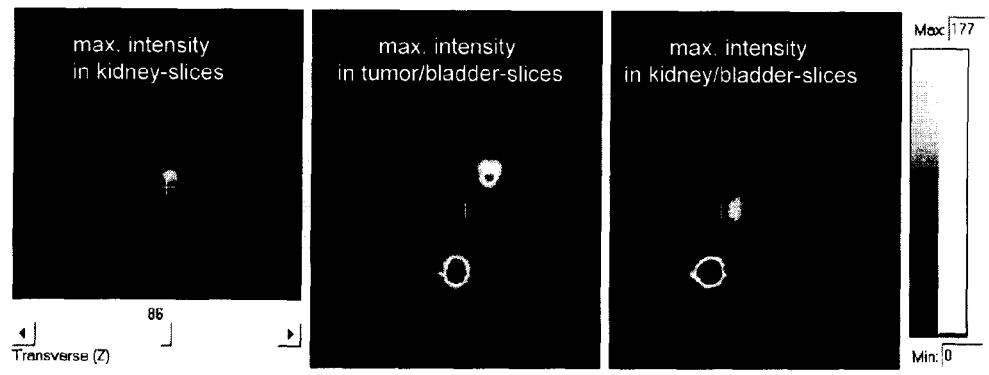
FIG. 17A shows PET imaging, 1 h post injection of the $^{68}$Ga-CPCR4-2.1
Figure 17B:
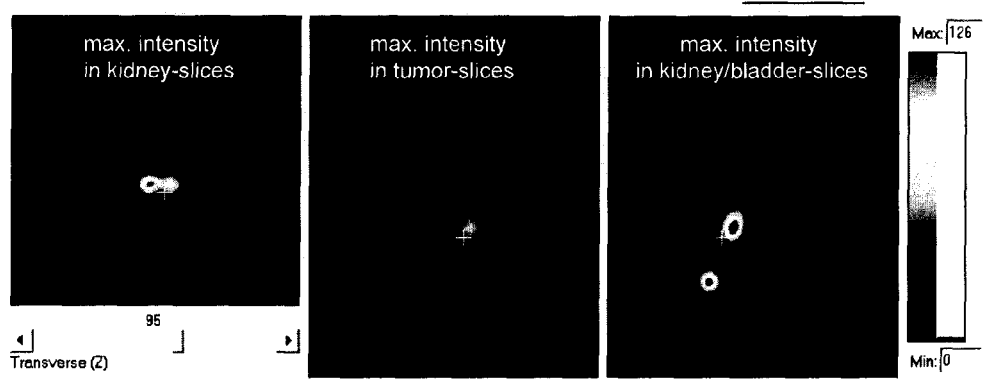
FIG. 17B shows PET imaging of an OH-1 bearing mouse, 1 h post injection of $^{68}$Ga-CPCR4-2.1 in the presence of an excess of cold CPCR4 peptide.
Figure 18A:
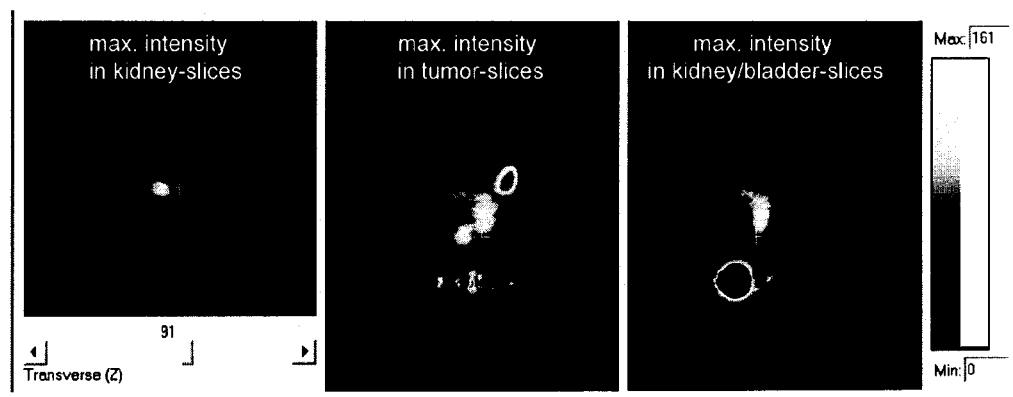
FIG. 18A shows PET imaging, 1 h post injection of the $^{68}$Ga-CPCR4-2.1
Figure 18B:
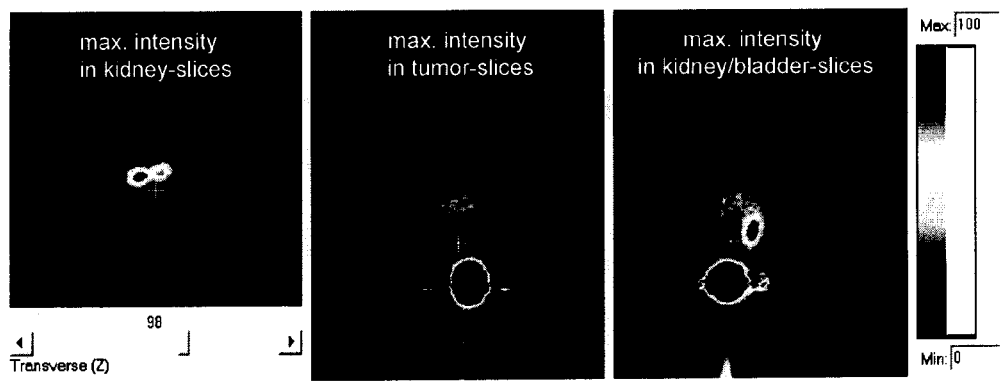
FIG. 18B shows PET imaging of an OH-1 bearing mouse, 1 h post injection of $^{68}$Ga-CPCR4-2.1 in the presence of an excess of cold CPCR4 peptide.

The results of performed studies are depicted in the Figures, particularly in FIGS. 4 to 18. FIG. 4 shows biodistribution of [$^{68}$Ga]CPCR4-2 in A431 tumor bearing CD1 nu/nu mice at 1 h p.i. Results are expressed as percent injected dose per gram tissue weight (% ID/g); 1 h p.i.; n=8. FIG. 5 shows tumor-to-organ ratios of yorn'(AMBS-[$^{68}$Ga]DOTA) RNalG (A431 tumor bearing CD-1 nude, 60 min p.i., n=3-5. Results are expressed as tumor to organ ratio (blockade n=3 in white; control n=5 in black). FIG. 6 shows biodistribution of [$^{125}$I] yorn'(AMBS-DOTA(Ga))RNalG ([$^{125}$I]Ga-CPCR4-2) in HT-29 tumor bearing CD1 nu/nu mice at 60 min p.i., n=4. In this study, yorn'(AMBS-DOTA(Ga))RnalG (Ga-CPCR4-2) labelled with $^{125}$I was used for the experiments. Results are expressed as percent injected dose per gram tissue weight (% ID/g). FIG. 7 shows tumor-to-organ ratios of [$^{125}$I]yorn' (AMBS-DOTA(Ga))RNalG (FIT-29 tumor bearing CD1 nude mice, 60 min p.i., n=4). Results are expressed as tumor to organ ratios. FIG. 8 shows biodistribution of [$^{68}$Ga] CPCR4-2 in OH-1 tumor bearing CD1 nu/nu mice at 1 h p.i. Results are expressed as percent injected dose per gram tissue weight (% ID/g); 1 h p.i.; n=6. FIG. 9 shows ROI quantification of [$^{68}$Ga]CPCR4-2 activity levels in OH-1 tumor, muscle and background. ROI 1: tumor; ROI 3: muscle; ROI 2: background. FIG. 10 shows PET imaging of OH-1 tumor bearing CD1 nu/nu mouse using [$^{68}$Ga]CPCR4-2. A PET/CT image of a mouse is shown in transaxial, coronal and saggital view (from left to right). Injected activity: 10 MBq; PET Scanner: Inveon Siemens; Duration of Scan: 90 min, on-bed-injection; Scan mode: dynamical (1 sec and 1 picture per frame, 39 frames). FIG. 11 shows SPECT imaging of OH-1 tumor bearing CD1 nu/nu mouse using [177Lu]CPCR4-2 (2.9.2009). Injected activity 22 MBq; SPECT Scanner: Nano-SPECT Bioscan; Duration of Scan: 72 min (60-75 min after tracer injection); Scan mode: 48 projections, 90 s per projection; summation image. FIG. 12 shows biodistribution of yorn'(AMBS-[$^{68}$Ga]DOTA)RNalG ([$^{68}$Ga]CPCR4-2) in PC-3 tumor bearing CD1 nu/nu mice at 60 min p.i., n=4. Results are expressed as percent injected dose per gram tissue weight (% ID/g); 1 h p.i.; n=4. FIG. 13 shows tumor-to-organ ratios of yorn'(AMBS-[$^{68}$Ga]DOTA)RNalG (PC-3 tumor bearing CD1 nude mice, 60 min p.i., n=3-4. Results are expressed as tumor-to-organ ratio. FIG. 14 shows biodistribution of yorn'(AMBS-[$^{68}$Ga]DOTA)RNalG ([$^{68}$Ga] CPCR4-2) in SKBR3 tumor bearing CD1 nu/nu mice at 60 min p.i., n=4. Results are expressed as percent injected dose per gram tissue weight (% ID/g); 1 h p.i.; n=8. FIG. 15 shows tumor-to-organ ratios of yorn'(AMBS-[$^{68}$Ga]DOTA)RNalG (SKBR3 tumor bearing CD1 nude mice, 60 min p.i., n=3-4. Results are expressed as tumor-to-organ ratio. FIG. 16 shows biodistribution of [$^{68}$Ga]CPCR4-2 in SUDHL4 tumor bearing CD1 nu/nu mice. Results are expressed as percent injected dose per gram tissue weight (% ID/g); 1 h p.i.; n=2. FIG. 17 shows $^{68}$Ga-CPCR4-2.1: imaging in OH-1 tumor bearing mice. FIG. 17A shows PET imaging, 1 h post injection of the $^{68}$Ga-CPCR4-2.1 and FIG. 17B shows PET imaging of an OH-1 bearing mouse, 1 h post injection of $^{68}$Ga-CPCR4-2.1 in the presence of an excess of cold CPCR4 peptide. FIG. 18 shows another example of $^{68}$Ga-CPCR4-2.1 imaging in OH-1 tumor bearing mice. FIG. 18A shows PET imaging, 1 h post injection of the $^{68}$Ga-CPCR4-2.1 and FIG.

18B shows PET imaging of an OH-1 bearing mouse, 1 h post injection of $^{68}$Ga-CPCR4-2.1 in the presence of an excess of cold CPCR4 peptide.

In summary, the above experiments suggest that the compounds of the present invention have a sufficiently high specific enrichment. Moreover, the above experiments suggest that suitably labeled compounds of the invention are suitable for imaging applications, such as as contrast agents e.g. for depicting the CXCR4 receptor status in vivo.

REFERENCES

Aldrich, J. V.; Kumar, V (2003) Methods of synthesizing and using derivatives of [2-(2-aminoethoxy)ethoxy]acetic acid: United States of America; pp 14.

Barry Edwards, W.; Akers, W. J.; Ye, Y.; Cheney, P. P.; Bloch, S.; Laforest, R.; Aehilefu, S. Multimodal Imaging of Integrin Receptor-Positive Tumors by Bioluminescence, Fluorescence, Gamma Scintigraphy and SPECT Methods Using a Cyclic RGD Peptide Labeled with a Near Infrared Fluorescent Dye and a Radionuclide, Nuclear Imaging 2009, 8, 2, 101-110.

Burger-Kentischer A et al, 2002, Expression of macrophage migration inhibitory factor in different stages of human atherosclerosis, Circulation 105, 1561-1566.

Demmer, O.; Dijkgraaf, I.; Schottelius, M.; Wester, H. J.; Kessler, H (2008) Introduction of functional groups into peptides via N-alkylation. Organic Letters, 10, 2015-2018.

N. Fujii, S. Oishi, K. Hiramatsu, T. Araki, S. Ueda, H. Tamamura, A. Otaka, S. Kusano, S. Terakubo, H. Nakashima, J. A. Broach, J. O. Trent, Z. X. Wang, S. C. Peiper, Angewandte Chemie-International Edition 2003, 42, 3251.

Hansson, G K, 2005, Inflammation, atherosclerosis, and coronary artery disease, N. Engl. J. Med. 351, 1985-1695, Kim J, Takeuchi H, Lain S T, Turner R R, Wang H J, Kuo C, Foshag L, Bilchik A J, Hoon D S (2005) Chemokine receptor CXCR4 expression in colorectal cancer patients increases the risk for recurrence and for poor survival. J Clin Oncol.; 23(12):2744-53.

Kuehl H, Veit P, Rosenbaum S J, Bockisch A, Antoch G (2007) Can PET/CT replace separate diagnostic CT for cancer imaging? Optimizing CT protocols for imaging cancers of the chest and abdomen, J Nucl Med.; 48 Suppl 1:45 S-57S.

J. P. Levesque and I. G. Winkler, Curr Opin Organ Transplant. 2008 February; 13(1):53-8)

Libby P. (2002) Inflammation in atherosclerosis. Nature 420, 868-874.

Mizukami, S.; Takikawa, R.; Sugihara, F.; Hori, Y.; Tochio, H. et al (2008) Paramagnetic relaxation-based F-19 MRI probe to detect protease activity. Journal of the American Chemical Society, 130, 794-795.

Phillips R J, Burdick M D, Lutz M, Belperio J A, Keane M P, Stricter R M (2003) The stromal derived factor-1/CXCL12-CXC chemokine receptor 4 biological axis in non-small cell lung cancer metastases. Am J Respir Crit Care Med.; 167(12):1676-86.

Ross R (1993), The pathogenesis of atherosclerosis: a perspective for the 1990s. Nature 362:801-80).

Schober A. Bernhagen J, Weber C. Chemokine-like functions of MIF in atherosclerosis, J. Mol. Med. (2008), 86, 761-770.

Shah K, Weissleder R. (2005) Molecular optical imaging: applications leading to the development of present day therapeutics. NeuroRx.; 2(2):215-25.

Taniuchi S, Masuda M, Fujii Y, Izawa K, Kanegane H, Kobayashi Y (2005) The role of a mutation of the CXCR4 gene in WHIM syndrome. Haematologica; 90(9):1271-2.

Van der Plas, S. E.; Gea, A.; Figaroli, S.; De Clercq, P. J. (2008) Madder, A. Synthesis of a tripodal scaffold for solid phase synthesis of artificial receptors. European Journal of Organic Chemistry, 1582-1588.

Weissleder R, Ntziachristos V (2003) Shedding light onto live molecular targets. Nat Med.; 9(1):123-8.

Weissleder R, Pittet M J (2008) Imaging in the era of molecular oncology, Nature; 452(7187):580-9.

Yang, P. Y.; Wu, H.; Lee, M. Y.; Xu, A. (2008) Srinivasan, R. et al. Solid-phase synthesis of azidomethylene inhibitors targeting cysteine proteases. Organic Letters, 10, 1881-1884.

Zhang et al., Inorg. Chem. 37(5), 1998, 956-963.
WO 89/07456
WO 97/31657
WO 2007/096662
WO 2008/08854
WO 2009/027706
WO 2009/109332
WO 2009/134382

The invention claimed is:
1. A compound having a structure according to formula I

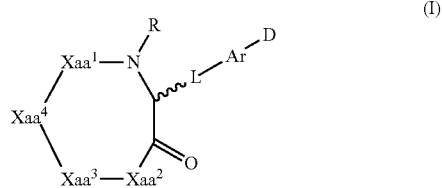

or a pharmaceutically acceptable salt thereof,
wherein $Xaa^1$ is D-tyrosine, $Xaa^2$ is arginine, $Xaa^3$ is naphthylalanine (Nal) and $Xaa^4$ is glycine,
R is methyl,
L has the formula —$(CH_2)_3$—NH—, and
Ar is selected from the group consisting of

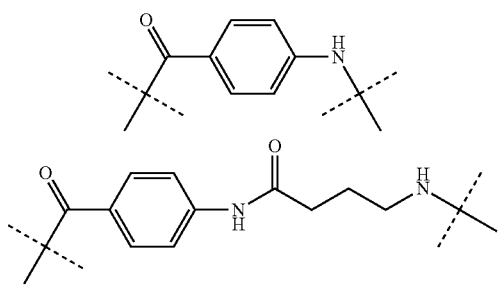

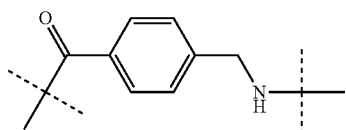
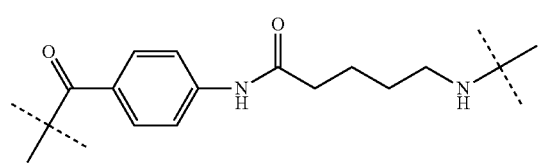
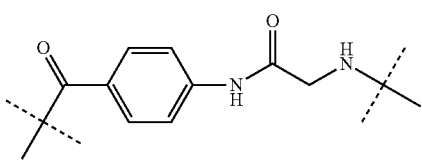
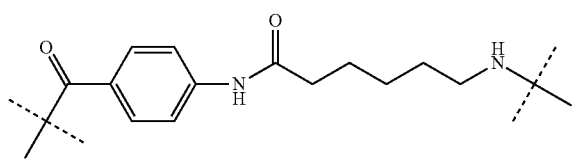
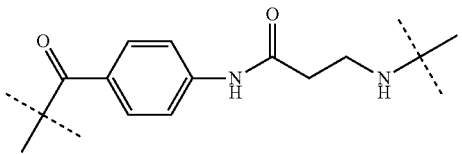
and D is
i) DOTA,
ii) a combination of a Ga atom and DOTA, or
iii) a combination of a Ga atom and DOTA, with the complexation agent DOTA being covalently bound to Ar.
2. The compound of claim 1, wherein Ar is:
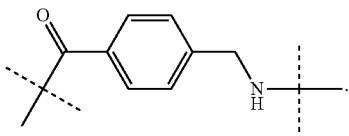
3. The compound of claim 1, wherein the Ga atom is a radionuclide.
4. The compound of claim 1, wherein the Ga atom is a Ga radionuclide.
5. A compound
i) having the structure:
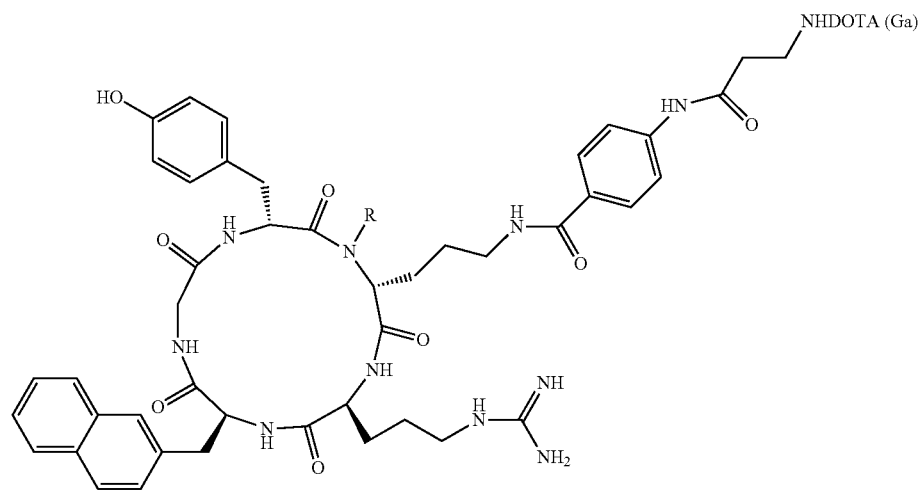

wherein R is methyl
or
ii) having the structure:

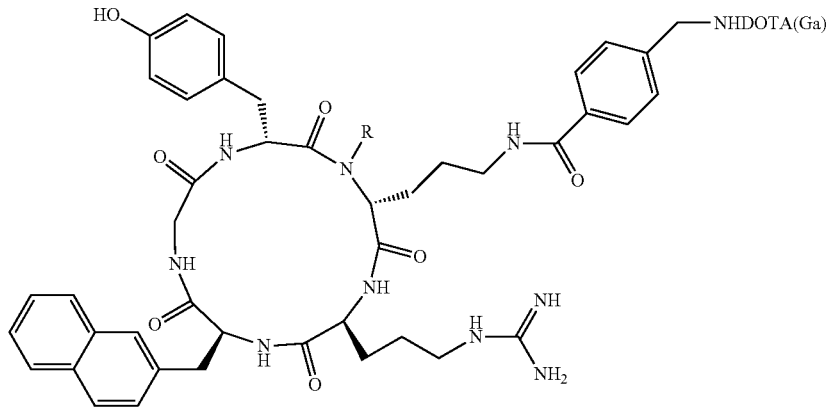

wherein R is methyl.

6. A pharmaceutical composition comprising a compound as defined in claim 1 and at least one pharmaceutically acceptable excipient.

7. A diagnostic method
for the diagnosis of a CXCR4 receptor-related disease or disorder which comprises
contacting receptors in a patient with a compound of claim 1;
detecting the location and/or quantity of CXCR4 receptor in said patient by imaging the compound in the patient with a detectable label; and
correlating the location and/or quantity of the CXCR4 receptors to a CXCR4-related disease or disorder wherein the CXCR4-related disease or disorder is selected from the group consisting of multiple sclerosis (MS), lupus erythematosus, Sjögren's syndrome, ulcerative colitis, rheumatoid arthritis, atherosclerosis, thrombosis, asthma, Alzheimer's disease, vasculitis, HIV infection, benign and malignant tumors, myocardial infarction, and aneurysm.

8. A method of imaging CXCR4 receptors, which comprises contacting said receptors with a compound as defined in claim 1, and detecting the compound of formula 1 with a detectable label wherein an image is generated.

9. A method of imaging CXCR4 receptor,
comprising administering a compound as defined in claim 1 to a sample or a subject and detecting the compound with a detectable label wherein an image is generated.

10. A method of imaging CXCR4 receptors, which comprises contacting said receptors with a composition as defined in claim 6; and detecting the compound of formula 1 with a detectable label wherein an image is generated.

11. The method of claim 10, wherein the imaging is medical imaging.

12. The method of claim 11, wherein the medical imaging is diagnostic imaging.

13. The compound of claim 3, wherein the Ga atom is a non-radioactive isotope.

14. The compound of claim 3, wherein the Ga atom is $^{66}$Ga, $^{67}$Ga or $^{68}$Ga.

15. The method of claim 8, wherein the imaging is medical imaging.

16. The method of claim 8, wherein the medical imaging is diagnostic imaging.

17. The compound of claim 3, wherein the Ga atom is a non-radioactive isotope selected from the group consisting of $^{66}$Ga, $^{67}$Ga or $^{68}$Ga.

* * * * *